US010943692B1

(12) United States Patent
Lynn et al.

(10) Patent No.: US 10,943,692 B1
(45) Date of Patent: Mar. 9, 2021

(54) SYSTEM AND METHOD FOR GENERATING QUATERNARY IMAGES OF BIOLOGIC FORCE PROPAGATION AND RECOVERY

(71) Applicant: Lawrence A. Lynn, Columbus, OH (US)

(72) Inventors: Lawrence A. Lynn, Columbus, OH (US); Eric N. Lynn, Villa Ridge, MO (US)

(73) Assignee: Lawrence A. Lynn, Columbus, OH (US)

( * ) Notice: Subject to any disclaimer, the term of this patent is extended or adjusted under 35 U.S.C. 154(b) by 1050 days.

(21) Appl. No.: 15/254,575

(22) Filed: Sep. 1, 2016

Related U.S. Application Data

(63) Continuation-in-part of application No. 14/193,700, filed on Feb. 28, 2014, now abandoned, and a continuation-in-part of application No. 14/194,118, filed on Feb. 28, 2014, now abandoned, and a continuation-in-part of application No. 13/844,381, filed on Mar. 15, 2013, now Pat. No. 10,366,790, which is a continuation of application No. 12/437,417, filed on May 7, 2009, now Pat. No. 9,053,222.

(60) Provisional application No. 61/770,919, filed on Feb. 28, 2013, provisional application No. 61/770,971, filed on Feb. 28, 2013, provisional application No.
(Continued)

(51) Int. Cl.
G16H 40/63 (2018.01)
G06F 19/00 (2018.01)
G16H 10/60 (2018.01)

(52) U.S. Cl.
CPC ......... *G16H 40/63* (2018.01); *G06F 19/3456* (2013.01); *G16H 10/60* (2018.01)

(58) Field of Classification Search
CPC ..... G16H 40/63; G16H 10/60; G06F 19/3456
USPC ........................................ 705/2–3
See application file for complete search history.

(56) References Cited

U.S. PATENT DOCUMENTS 9,053,222 B2 * 6/2015 Lynn ..................... G06Q 50/22
2002/0099273 A1 * 7/2002 Bocionek ............... G16H 40/63
600/300
(Continued)

FOREIGN PATENT DOCUMENTS

WO 2013/074708 A1 5/2013

OTHER PUBLICATIONS

Oct. 10, 2016—(EP) Extended European Search Report—14757699.5.
(Continued)

Primary Examiner — Michael Tomaszewski
(74) Attorney, Agent, or Firm — Vorys, Sater, Seymour and Pease LLP; Rex W. Miller, II

(57) ABSTRACT

A patient monitoring system is disclosed comprising at least one processor programmed to process medical data derived from a patient or medical records repository and to compose interconnected cascades of sepsis by linking or grouping four fundamental elements which comprise; a perturbation, at least one perturbation force which is capable of inducing and may have induced the perturbation, a recovery, and at least one recovery force which is capable of inducing and may have induced the perturbation. The four elements are linked or grouped by the processor to generate a quaternary which may be characterized as solved or unsolved.

14 Claims, 37 Drawing Sheets

Related U.S. Application Data

61/200,162, filed on Nov. 25, 2008, provisional application No. 61/126,906, filed on May 7, 2008.

(56) References Cited

U.S. PATENT DOCUMENTS

| | | | | |
|---|---|---|---|---|
| 2003/0158466 A1* | 8/2003 | Lynn | .................. | G16H 50/70 |
| | | | | 600/300 |
| 2004/0097460 A1* | 5/2004 | Ivey | .................. | C12Q 1/6837 |
| | | | | 514/44 R |
| 2006/0235324 A1* | 10/2006 | Lynn | .................. | A61M 16/026 |
| | | | | 600/538 |
| 2008/0235049 A1* | 9/2008 | Morita | .................. | G16H 50/20 |
| | | | | 705/2 |

OTHER PUBLICATIONS

Oct. 27, 2016—(EP) Supplementary European Search Report—14757699.5.

Zuev, Sergey M. et all., "Sepsis Progression and Outcome: A Dynamical Model," Theoretical Biology and Medical Modelling, Biomed Central, Ltd., London, GB, vol. 3, No. 1, Feb. 15, 2006, 15 pages.

Allen, Richard J. et al., "From Physics to Pharmacology?" Reports on Progress on Physics, Institute of Physics Publishing, Bristol, GB, vol. 74, No. 1, Dec. 3, 2010, 19 pages.

* cited by examiner

100

400

SYSTEM AND METHOD FOR GENERATING QUATERNARY IMAGES OF BIOLOGIC FORCE PROPAGATION AND RECOVERY

PRIORITY

This application claims the benefit of and is a continuation-in-part of U.S. application Ser. No. 14/194,118, filed Feb. 28, 2014, which claims the benefit of U.S. Provisional Application Ser. No. 61/770,919, filed Feb. 28, 2013, and which claims the benefit of U.S. Provisional Application Ser. No. 61/770,971, filed Feb. 28, 2013.

This application claims the benefit of and is a continuation-in-part of U.S. application Ser. No. 14/193,700, filed Feb. 28, 2014, which claims the benefit of U.S. Provisional Application Ser. No. 61/770,919, filed Feb. 28, 2013, and which claims the benefit of U.S. Provisional Application Ser. No. 61/770,971, filed Feb. 28, 2013.

This application claims the benefit of and is a continuation-in-part of U.S. application Ser. No. 13/844,381, filed Mar. 15, 2013, which is a continuation of U.S. application Ser. No. 12/437,417 (now U.S. Pat. No. 9,053,222), filed May 7, 2009, which claims the benefit of U.S. Provisional Application Ser. No. 61/200,162, filed Nov. 25, 2008, and which claims the benefit of U.S. Provisional Application Ser. No. 61/126,906, filed May 7, 2008.

The disclosures of each of the above applications, including any incorporations by reference therein, are hereby incorporated by reference in their entireties, as if fully set forth herein.

BACKGROUND

Human pathophysiology is highly complex and it is very difficult for physicians and nurses to timely detect many adverse clinical conditions in the many settings. U.S. Pat. Nos. 8,241,213, 8,152,732, 7,758,503, 7,398,115 and 7,081,095, as well as U.S. patent application Ser. Nos. 12/437,417, 12/437,385, 12/629,407 13/677,291, and 13/677,288 (the entire contents of each of these patents and patent applications are incorporated by reference as if completely disclosed herein) disclose processor methods, time series matrix analysis and objectification, processing systems, patient monitors for timely detection, identification, quantification, tracking, and generation of dynamic displays of sepsis and other conditions. These patents and patent applications provide additional background for the embodiments described herein.

Diagnostic systems and their limitations are discussed in U.S. Patent Application Ser. No. 61/770,919 filed Feb. 28, 2013, entitled "Patient storm Tracker and Visualization Processor," (the entire contents of each of these applications are incorporated by reference as if completely disclosed herein). This application also provides background for the embodiments described herein. Some embodiments described herein relate to systems and methods for analyzing complex datasets of medical records. FIG. 1 shows a conventional medical repository system 100 with associated cognitive support 102. In this figure a central repository 104 (such as Microsoft Health Vault or a hospital system's server or data repository) may store massive amounts of clinical data, for example, in database fields. Hospitals access the databases for clinical management of the patient 106. In many cases, patients may also observe their own data using secure portals.

Physicians and patients often find it difficult to deal with the complexity of the data available from these portals and especially to identify causation of complex or subtle perturbations. A major portion of the complexity of medical data is derived from the highly interrelated dynamic patterns of perturbations of the compartmentalized densities of human biologic particles. The dynamic complexity of the relational patterns of cascading biologic particle perturbations provides a major barrier to timely care.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements may have similar reference numerals.

DETAILED DESCRIPTION OF EMBODIMENTS

Figure 2:
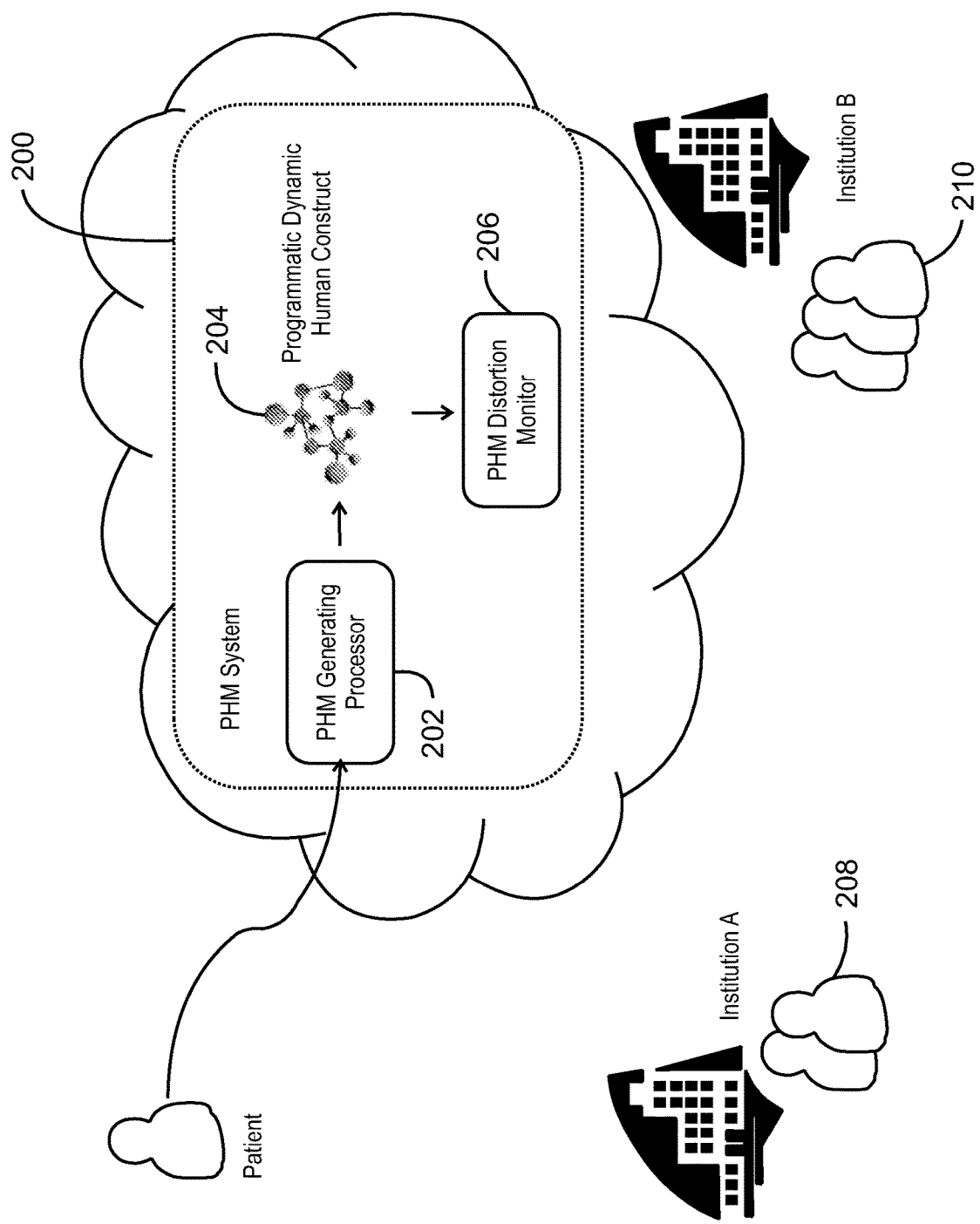
FIG. 2 depicts the PHM processor, some primary components, with input from patient data and access from multiple institutions.
Figure 3:
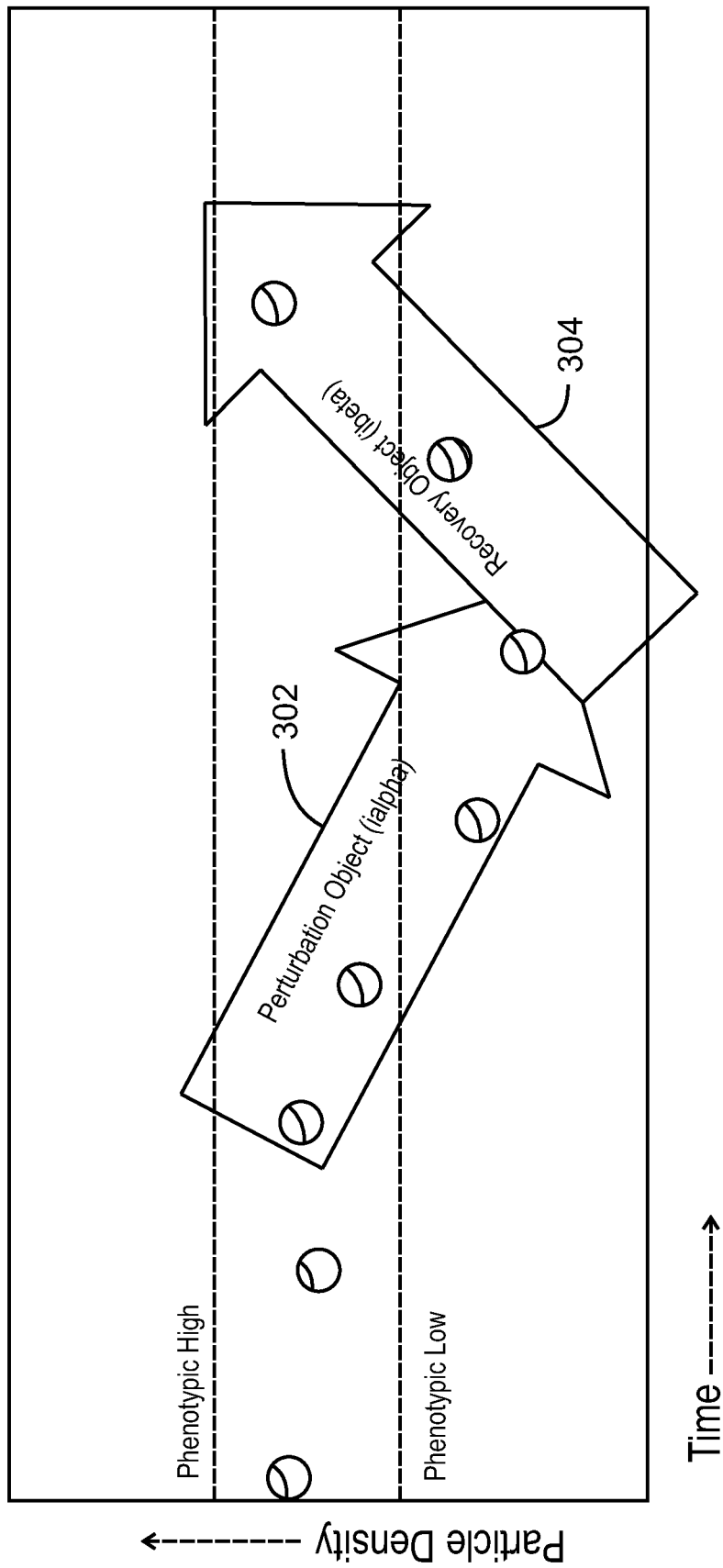
FIG. 3 depicts ialpha and ibeta events in a perturbation-recovery binary as accessed in i-space.
Figure 4:
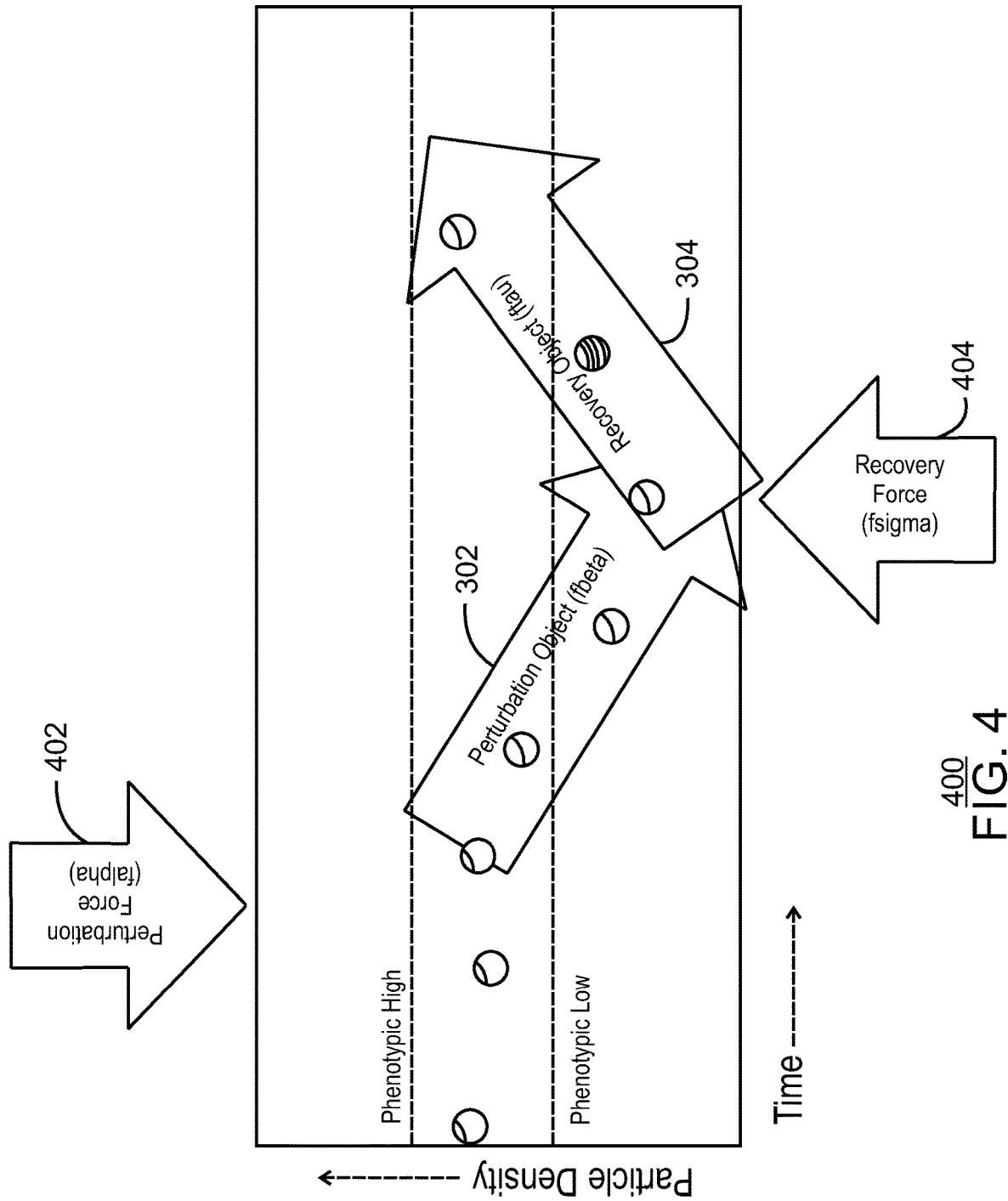
FIG. 4 depicts the same perturbation-recovery binary as in FIG. 3 as seen within f-space with perturbation and recovery forces depicted.

An embodiment described herein comprises a PHM system 200 of FIG. 2 that includes a processor (also referred to herein as the PHM generating processor 202 of FIG. 2) programmed to generate an image of causation of adverse conditions comprising a dynamic multi-dimensional parallel time construct (also referred to herein as a programmatic dynamic human construct 204 of FIG. 2) of a human or patient 206 from medical data which may be a causation construct which is comprised of perturbations and at least one force which caused or induced the perturbations. The dynamic human construct 204 exists in parallel with the human and provides a limited companion parallel instance of the biologic human. In one embodiments, the processor 202 can be programmed to analyze the parallel human construct 204 for dynamic distortions indicative of, for example, disease, drug reactions, age related declines in function, or other clinical failures. As constructed by the processor 202, one embodiment of the parallel human construct 204 is comprised of a highly organized and compartmentalized time matrix. The time matrix may be comprised of grouped, bonded, linked, related, encapsulated, or otherwise connected events and forces which may be converted to objects. In an embodiment, four fundamental events and forces which are used to build the time matrix are; perturbations 302 of FIG. 3 (such as particle density perturbations), perturbation forces 402 of FIG. 4 which induced the perturbations, recoveries 304 of FIG. 3 (such as particle density perturbations), and recovery forces 404 of FIG. 4, which induced the recoveries. In one embodiment, when linked these form a "force quaternary" (which is shown in FIG. 3). A force quaternary may be a fundamental repeating structural component of distortions along at least one portion of the PHM. According to some embodiments, this type of distortion of the biologic matrix is called a "polyquaternary distortion". A polyquaternary distortion 400 may, as shown in FIG. 4, be modeled as a growing molecule which develops upon the occurrence of a force sufficient to induce a perturbation 302 in the PHM and initially occurs in the region of the PHM which initially receives the force. If the perturbation force 402 is strong it may induce perturbation force cascade which projects through the particle densities of the PHM and expanding outwardly in the PHM to involve a progressively greater number of particle densities and a progressively greater number of systems. This comprises a causation construct or a causation cascade as the forces which induce or cause the perturbations define, with the perturbations, the construct which may be for example a causation time matrix. In cascading conditions such as sepsis, the perturbation force cascade may project along and within the PHM as a cone. The perturbation force 402 which induced the cone is called an apical perturbation force and is one of the causation forces of the cascade. There may be more than one force which comprises the apical force. The apical force (which may be endogenous or exogenous) may have been induced or more exogenous trigger forces.

In one embodiment, stasis, as well as perturbation 302 and recovery objects 304 are identified, related, aggregated and stored. Stasis objects represent and quantify the maintenance of particle densities within phenotypic ranges. Stasis object provide a positive representation of equilibrium within the system. Further stasis objects can provide quantification of the equilibrium. In one embodiment, stasis is quantified simply by referring to sections of the time series in which there are no perturbation or recovery events. In this approach a matrix in stasis is free of perturbation and it is the distortions which are defined by the force quaternaries. In another embodiment, stasis objects are defined by the normal forces which maintain the stasis object in its normal state, which may be a variable state, such as a cycling state. In this embodiment, a perturbation may be a physiologic perturbation or pathologic perturbation and recovery may be physiologic or pathologic. In this approach, recovery may be physiologic recovery from a physiologic perturbation, physiologic recovery from a pathologic perturbation, or a pathologic recovery from a pathologic perturbation. With this approach the entire matrix may be defined by quaternaries to the extent that the forces are known or reasonably assumable based on the dynamic motion image of the matrix.

In one embodiment, stasis objects are used as building blocks which may represent, at a higher level, physiologic perturbation and/or physiologic recovery. For example, rises, falls and reciprocations in chest wall pressure may be stored in terms of stasis objects if within phenotypic ranges. However, in the context of other objects these objects may represent or participate in relational objects that indicate either pathologic or physiologic perturbation or recovery. In this way, stasis objects provide the encapsulation of state, and change in state, which can be interpreted within the wider context of the entire matrix.

In one embodiment a recovery or perturbation may also be defined as exogenous, endogenous, or mixed depending on the force which induced it. For example, an exogenous recovery can be so designated when the recovery is actually derived from outside force (such as the administration of platelets causing a recovery of platelet density. In this example the recovery force (for example infusion of 6 units of platelets over 30 minutes), is an exogenous force and the platelet rise (recovery) responsive to the platelet infusion is an exogenous recovery. A grouping of recoveries which comprise recoveries associated with a polyquaternary distortion may be combined to generate a cascade of recoveries and recovery forces. If this group is endogenous, this group or cascade may be rendered as a motion image in a visualization as for example a motion image of a recovering storm which provides a different visual designation then the perturbation and perturbation force portion of the storm and a different visual designation then exogenous recoveries and exogenous recovery forces. In this way grouping or cascades of recoveries which are exogenous or single recoveries which are exogenous, may be identified in the matrix visualization with a different color or other marking so that they are not confused with endogenous recoveries by the healthcare worker. In the matrix visualizations, each of the above different types of perturbation and distortion and each different type of recovery may be designated by different colors or by other designations.

In one embodiment the processor 202 detects and analyzes perturbations to detect the presence of a distortion of the PHM. Upon identification of one or more perturbations, the processor 202 seeks to solve the quaternary, diquaternary and/or polyquaternary which comprise the distortion. The occurrence of a high and sustained force (as, for example induced by a biologic invasion by multiplying bacteria) induces at least one expanding polyquaternary. Since different types of distortion of the PHM, as for example caused by different disease types, produce different polyquaternaries, the processor 202 solves the polyquaternary by building it, as by the identification and insertion of a progressive number of its components into a diagnostic construct of the matrix distortion which optimally includes detection of the apical force or forces and any exogenous triggering force or forces.

Perturbations may comprise, for example, the perturbation of particle densities, perturbation of phenotypic energy states (as, for example, implied by temperature), the introduction of foreign organisms, the perturbation, reduction and/or elimination of health enhancing organisms, the perturbation of standard motions (including variations such as pulsations and oscillations), the damage to structural integrity, the perturbation of structural and/or functional capacity, the perturbation of the mental state of the patient to name a few. The presence of abnormally high or low diagnostic values (such as low or high particle density values) may also comprise and/or be considered indicative of the occurrence of a perturbation and may be substituted for a perturbation in the matrix groupings of perturbation force, perturbation, recovery force, and recovery.

According to some embodiments, the state of health or disease of any human may be definable as a function of the distortions along his or her PHM. Although many types of perturbations and forces may occur, a portion of the PHM is comprised of the densities of biologic particles. Distortions comprised of dynamic perturbations and recoveries of those densities, and the dynamic forces acting on those densities represent some of the dangerous and diagnostic distortions of the PHM. The detailed approach to identification of particle density perturbations, forces, quaternaries, and polyquaternaries along the PHM provided herein provides examples for application to other types of perturbations, forces, quaternaries, and polyquaternaries.

According to one aspect of some embodiments, (as shown in FIG. 2) the parallel instance (which may be include distortions comprised of solved and unsolved quaternaries) is monitored by a processor 202 for health and disease along with the biologic instance. The parallel instance may exist in the cloud, on a server, or another repository. As the parallel instance ages and new data are added the instance grows incorporating the new data in such a way that the past instance at any time may be accessed and/or fully reconstructed.

The parallel human construct 204 comprises a global integrated matrix called a "Parallel Human Time Matrix" (PHM). The matrix is constructed by a "PHM generating processor" and may be maintained in memory or persisted to storage as needed. The PHM is "grown" and "aged" over time over the life time of the human from which the construct is generated.

Since particle densities and patterns of particle densities in the PHM are forcefully maintained by density normalization forces a density change suggests either the loss of that normalization force(s), and/or the introduction of a new force that has overwhelmed the normalization force. Either condition comprises the equivalent of the introduction of an unbalanced density modifying force into the PHM which moves the particle density in the PHM to a new higher or lower value which generally will extend outside the phenotypic range producing a distortion of the PHM.

The PHM may integrate genetic code, and a sequenced human genome or a single gene may be positioned at the beginning of the matrix (for example as steps functions) when available. Genes or specific genetic codes or mutations, can be converted to objects and processed by the processor 202 as relational objects along the matrix and compared with particle densities, perturbations, distortions, and recoveries to identify relationships across populations between genetic information and the objects of the matrix. The PHM may further integrate particle densities, exogenous forces, endogenous forces, perturbations, and recoveries, as well as structural relationships, such as anatomic relationships. The PHM matrix may be an objectified time series matrix or another matrix construct. The PHM is monitored by a "PHM monitoring processor" (also referred to herein as a PHM distortion monitor 206). The PHM monitoring processor 206 may be the same general processor as the PHM generating processor 202 and when combined they are called collectively a "PHM processor" or "processor" or PHM system 200.

The present disclosure provides systems and methods for diagnosis, monitoring, and treatment of certain clinical conditions. A processor-based system may characterize and quantify patient physiological conditions by analyzing data relating the patient. In one embodiment, a database of is converted into a format which is favorable for searching and/or analysis of complex relational patterns of trends and variations. One such format is a time series matrix which itself may be formatted to generate an image or moving image of the abnormal components of the time-series matrix that may be further processed into operator-interpretable data.

In one embodiment the time-series matrix constructed by the processor may include a plurality of (e.g., hundreds or thousands) of individual time-series each including different chemical, electrical, mechanical, and/or state related parametric and/or non-parametric values of an individual patient. In one embodiment, data derived from the patient is organized into a comprehensive set of time series each aligned along a single time axis. Each individual time series is two-dimensional with one dimension being time but there are no other limits on second dimensions so that the matrix may have thousands of other dimensions in addition its unifying time dimension. For example the dimensions may include derivatives and frequency measures or calculations of values, calculated or measured relationship between a pluralities of values, time relationships between a plurality of values to name a few. In a few more examples, the dimensions may be further defined by an instantaneous magnitude value, a moving window derived averaged magnitude value, an instantaneous slope of any of the measured or calculated values, and moving window average of the slope of any of the measured values, an acceleration value or area related value, a peak or nadir value, a difference value, a recovery value, a threshold breach, a threshold approximation, a statistical parameter or value, a derivative value, a trend value, frequency domain derived value, to name a few.

One embodiment provides visibility into the complete matrix of patient data by direct search of a hospital's global and/or centralized medical records which may be automatic on a scheduled regular basis, continuous, triggered, or manual basis. Direct search allows rapid access to information relevant to the time and relationships involved complex failure cascade images or other patterns searched for, including outputting an identification of the patient exhibiting the image. The output can comprise a display located at the nurses station or another location and can include direct notification of the patient (as through a pager or phone attached to the patient, nurse or physician (which may be is capable of presenting the image for review). The detection therefore can occur at the central database repository at a central location for the hospital, hospital system, a region, or the entire world, with the provision of direct notification to the hospital, the caregiver, or the patient him or herself.

In one embodiment, for manual searching and/or for preparing the automatic search process a health worker or researcher is presented with a single search box in which the name of a condition, pattern or other occurrence can be entered. The health worker or researcher can then direct the patient safety processor to execute the search. Search results are presented in a paged display allowing for rapid scan. With each "hit" is presented a link to navigate into a screen of data time-relevant to the "hit" and data relevant to the occurrences that constitute the hit. This may include time series displays, occurrence stream displays, patient data, data with regard to the definition of the occurrence and/or constituent occurrences to name a few. A few of the characteristics of the search which can be used to narrow the view of the condition, pattern or other occurrence are listed below. The processor may be programmed to navigate the search using these characteristics. These will be discussed in more detail in the subsequent disclosure.

One embodiment includes a real-time processing method for searching for and detecting physiologic occurrences, physiologic failure and/or care having steps of: (1) converting medical records into at least one time series matrix of a particular configuration suitable for imaging (for example the configuration may be a 2 or more dimensional spatial configuration, and/or a 2 or more dimensional temporal configuration, and/or 2 or more dimensional frequency configuration, and/or another configuration suitable for imaging); (2) imaging the matrix to detect at least one image indicative of physiologic occurrences, physiologic failure, and/or care (which can for example include a sepsis cascade pattern, a sepsis shock pattern, a drug reaction pattern, to name a few); and (3) taking action based on the detection of the image which can for example, include outputting an indication (which can be an alarm) of the image and/or the likely cause of the image.

In one embodiment the time series matrix is processed (and this processing may be provided as part of the construction of the time series matrix to generate and time series matrix of events. In an embodiment these events are objects (such as objects having a relational hierarchy by the process of time-series objectification) thereby rendering an objectified time series matrix. The raw time series matrix and/or the time series matrix of events and/or the objectified time series matrix may be rendered in a particular configuration such as a particular default digital spatial and/or temporal and/or frequency and/or statistical configuration (to name a few), and then digitally imaged and the image characterized by known digital image recognition methods to detect a pattern and/or a plurality of patterns. These image patterns may be defined along the configuration of the matrix by selections of the user, by methods of digital image recognition, by statistical processing, as by neural net processing or by other methods as for example the methods described and/or listed in U.S. patent application Ser. No. 11/351,449 of the present inventors, the entire disclosure of which is hereby incorporated by reference for all purposes as if completely disclosed herein.

One embodiment includes a real-time processing method for detecting physiologic occurrences, physiologic failure and/or care having steps of: (1) converting medical records into at least one time series matrix of a particular configuration suitable for imaging; processing the matrix to render an matrix of time series of events (such as an objectified time series matrix (for example the configuration of the objectified time series matrix may be a 2 or more dimensional spatial configuration, and/or a 2 or more dimensional temporal configuration, and/or 2 or more dimensional frequency configuration, and/or another configuration suitable for imaging); (2) imaging the time series matrix of events to detect at least one image indicative of physiologic occurrences, physiologic failure, and/or care (which can for example include a sepsis cascade pattern, a sepsis shock pattern, a drug reaction pattern, to name a few); and (3) taking action based on the detection of the image which can for example, include outputting an indication (which can be an alarm) of the image and/or the likely cause of the image. Steps one, two and three, can be combined so that the time series matrix is built and objectified simultaneously or the time series are objectified and/or imaged and then the matrix is built and the matrix is then objectified and/or imaged. A default configuration of the raw time series matrix may be displayed directly with the images detected in raw form along the default configuration (as may be over-read by physicians or nurses). Alternatively, or in combination, another default configuration may be displayed for the user with the matrix presented in a processed (such as objectified) form with the detected images being highlighted or represented or replaced as icons, motion pictures, or other visual images. In another embodiment the detected images are reprocessed to simplify them and these reprocessed images may be digitally imaged to detect larger and more complex images. In this way the images themselves (much like the objects in the matrix) may have an inheritance hierarchy which reduces the complexity of the digital image recognition of the larger, complex and prolonged images.

One embodiment includes a real-time processing method having steps of: (1) converting medical records into a predetermined format for searching, as for example at least one time series matrix; (2) defining events such as objects (which can be relational events) along the time series matrix; (3) defining patterns including combinations of events, (4) using a processing search engine, searching for the events and/or the patterns and detecting at least one complex pattern or image (which can for example include a sepsis cascade pattern, a sepsis shock pattern, a drug reaction pattern, to name a few); and (4) taking action based on the detection which can for example, include outputting an indication (which can be an alarm) of the pattern(s) and/or the likely cause of the patterns.

According to one embodiment, a patient safety processor may generate a time series matrix for the early detection of septic shock or the pre-septic shock state by: (1) generating a large set of time-series of data of a patient including at least data relating to the physiologic state and/or care of a patient; (2) converting the datasets, including at least the monitored datasets and laboratory datasets into parallel time series; (3) identifying occurrences such as, for example, inflammatory occurrences, metabolic occurrences, volumetric occurrences, hemodynamic occurrences, therapy occurrences, hematologic occurrences, respiratory occurrences (to name a few), and the timing of the occurrences which relationally or collectively are indicative of the septic shock or pre-septic shock failure cascade; (4) identify and output an indication of the septic shock or pre-septic shock failure cascade; (5) identify and output the relational timing of the inflammatory occurrence, the hemodynamic occurrence, and the respiratory occurrence along the cascade; (6) identify and output length of the cascade; and (7) quantify the cascade as the cascade evolves and output a time series of the severity of the cascade.

Alternatively, the data from the objectified time series matrix may be converted into images, such as moving pictures. In one embodiment, data from the electronic medical records and patient monitors are used to generate graphical displays, which may include moving pictures of the patient condition. In an embodiment, such moving pictures, or animated displays, may be referred to as "motion pictures of physiologic condition" (MPPC). Provided herein is a processing system and method for generating real-time MPPC of clinical data. The data and/or images may also be analyzed to detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate the MPPC. In addition, the MPPC may also include a graphical representation of any treatment applied in association with the clinical condition.

Once the image or moving image (i.e. an image that includes more data over time as the patient monitoring progresses) MPPC of the patient condition has been generated, this image may be further processed to create an operator-interpretable indicator to assist in patient diagnosis and/or treatment. For example, the image may be directly compared to a database of similar images taken from patients with clinically confirmed diagnoses. The database image or composite of multiple images with the greatest similarity to the generated image may indicate the correct diagnosis for the patient. For example, if the generated moving image, particularly as the image progresses over time, has the greatest similarity to a database image indicating, for example, "septic shock cascade", "inflammation failure", "pulmonary thromboembolic cascade", "hemorrhagic failure cascade" to name a few, a processor may generate a text or other indicator to a healthcare provider indicating such a diagnosis. The processor may also indicate that additional tests should be ordered to confirm the diagnosis. The processor may also indicate and/or provide orders for specific treatments in light of the diagnosis. In an embodiment, a moving image may be indicative of two or more clinical conditions. The processor may indicate tests that may rule out one or more of such conditions. In addition, over time, one condition may be determined by the processor to be more likely while additional time-series data may also rule out another condition.

These database images may be formed from retrospective clinical data. In an embodiment, the images may be analyzed for similarity by any suitable technique, including image registration. In embodiments, the matches may be made by image similarity measures that include cross-correlation, mutual information, sum of squared intensity differences, and ratio image uniformity. In an embodiment, the individual time-series objects that make up the image may be processed as a group for similarity to other groups of time-series objects associated with a particular diagnosis or clinical condition. The Motion Picture of Physiologic Condition (MPPC) may, for example, include abnormal and/or perturbed components and in particular "Motion Pictures of Physiologic Failure" (MPPF) of the physiologic system and of exogenous forces relating to that system. Provided herein is a processing system and method for generating real-time MPPCs of healthcare signals and processing those images to timely detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate and then recognize motion pictures of physiologic failures and of the treatment applied in association with the failures.

Also provided herein is a processor and processing method for the automatic generation and/or analysis of the images of physiologic and/or clinical condition and the characterization and aggregation of the image components of complex dynamic systems, such as physiologic systems and medical care systems. The processing system may generate real-time MPPC of healthcare signals and processing those images to timely detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate and then recognize motion pictures of physiologic failures and of the treatment applied in association with the failures. According to one embodiment, a processor first renders parallel time-series from each of a plurality of sensors and testing sources, which are applied to broadly monitor the dynamic system for failure. In an example, a processor programmed with instructions for time series objectification of patient data detects patterns along the parallel times-series, converts these patterns into time series of discrete objects, then organizes these objects into discrete relational objects (such as binary objects, or relational binaries, derived of relational object pairs). The processor then organizes the relational binaries to render a unifying programmatic image of the physiologic system and the care provided. The processor then automatically recognizes objects in the image components and may be able to perform analysis on the images.

One embodiment may include a patient safety processor having a single processor or a combination of processors programmed to generate time series objects, a relational binaries, moving images, patient safety images, and/or patient safety visualizations. The patient safety processor outputs images of the patient's physiologic system and medical care. In an embodiment, the processor includes processing functions for time series objectification, relational binary processing, and an imaging processing. In an alternative embodiment, the patient safety processor combines multiple processing mechanisms (e.g., time series objectification, relational binary processing, and imaging processing) into a single matrix construction processor.

According to an embodiment, perturbations detected by the processor are converted to image components that may be used to generate a moving image. In an embodiment, an MPPC may be representative of a "motion picture of physiological failure" (MPPF) when a failure image becomes progressively more complete and recognizable by the processor as each additional failure image component is added. One embodiment may involve building a dynamic real-time image of disease, injury, and/or drug reactions, the care provided, and the expense associated with that care. The image is initially associated with initial image components including one or more minor perturbations, which may for example be caused by circulation of one or more toxic, acidic, and/or immunogenic material of endogenous or exogenous origin. At first these perturbations, such as toxins, inflammatory and/or thrombogenic mediators, may induce and/or cause only minor changes in cell permeability, ion flux, or hydrogen ion elevation, and trigger various minor physiologic perturbations and responses each of which may produce an image component. The measurements of various mediators, ions, biologic profiles, as well as standard blood tests, and the outputs of vital sign monitors may begin to vary as a function of these early physiologic perturbations and responses, and it is these variations that enlarge the group of image components from which the larger image is derived. Early in the process, each of these alterations in permeability, cell injury, mediator production, and physiologic perturbations, when considered in isolation, are often minor. However, collectively they may represent the early manifestations of a nascent and evolving moving image of a serious clinical condition.

According to one embodiment, each perturbation is programmatically organized to form an image component of the MPPC. Many of these detected images components may be isolated because they are related to a benign process, and the image may self-extinguish or may not develop into an image associated with a clinical condition involving intervention or an MPPC. Yet, as noted above, others may represent the first image components of an early moving image. Provided herein are systems and methods for the detection of the early image components of an evolving moving image to provide timely detection of physiologic failures before these failure progresses to shock (including, for example, hypovolemic, obstructive, septic, toxic, cardiogenic, hypoxic, and/or hypercarbic shock.) In one embodiment, it is advantageous to detect the early image components of the moving image before shock develops to improve the prognosis for the patient and to apply goal-directed therapy while clinical intervention is still beneficial.

According to one embodiment, a patient safety processor constructs a programmatic MPPC, which is used for dynamic, motion picture responsive, protocolization of care. This motion picture is comprehensive, including not only the events including a single or few parameters such as a the heart rate, but also other parameters that may include, for example: the slope and pattern of the heart rate, the slope and patterns of the systolic pressure variation, the slope and patterns respiration rate, the slope and patterns $SPO_2$, the slope and patterns ventilation-oximetry index, the slope and patterns drug and fluid infusion rate, the slope and patterns blood pressure, the slope and patterns of the Neutrophil count, and the slope and patterns of inflammatory and/or thrombotic markers, and various other blood, urine and/or exhaled gas test to name a few. The signals from all of these sources may be converted to time-series and may, for example, be physiologic signals, therapy signals, laboratory signals, or historical signals, which may be objectified, as by an objectification processor, to produce the discrete programmatic objects (events). According to one embodiment, the processor detects a first discrete event that includes a pattern or value of at least one medical signal, and a second discrete event that includes a second pattern or value of at least one medical signal, the processor then aggregates at least the first event and the second event to produce a first relational object, the processor further detects a third event that includes a pattern or value of at least one medical signal, and a fourth event that includes a second pattern or value of at least one medical signal, the processor then aggregates at least the third event and the fourth event to produce a second relational object. The first relational object and the second relational object are then aggregated to produce a first image component. Additional images are built accordingly and the image components are then aggregated according to the time of occurrence to derive the moving image and care.

In an example, the pulse related components of the typical motion picture of sepsis failure cascade would include occurrences such as early rise in heart rate, rise in pulse amplitude, and rise in slope of the pulse upstroke (as measured at the finger tip) in combination and typically proceeded by a brisk rise in inflammatory markers. In contrast the typical motion picture of occult hemorrhagic failure cascade (as for example due to heparin related retroperitoneal hemorrhage) would include occurrences of an early rise in heart rate, a fall in pulse amplitude, and a fall in slope of the pulse upstroke (as measured at the finger tip) and a rise in the respiratory related pulse pressure variation and a fall in hemoglobin. According to one embodiment, all of these occurrences along the image of an occult hemorrhagic failure cascade can all be derived from a multi wavelength pulse oximeter.

According to an embodiment, a relational binary processor is provided that divides detected variations into discrete alpha events and beta events, which are combined by the relational binary processor to construct the relational events which are termed relational binaries. These relational binaries are aggregated according to timing, frequency, and/or spatial relationship to construct images. These images are then further aggregated according to timing, frequency and/or spatial relationship to construct and progressively build MPPC (from which visual images or electronic representations may be derived as desired). These MPPC are often moving images of catastrophic cascading failures, thereby allowing more reliable detection to allow timely rescue of the patient.

The signals may be chemical or physiologic measurements, as provided by patient monitors, recorded in the electronic medical record, and/or may be biomarkers specifically ordered, either automatically by the processor or manually by the clinician to indicate the potential presence of the sepsis (as those, for example, disclosed in U.S. patent application Ser. Nos. 10/704,899, 11/647,689). The presence and/or concentration of such markers may be presented in the context of the MPPC with the timed positioning relative to the others parameters, which then allows the relevance of the biomarker to be much more readily identified. According to an embodiment, the temporal and relational pattern of inflammatory markers and temporal and relational patterns of contemporaneously measured or associated physiologic parameters are aggregated to produce a progressively enlarging MPPC of an evolving patient condition.

Therefore, to achieve the detection of various pre-shock states as well as earlier detection of failures, one embodiment detects early variations and aggregates them to provide an MPPC to dynamically present expanding failure cascades of pre-shock and shock states. This allows separation of expanding images from the smaller and less expansive image components having benign characteristics, and further allows separation of the images of minor isolated failures from failures that progress to generate an expanding MPPC heralding the potential for transition to one of the shock states. Each group of images as well as the complete MPPC and care may be analyzed for the purpose of assessing patient care in a hospital, a ward, or under the care of a given healthcare worker.

The occurrence of a large number of images indicating non cascading failures which self extinguish may be indicative of an unstable patient population or poor health care delivery. In the alternative, a large number of cascading failures are indicative of risk of injury. The MPPC and the images may be used to determine if that is due to the patient population or the quality of the care.

One embodiment detects failure cascades along with the determination of the specific fundamental perturbations, or treatments, or lack of treatments that occur early in a failure cascade. Specific fundamental failures are detected before they progresses to complex failures and particularly before they progresses to the pre-shock or shock state. Furthermore, the processor builds an image derived of the relational perturbations and treatments as the cascade expands. According to one embodiment, each time series is processed to separate expected events from unexpected events. The unexpected and/or abnormal events are then aggregated further to repetitively generate relational events, images and finally the MPPC which includes a motion picture of the cascade (if present) as well as the treatment applied in association with the cascade. This MPPC is further processed to allow the detection of the probable cause or causes of the occurrence of the moving failure images well as the images of the MPPC as it evolves thereby allowing detection of the nature and cause of the failure cascade.

As noted above according to one embodiment, an analysis is provided wherein the fundamental components of the analytic process include a basic relational variable that includes a plurality of events. In a contemplated embodiment, the basic relational variable is that includes two events (a relational pair) and this is called a relational binary. In one embodiment, the relational binaries are initially selected by the users as from a menu (or by a drag and drop interface) of relational binaries and/or of events from which the user builds the desired object binaries the binaries are then used as by drag and drop to build the definition of images for detection. This may be performed by, for example, by national or regional expert groups, or by specific departments in a hospital, or by an individual physician to provide custom management. This may also be automatically performed by the processor (as, for example, through the investigation of a large number of historical data sets that have been comprehensively analyzed and categorized according to outcomes. The objectified time series matrix and/or the MPPC may be may be outputted in various interactive, hierarchical, and relational formats for review and automatic or manual adjustment. The MPPC may detect a wide range of failures, such as physiologic failures, treatment occurrence failures indicating the absence of expected treatment in relation to a given perturbation, testing occurrence failures indicating the absence of expected testing in relation to a given perturbation, treatment response failures indicating the absence of the expected correction of perturbation or the occurrence of a new potentially complicating perturbation in relation to a given treatment and/or dose.

The processor combines the complex data of the electronic medical record into a single motion picture of perturbations, treatments, physiologic responses, diagnostic testing, recoveries, diagnoses, missing data, patient locations, and/or other datasets. Dynamic images are generated of relational variations of a set of time series associated with a complex system to generate a real time motion picture of a failure of the system and/or of forces applied to the system. According to one embodiment, the patient safety processor automatically outputs a unified timeline, for example, derived of detected images of a given type. According to another embodiment, the processor, upon detecting a failure cascade, may present and highlight the evolving MPPC in real time on an outputted display of an image diagram for the physician to review. The portion of the motion picture, which has already been completed, may be reviewed backward and forward to review in a single summary snap shot view.

Many physiologic failures such as, for example septic shock, pulmonary embolism, congestive heart failure, respiratory arrest due to narcotics in the presence of sleep apnea, thrombotic thrombocytopenia purpura (TTP), hemorrhage due to anticoagulation, respiratory failure due to bronchospasm, and adult respiratory distress syndrome, but not limited to these clinical conditions, begin with one or two non-specific perturbation(s). Physiologic failure is commonly a relational expansion, often beginning with a fundamental physiologic perturbation at a single focal point in time. In fact, this initial perturbation is often completely masked once the cascade has progressed past a certain point. In such cases, testing or monitoring for the single perturbation may not be useful for making a diagnosis. In many cascading clinical conditions, the first perturbation(s) of the cascade may often only be detected in retrospect after the cascade has further progressed when the first perturbation(s) is no longer present. This provides a basis for optimizing the detection of the first point(s) by real-time imaging of the cascade as it develops and then examining the image to determine the first perturbation(s).

While a pattern of a single time series provides a larger image of a dynamic process than a single value or range, such a pattern is still only a tiny image fragment of the process. The determination of thresholds and even the detection of various patterns of perturbations include incomplete analysis, which will inevitably allow an unacceptable rate of progression to catastrophic failure. Even in situations wherein a measurement or test may seem definitive as a stand-alone test, action or conclusions based on a single value (or an average of a plurality of values) will have a reasonable probability of being incorrect. Consider, for example, a single measured spot $SPO_2$ value of 94. This value is largely meaningless without knowing if the $SPO_2$ is rising, falling, or cycling. Yet this infinitesimal image fragment of a patient's complex physiologic system is used every day in hospitals to determine care. Furthermore, even if the pattern of the $SPO_2$ is known (for example the $SPO_2$ has been stable at about 94 for at least 12 hours) this is an incomplete image, which is largely useless and, in fact, a potentially misleading piece of information. Without knowing the relational pattern of the minute ventilation during the related time interval of the measured $SPO_2$ pattern, the healthcare worker may be lulled into a false sense of security even as the patient is dying of septic shock or heart failure. Furthermore, an alarm or interpretive output which is based on a programmatic image of both the patterns of both the $SPO_2$ and the related minute ventilation without additional relational elements of the image, such as, for example, the associated pattern of the white blood cell count, temperature, pulse, blood pressure, microbiologic values, and medications will be incomplete leaving too much synthesis for the healthcare worker. In another example, consider the detection of a pattern of a sustained rise in pulse or respiration rate. Each such pattern represents a tiny fragment of the present physiologic state and each pattern may be benign or alternatively may be an early image component of a much larger dynamic process of failure often associated with an evolving failure cascade. The difference between a benign or pathologic rise in pulse or respiration rate cannot be determined with this tiny image alone and often cannot even be known at the time of the onset of the rise. Therefore a tree diagram protocol with a branch based on a rising pulse or rising respiration rate adds a great degree of programmatic complexity with a high risk that the protocol will precede down the wrong pathway. An incomplete analysis of the physiologic system will often cause the healthcare worker to generate a large amount of investigation, testing, analysis and evaluation that is not necessary and therefore increases the cost of overall care. Further, these false paths of treatment and evaluation may distract the care worker from the determining the actual operative failure modes.

Prior to shock, a patient's physiologic system is perturbed by both disease and treatment. A given treatment provided to correct a perturbation might reduce the perturbation, have no effect on the perturbation, exacerbate the perturbation, cause another perturbation and/or make another perturbation worse or better. To determine which effect a treatment is having and to assure that this determination of treatment effect is complete, it is necessary to collect and, just as importantly, as provided by one embodiment, organize and analyze large amounts of relational data in a timely manner.

Another problem is that, within present hospital systems the healthcare worker is forced to do a great deal of archeology (digging, isolating, identifying, etc.) before synthesis may be effectively completed. For this reason, the synthesis of information by the healthcare worker is often not executed in a manner, which allows immediate searching, filtering, re-analysis, etc. This friction combined with the typical workload of healthcare workers limits the number and range of high-level scenarios, which may be investigated. Also the healthcare worker may, because of lack of available organized data and time, execute decisions without a complete set of synthesized information and worse, may not realize that this is the case.

For these reasons, even with conventional electronic medical record embedded protocols, patients remain subject to a range of failures across a broad range of failure modes based on the complexity of their individual condition and the complexity of the environment facing the care giver. In fact, because failures often overlap, one protocol may reduce the risk of one failure while increasing the risk of another. For example, oxygen given to treat hypoxemia under one protocol may delay the detection of pulmonary embolism by stabilizing the $SPO_2$ and hiding the early signs of impending shock from the healthcare worker.

Because so many confounding and overlapping occurrences can be present, the time series objectification processor, the relational binary processor and imaging processor execute multiple iterations of analysis and refinement. In one embodiment this analysis would begin with a phase one execution in which each processor in order (time series, relational binary, and imaging) operates on the specified set of time series inputs storing the interim analysis results in memory and/or in the patient safety image database. After this has been completed, the patient safety processor may execute phase two preferably in the same order providing each processor with the original time series data as well as the full analysis from the previous phase(s). This second phase may refine the analysis in terms of the first phase analysis. This process may contain as many phases as required for complete refinement of the analysis.

The PHM monitor 206 comprises a processing system and method which analyzes the complex and voluminous medical data sets which comprise a PHM. The analysis comprises detection, identification, quantification, and tracking of cascading perturbations, the forces inducing the cascading perturbations, as well as triggering events (such as a surgical procedure) which may have induced the forces. The processor also searches for the "apical force" 700 of FIG. 7 which comprises a force sufficient to generate a severe distortion of the PHM (for example by inducing a force cascade (which may be a force polyquaternary cascade) within the PHM. The apical force 700 or forces (for example invasion of the human by bacteria) generally precedes the force cascade (and is positioned in the matrix at the apex of the force cascade). The apical force 700 is often a diagnosis such as "group A streptococcal bacteremia". In one embodiment, the apical force 700 is a relative concept specific to a perspective selected by the viewer. For example, a user may be interested in the apical force 700 within a clinical space.

The analysis further comprises detection, identification, quantification, and tracking of cascading recoveries, and the forces inducing cascading recoveries. The PHM monitor analyzes the data from the PHM to generate outputs which may comprise dynamic motion images of force cascades over time. The PHM monitor may generate images which present the relational complexities of the force cascades along the PHM in dynamic formats which are readily understood, such as a color radar weather-map format.

A PHM may be comprised of any suitable amount of the medical data and/or related medical expense data available for a given patient from the onset of data collection (before or at the time of birth) and forward. The entire matrix back to its point of origin may be constructed and analyzed by the PHM monitor for distortions and the PHM may be viewable in relation to time as a time-lapsed motion image through the use of a PHM visualization processor which generates motion images of the PHM in a range of dynamic formats including, for example a color weather radar format as for example described in the co-filed application, "Patient storm Tracker and Visualization Processor".

Each individual, or the individual's parents or guardian, may possess their own PHM as well as the PHMs of their children or of individuals under their guardianship. This will give each individual, parent, or guardian, much more control over their healthcare. Individuals may store their own updatable PHMs, either partially or as a whole, on memory storage device such as flash memory card which may, for example, be integrated with their driver's license or another storage device such as a hard drive, or a secure access cloud site. The PHM generator may be programmed to automatically update a PHM on a storage device when the device is connected with the PHM generator.

The individual PHM of each patient in a healthcare system may be stored in the cloud where each may be updated when new data is available. The healthcare system may deploy one or more PHM monitors to monitor each of the PHMs in the cloud whether the client is in the hospital or not. An individual may choose to have the raw data (which is preferably stored as part of the PHM), the PHM itself, and/or the output of the PHM monitor reviewed by an expert physician on a periodic basis and to update the PHM or correct the configuration with her or his expert input.

The time-lapsed representations of a personal PHM may be animated in a range of alternative formats and viewed on a device such as a smart phone, iPad, Galaxy tablet, or Surface tablet to name a few. At least one animation is preferably readily understandable by individuals without medical training. Individuals may view their own PHMs or those of their children from the storage site using a PHM visualizer. PHMs may be updated while a patient is in the hospital or emergency room as by secure smart phone, password protected Wi-Fi or other secure transmission, so that the individual, parents, or other approved family members are updated in a manner wherein they may readily seek alternative PHM review, an alternative PHM monitor, or expert who may be remote for the hospital.

According to one aspect of some embodiments, although the PHM may function as a comprehensive medical data repository for each individual, it is actually a dynamic, growing, and highly portable, parallel representation of the dynamic state of health and/or disease of the represented individual within the limitations of the available data Like the individual, the PHM may be continuously or periodically updated and monitored to determine the PHM's state of "health".

In one embodiment, the PHM processor 200 monitors the parallel patient construct (the PHM). Both the healthcare workers and the PHM may monitor the actual biologic patient, asking questions, applying tests, and physical evaluations, updating the PHM and the healthcare worker. In addition, both the PHM processor 200 and the healthcare workers from Institution A 208 and Institution B 210, among others, monitor each other to optimize quantity, timeliness, and efficiency of care. The PHM, upon identifying a distortion comprised of abnormal physical findings, test result, and/or historical finding, the PHM may identify linkages and images which comprise primers of the image of the distortion and upon the detection of one or more primers, generate one or more questions for the patient, or ask the healthcare worker to examine a physical portion of the patient, the answers and/or results to which may help improve the image in the PHM. At the discretion of the healthcare worker or when the worker is not available, the PHM may ask the patient directly in text or voice or the PHM may offer the questions to the healthcare worker so that he or she may ask them. In this way the PHM processor 200 uses dynamic image primers of specific distortions (or the lack thereof) to focus or expand the medical history and physical as well as clinical testing.

Figure 5:
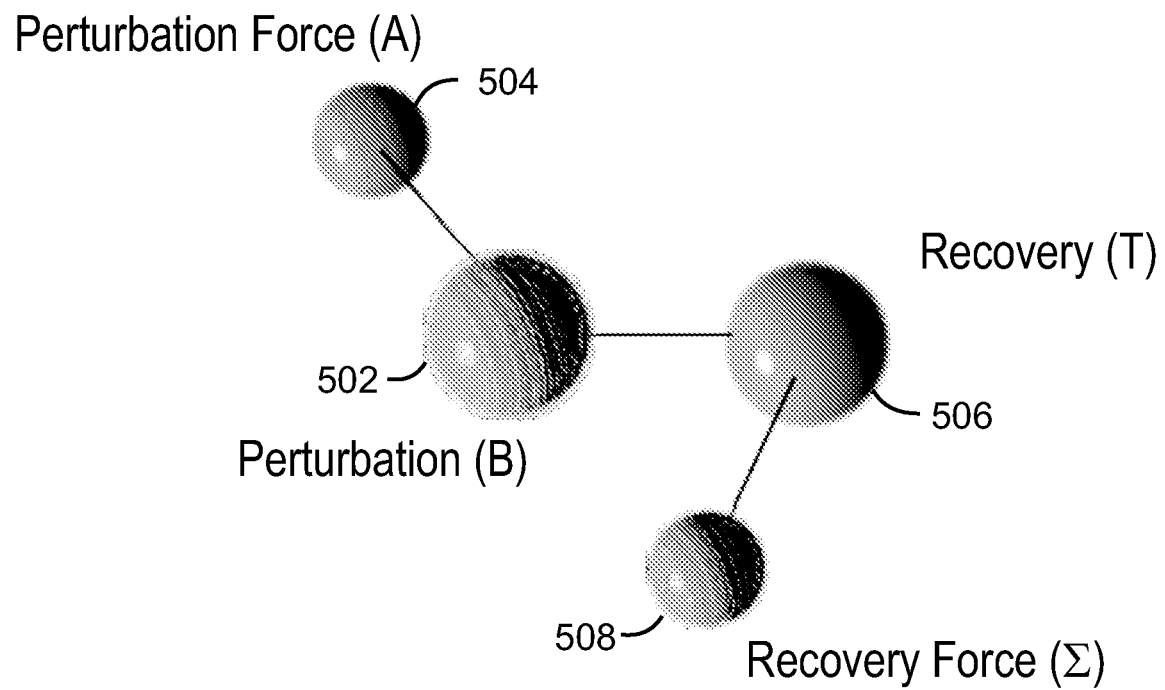
FIG. 5 depicts a single quaternary.

FIGS. 4 and 5 shows examples of basic "building blocks" comprised of perturbations and matched recovery, with matching forces, which define the fundamental building components (which may be objects) of the PHM. In one embodiment as shown in FIG. 5, the PHM processor 200 detects and link a set of at least 4 components of a distortion quaternary comprising, a perturbation 502, the matching perturbation force 504 (which is capable of inducing, and may have induced that specific perturbation), a recovery 506 (from the perturbation or in response to the perturbation), and the matching recovery force 508 (which is capable of inducing and may have induced the recovery). In one embodiment of the PHM, all of these components are converted objects that are linked in the timed sequence of their occurrence with the distortion itself being comprised of a solved or unsolved quaternary or polyquaternary. In one embodiment, each distortion is comprised of only one quaternary or polyquaternary and when two quaternary or polyquaternary are present they are either linked (and this link has not been detected) or there are two distortions. The processor 200 seeks a common link for (or a link between) the apical forces (or another force or perturbation) of each polyquaternary or seeks common exogenous trigger force for each.

Figure 6:
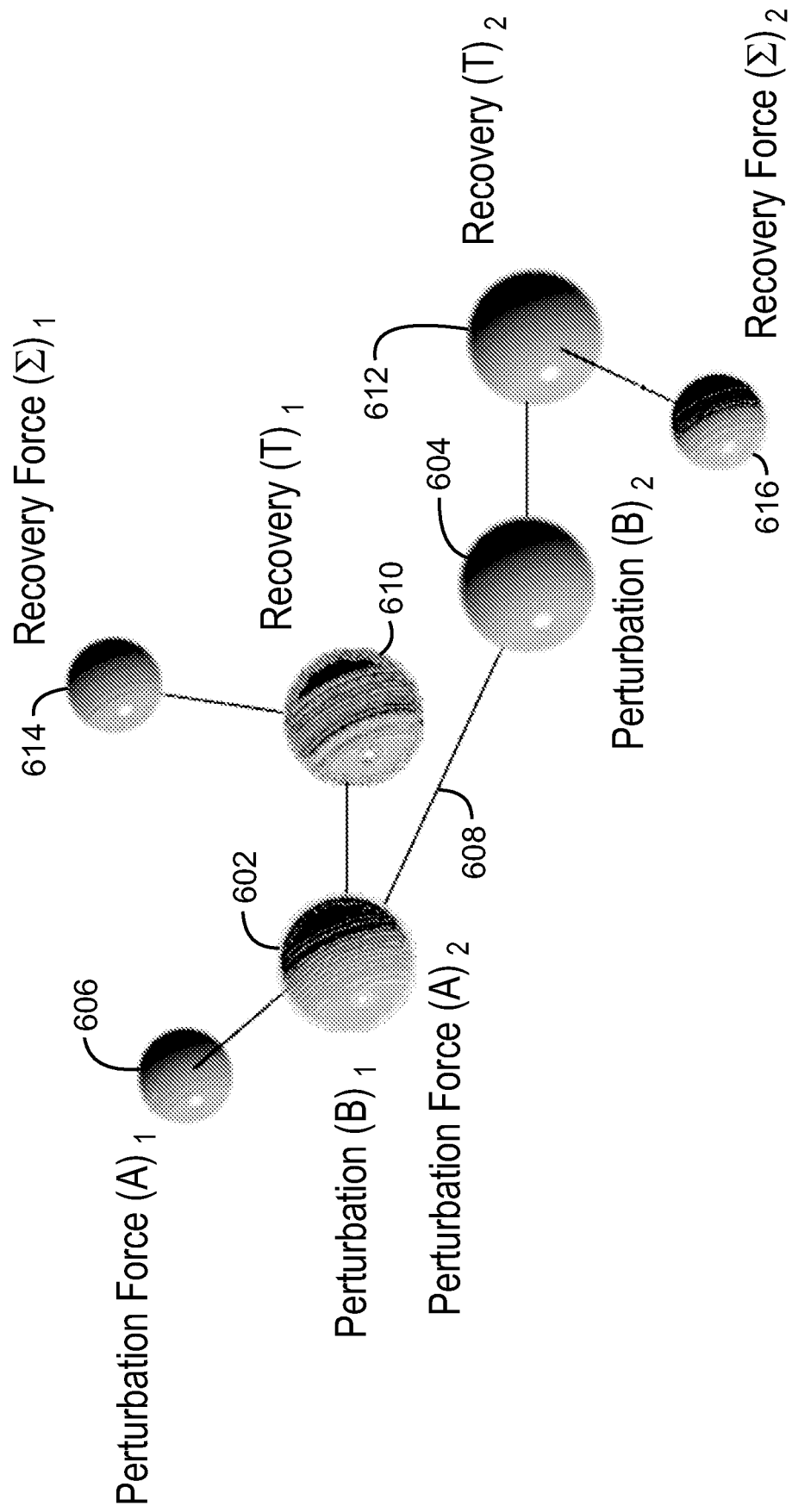
FIG. 6 depicts two linked quaternaries wherein the perturbation of the first quaternary is the perturbation force of the second quaternary.

The PHM generator may use combinations of each of these objects and particular the combination of all four of these objects to build or "grow" the distortion by linking additional groups of these objects as shown in FIG. 6. As shown in FIG. 6, the perturbation of one grouping may be the perturbation force of a second grouping as these are detected and linked the processor 200 generates a force cascade of perturbations and forces which mirrors those operative in the patient. As will be discussed there will be gaps in the distortion but one goal is to build the image sufficiently to detect the primary cause of the distortion such as a "force-cascade precipitating force", which is generally an apical force 700 (designated as such as it generally exists (or existed) near the origin (the apex) of the expanding force cascade which comprises the distortion as shown in FIG. 7.

Figure 7:
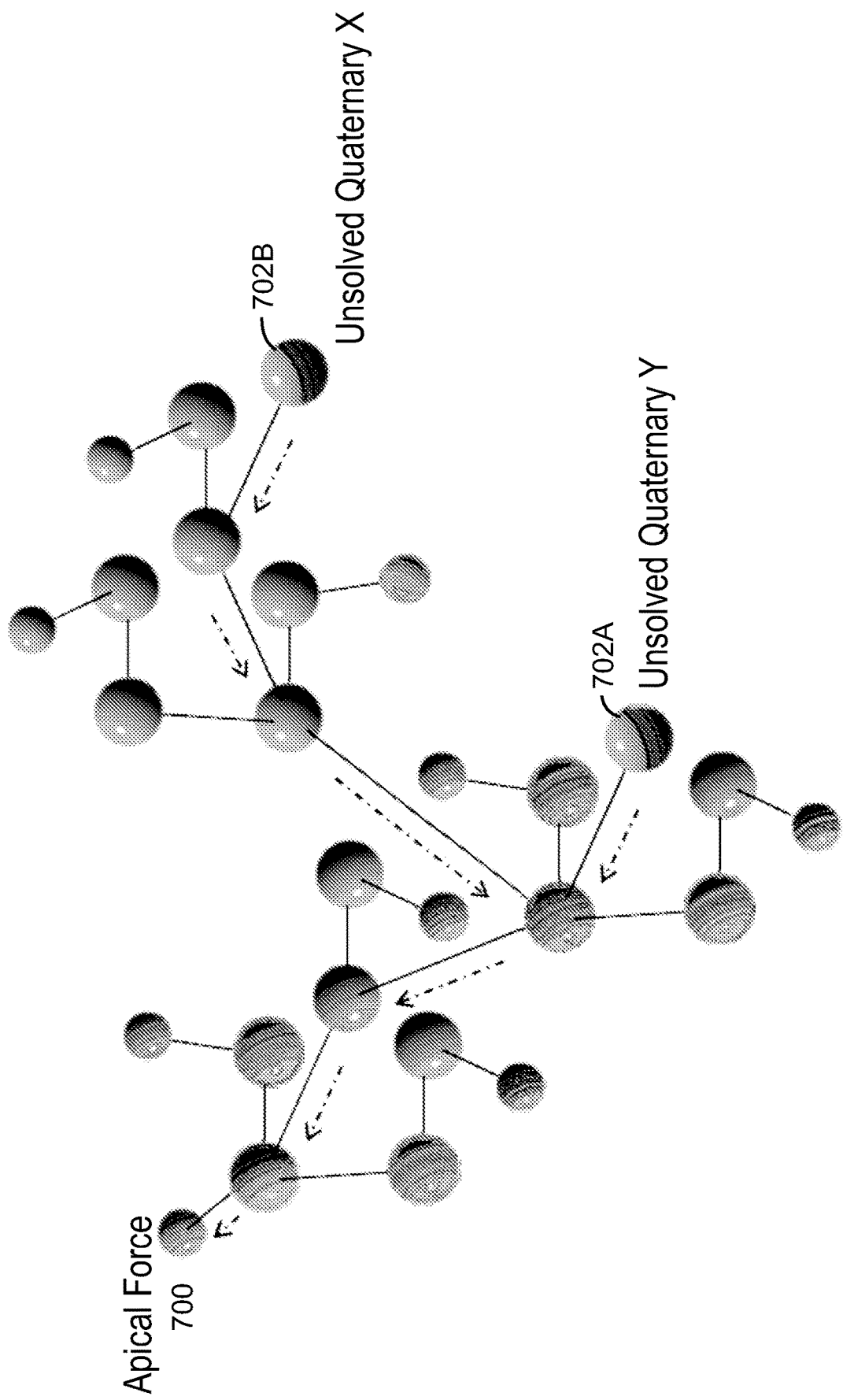
FIG. 7 depicts a polyquaternary distortion with many linked quaternaries including 2 unsolved quaternaries and a single identified apical force comprising an image of causation.

FIGS. 6 and 7 show linked polyquaternaries. The example illustrated in FIG. 6 includes perturbation B1 602, perturbation B2 604, perturbation force A1 606, perturbation force A2 608, recovery T1 610, recovery T2 612, recovery force Sigma1 614, and recovery force Sigma2 616. However, typically, during early distortions in the PHM due to an unknown but dangerous process, only perturbations are initially evident along the distortion and the polyquaternary 600, which will in the future, when solved, identify, quantify, and define the distortion is incomplete. In an example, it is typical of in early sepsis before the diagnosis is made by the clinician or processor 200 for the distortion of the PHM to comprise only perturbations although many of these will be compensatory perturbations which mitigate movement of critical densities away from normal values. In other words, in early sepsis the FIGS. 6 and 7 would be comprised almost entirely of perturbations.

One of the purposes of the PHM processor 200 is to solve the polyquaternary as soon as reasonably possible since upon the solution of the polyquaternary the processor 200 may be able to render a diagnosis, quantify the condition, project a "near worst case" path of at least part of the distortion, and provide direction for treatment or treatment modification. In many cases the processor 200 may solve the polyquaternary with only perturbations, inserting the forces, and especially the apical force when the processor 200 has solved the polyquaternary and determined its identity. The completed distortion is generated when the polyquaternary has been solved although there may be missing forces and particularly recovery forces if the polyquaternary has not yet extinguished along the PHM. Many of the cascading forces may be completed by the processor 200 when the apical perturbation force is solved and the diagnosis made. The time pattern of the recovery force may be used by the processor 200 to characterize the recovery patterns of the polyquaternary distortion.

Along the polyquaternary, relational timing of the apical perturbation force, treatment potential triggers, treatment, identification and the durations, including of the expansion and contraction portions of the polyquaternary are all defined to determine quality of care. The polyquaternary is displayed, for example in relation to time, to illustrate the timing relationships.

The PHM monitor is programmed to detect dynamic distortions in the PHM, and generate processing decisions. Collectively a unified PHM processor 200 may perform all of these tasks. The PHM processor 200 may link two of the four objects such as a perturbation objects and the matching perturbation force object, or the recovery and the matching recovery force, or the perturbation and the matching recovery from or in response to the perturbation, or the perturbation force and the recovery force which induced the recovery from the perturbation induced by the perturbation force, or the perturbation force and the recovery from the perturbation, or the perturbation and the recovery force which induced the recovery from the perturbation, as well as three or all four combined components as decision points (such as the ordering of additional testing), or decision components, and also to link to other events or combined components.

In one embodiment, (as shown in FIG. 5) the PHM processor 200 links the quaternary and then uses the quaternary as a "primer" to build a polyquaternary. However, as noted, the processor 200 may only have one or more of the perturbation objects available to use as the primer. The PHM processor 200 may be programmed to, upon detection of the primer, complete the image by linking available data or to order additional testing to complete the image.

The PHM processor 200 may combine a perturbation object with a perturbation force object to generate a "perturbation force binary" object. The PHM processor 200 also may combine a recovery object with a matching recovery force object to generate a "recovery force binary" object. These two binaries may be combined by the PHM processor 200 to generate the "perturbation-recovery force quaternary" of FIG. 4. These force binary objects and force quaternaries may be linked to other binaries and quaternaries to build highly complex, time dimensioned images. The PHM processor 200 may then construct very large and highly complex force cascades, such as sepsis force cascades of; triggering exogenous perturbation forces, (such as a surgical procedure), endogenous perturbation forces, perturbations, and exogenous recovery forces (such as an antibiotic or surgical intervention), and endogenous recovery forces, using basic binaries, the quaternaries, and/or individual events or forces. The PHM processor 200 may also create and use trinaries, or other basic building objects which combine multiple objects. The PHM processor 200 may then generate motion images of the force cascades of objects comprised of perturbations, recoveries, forces, binaries, quaternaries, diquaternaries and polyquaternaries, which may comprise a distortion or set of distortions of the PHM.

The processor 200 may be programmed to provide processing systems and methods, which analyze dynamic pathophysiologic force cascades of perturbation of the densities of biologic particles and recoveries of the densities of biologic particles (and particularly force cascades of perturbation and recoveries of densities of biologic particles induced by sepsis), along with associated individual, relational and force cascades of the forces inducing the perturbation and the forces inducing the recoveries of the densities, and for presenting the force cascades of the perturbation and recoveries as well as the perturbation forces and recovery forces in a motion picture responsive to or indicative of force cascades of perturbation, which may be linked to force cascades of perturbation inducing forces, which may be linked to force cascades of recoveries, and which may be linked to force cascades of recovery inducing forces.

The processor 200 may be programmed to identify those perturbations or recoveries for which the processor 200 does not identify the perturbation inducing force and/or the recovery inducing force. In one embodiment the processor 200 is programmed to identify those force cascades of perturbation and/or recoveries for which the processor 200 does not identify the force cascades of perturbation inducing forces and/or force cascades of recovery inducing forces.

The processor 200 may be programmed to identify those perturbation inducing forces and/or the recovery inducing forces for which the processor 200 does not identify the perturbation and/or the recovery which the forces are expected to induce. The processor 200 may be programmed to identify those force cascades of perturbation inducing forces and/or force cascades of recovery inducing forces for which the processor 200 does not identify the force cascades of perturbation and/or the force cascades recovery which the forces are expected to induce.

The processor 200 may be programmed to analyze (which comprises for example, detection, identification, quantification, and/or tracking) the individual perturbations and/or force cascades of the individual perturbations and to analyze the individual perturbation inducing forces which induced the individual perturbations and to link and/or link in a output or display, the individual perturbations which are induced by the force and the force cascades which are induced by the force or induced by a force cascade of forces.

The processor 200 may be programmed to analyze and link individual perturbation inducing forces, to individual perturbations, and to individual recovery inducing forces and to individual recoveries. The processor 200 may be programmed to link the individual recoveries to the individual perturbations which are reversed or corrected by the individual recoveries, and to analyze at least one force cascade of perturbations and at least one force cascades of perturbation forces and at least one force cascade of recoveries and at least one force cascade of recovery forces.

The processor 200 may be programmed to generate a linkage chain or a temporal cluster of linkages and to link a perturbation and/or a force cascade of perturbations to a perturbation inducing force or a force cascade of perturbation inducing forces, and further to link a recovery and/or a force cascade of recoveries, which reverses or corrects the perturbation and/or force cascades of perturbations, to the force or cascades of forces inducing the recovery and/or force cascades of recoveries, link the perturbation and/or force cascades of perturbations to the recovery and or force cascades of recoveries, link the perturbation inducing force and or force cascades of perturbation inducing forces, to the recovery inducing force and/or force cascades of recovery inducing forces. The processor 200 may be further programmed to link other events, such as for example exogenous actions and/or genetic information to at least a portion of the linked chain or spatial and/or temporal cluster of linkages.

The processor 200 may be programmed to analyze a sepsis force cascade, its onset (which may comprise the onset of early inflammatory augmentation), its evolution, its expansion, its peak, and its recovery in relation to endogenous forces, such as perturbations in biologic particle densities or organ dysfunction, as well as exogenous forces (such as exogenous actions) such as surgery, central line placement, initiation of intravenous nutrition, antibiotics, to name a few. The processor 200 may be programmed to link the force cascades to other factors or objects such as the healthcare worker, hospital location, cost of care, to name a few.

Figure 22:
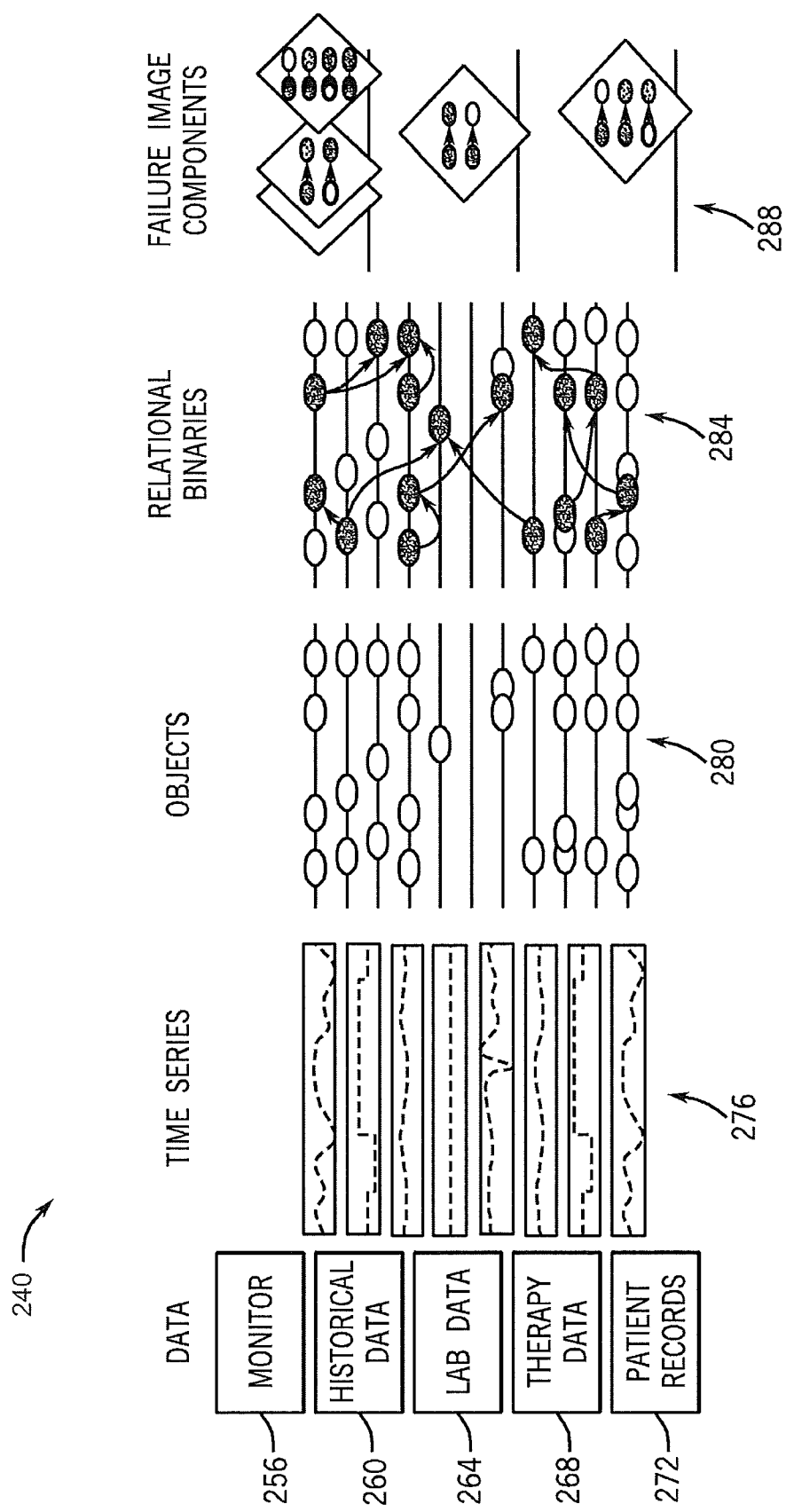
FIG. 22 is a diagram depicting the levels of analysis in accordance with an example of an embodiment.

FIG. 22 depicts an overview of the flow of analysis for modeling complex patient physiological condition in one embodiment. A wide range sources may provide inputs to the modeling. For example, patient monitors 256, patient records 272, historical patient data 260, lab results 264 and therapy data 268 may provide the raw data input into the analysis stream. These inputs are converted to a set of parallel time series 276. Patterns and threshold violations along this plurality of parallel time series identified, coalesced, synthesized and organized into discrete objects forming object stream s 280 within each channel. These discrete objects are analyzed to identify known relational patterns into instances of relational binaries 284. In one embodiment, expert systems then further refine the analysis by organizing and synthesizing these relational binaries into a set of failure images 288, which as an aggregate whole make up a unified programmatic image of the complex and dynamic state of a patient and/or a patient population.

Figure 23A:
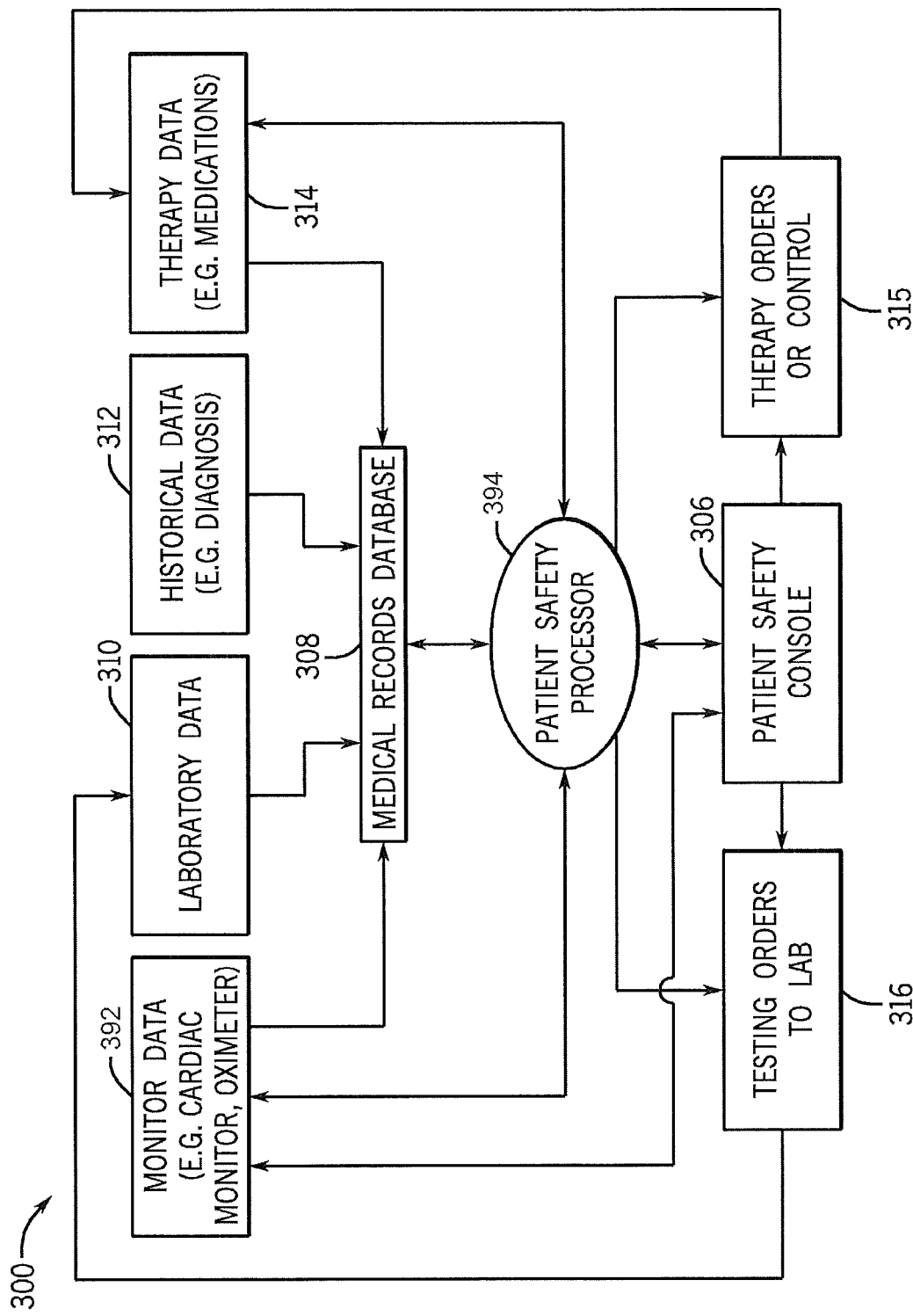
FIG. 23A is a data flow diagram in accordance with an example of an embodiment.
Figure 23B:
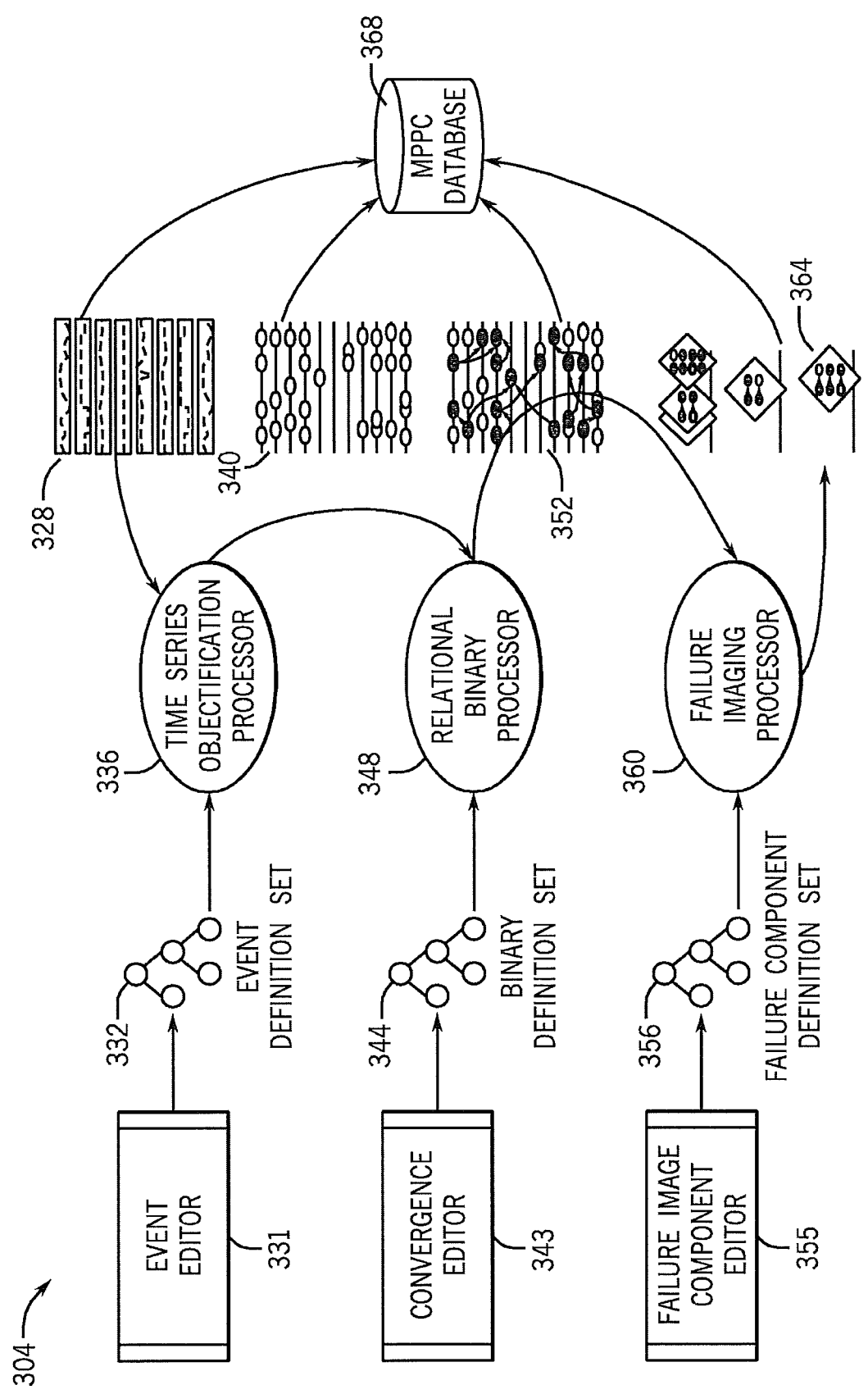
FIG. 23B is a diagram of an example of a system in accordance with an example of an embodiment.
Figure 23C:
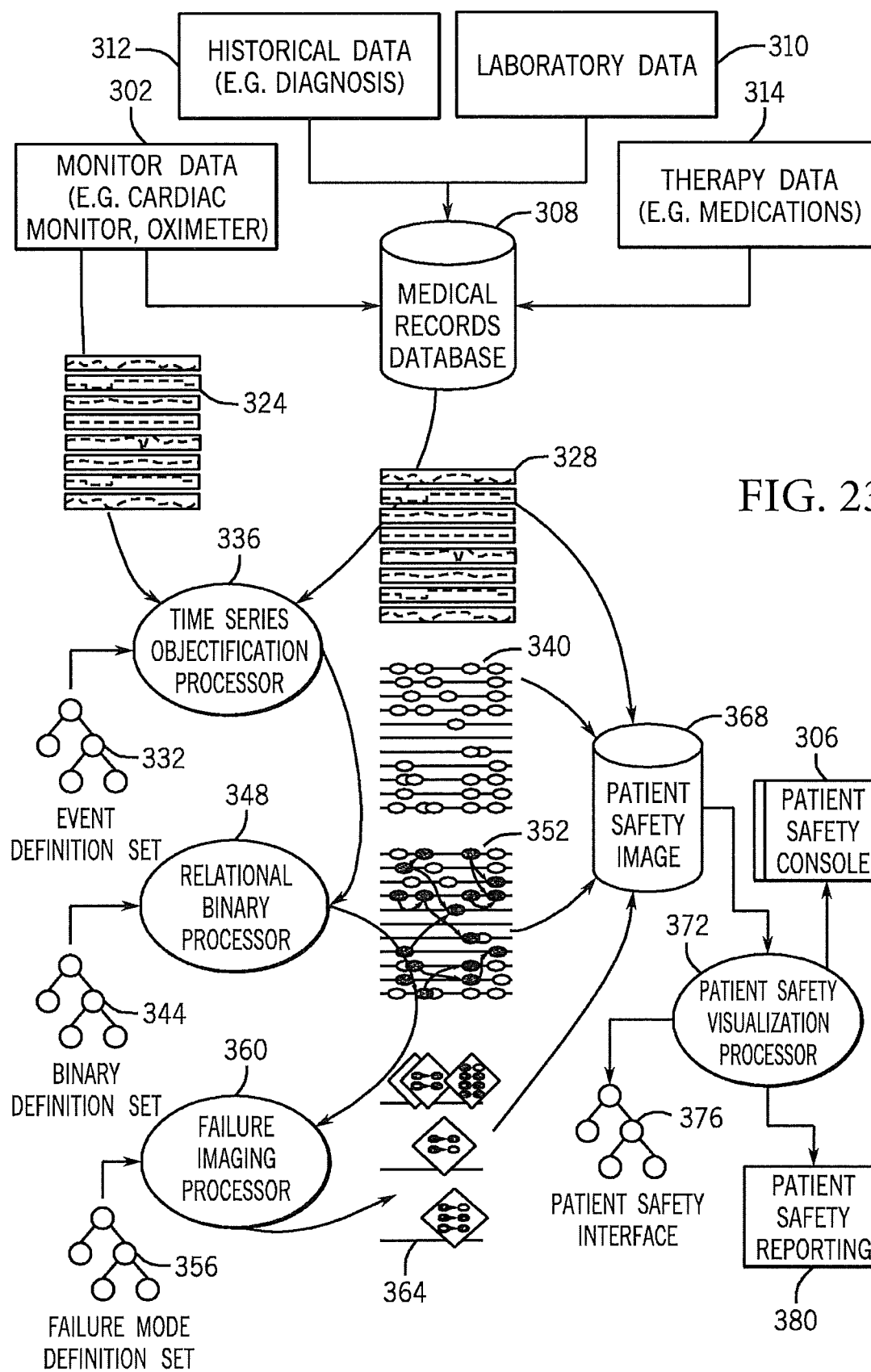
FIG. 23C is a data and action flow diagram in accordance with an example of an embodiment.

FIG. 22 depicts the flow of analysis 240 from raw data to the aggregate of images, while FIG. 23A, FIG. 23B, and FIG. 23C include some of the data stores, data flow, processors and output mechanisms within the exemplary embodiment. FIG. 23A depicts another data flow of one embodiment. The data management system 300 includes a monitor 392, a patient safety processor 394 that may include, for example, time series objectification processor 336, relational binary processor 348, and failure imaging processor 360. Alternatively, processors 336, 348, and 360 or instructions for performing the processing steps of time series objectification, relational binary processing, and/or failure image processing may be located on one or more additional processing components in communication with processor 394 that are part of the system 300. The processor 394 is adapted to provide output of the analysis to a device 306, which provides an interface for a healthcare worker. The data flow involves inputs from a wide range of sources (392, 394, 308, 310, 312, 314). As shown, the inputs may be sent to a processor 394 that may direct further action for the patient, including testing orders 316, indicators to the healthcare provider that may be displayed on a console or device 306, and therapy orders 315. Accordingly, the healthcare worker may use the device 306 to control and oversee the entire hospitalization process. In one exemplary embodiment, the processor 394 may be used to drive the device 306. The processor 394 may be adapted to constantly process all of the real-time data of all of the patients regardless of the status of the viewing console and to automatically send testing orders 316 and/or therapy orders 315 based on the analysis of the images derived from the processor 394, as will be discussed.

The data management system 300 may include one or more processor-based components, such as general purpose or application-specific computers. In addition to the processor-based components, the data management system 300 may include various memory and/or storage components including magnetic and optical mass storage devices and/or internal memory, such as RAM chips. The memory and/or storage components may be used for storing programs and routines for performing the techniques described herein that are executed by the processor 394 or by associated components of the data management system 300. Alternatively, the programs and routines may be stored on a computer accessible storage medium and/or memory remote from the data management system 300 but accessible by network and/or communication interfaces present on the computer.

The data management system 300 may also include various input/output (I/O) interfaces, as well as various network or communication interfaces. The various I/O interfaces may allow communication with user interface devices, such as a display, keyboard, mouse, and printer that may be used for viewing and inputting configuration information and/or for operating the system 300. The various network and communication interfaces may allow connection to both local and wide area intranets and storage networks as well as the Internet. The various I/O and communication interfaces may utilize wires, lines, or suitable wireless interfaces, as appropriate or desired.

In one embodiment, the device 306 is turned on as for continuous viewing (with a notification) by the processor 394 when images are indicative of a significant potential failure and/or cascade process or at a point wherein the patient's risk class exceeds a threshold value. The risk class may, for example, be derived as a function of a calculated instability index or a detected instability index pattern and/or detected failures. The instability index may be, for example, a confidence metric correlated with a matched image. For example, when an MPPC has a high likelihood of being associated with a serious condition, the instability index may be high. The instability index may be a numeric index, a color or graphic indicator, and/or an audio or text message.

In accordance with an embodiment, the device 306 includes an interactive screen displaying items, such as one or more working diagnoses, differential diagnosis, parameters derived from patients including laboratory parameters, monitored parameters, and subjective parameters (e.g., sedation scale, confusion scale, or pain scale) or the like. In an embodiment, the term "parameter" herein may refer to an absolute or relative data point or set, a pattern, or a deviation, a range of such data points or sets, a pattern of such data, a relationship along a single set of data and/or or between a plurality of sets of data, and/or patterns of data. The data may be an objective data type or subjective data type and may be directly and/or indirectly derived or historical in origin. In addition various outputs from the failure imaging processor 360 (FIG. 23B) may be displayed. According to on embodiment, the processor 394 may provide data for display present on the device 306 or through a report (either electronic or paper) or within an electronic representation that may provide an interface to external systems.

The data management system 300 further includes a medical records database 308 including laboratory data 310, historical data (e.g., diagnosis) 312 and therapy data (e.g., medications) 314. The medical records database 308 is coupled to the processor 394 and to the monitor 392 so that those systems may have access the data stored in the medical records database 308. The processor 394 may include a component or direct link to the centralized patient medical record, which contains real time data and receives data input from all hospital sources. Thus, a database containing substantially all of the components relating to the patient available to the hospital may be directly accessible to the processor 394 in real time to allow the embedded relational processor render relational binaries, and construct and detect failure image components which include these data from varied sources.

In accordance with an embodiment, the processor 394 is adapted to comprehensively engage the medical records database 308. As discussed further below, the processor 394 may be programmed to provide for formal, automatic simultaneous engagement, of physiologic failure image components, medication failure image components, testing failure image components, aggregate failure image components as derived from the relational processor and to render them in a timeline for viewing.

The processor 394 may be adapted to provide an immediate review of all failure image components and to take action based on the detection of specific failure image components. The processor 394 may be capable of responding faster and more reliably than the healthcare worker because it may be adapted to constantly monitor the evolving failure image components form the earliest onset of the first divergent binary. The processor 394 may therefore detect failure image component cascades, which originate from single divergent binaries, which might easily be undetected by the healthcare worker until it is too late. The processor 394 may also be programmed to alarm on divergent or null binaries upon which no action has been taken or upon which the action has not corrected the evolving divergent binary or failure image component. For example, in a scenario in which the processor 394 has been updated by the nurse that a blood culture has been obtained, the presence of a null binary may be generated indicating testing failure image component if after a pre-selected time the result is not available to the processor 394 whereas the presence of a divergent binary indicative of a physiologic failure image component may be detected if the culture is positive. If testing failure image component is detected the processor 394 notifies the lab of the apparent delay. The notification is an alpha event and a receipt response to that notification is a true beta event. Therefore the failure of the lab to indicate receipt may cause the occurrence of a divergent binary, which may trigger the notification of the nurse in the same manner until a convergent binary concludes the sequence. If on the other hand, a physiologic failure image component is detected (the culture is positive), the processor 394 notifies the nurse again in the same binary generating fashion.

While a positive blood culture is the beta event of the culture testing binary, it is the alpha event for another group of testing binaries such that the initial divergent testing binary may cause the processor to assure acquisition of a complete blood count, a comprehensive metabolic profile, increased frequency of blood pressure and pulse measurements, ventilation indexing oximetry and other testing as programmed into the processor 394 in response to the specific divergent binary detected (in this case a positive blood culture). These new testing binaries may generate unexpected beta events (such as a low blood pressure, a high pulse, or high ventilation to oximetry index) and these beta events may thereby define a new set of divergent physiologic binaries. This new set of divergent binaries (in aggregation) may be sufficient to meet the pre-selected criteria of an aggregate failure image component suggestive of early septic shock, which diagnostic consideration now includes an alpha event to a plurality of new binaries which have been programmed into the processor to assure timely and proper monitoring, timely proper patient location, and timely proper diagnostic testing, and timely and proper intervention in the event of the detection of this type of aggregate failure image component. In addition, the beta events of the divergent physiologic binaries which included the aggregate failure image component now become alpha events for new physiologic binaries wherein the beta event of each of the new binaries includes the return of each these values back to a normal range within a pre-selected time period (thereby assuring, that the aggregate failure image component is corrected timely, if possible). In additional, the positive blood culture is also the alpha event for a treatment binary such that the processor 394 may be expecting to see the correct antibiotic in response to positive blood culture administered within a pre-selected time interval. If this does not occur a divergent binary indicating treatment failure may be identified and assured nurse notification may proceed by the binary building method previously discussed.

According to one embodiment, in response to the detection of any significant divergent physiologic binary, the device 306 may be programmed to prevent the failure of notification by building a set notification binaries, which must end with convergence. The device 306 may also be programmed to prevent failure to timely treat by building a set of treatment binaries, which must end with convergence. Further, the device 306 may be programmed to prevent failure test by building a set of testing binaries, which must end with convergence. The device 306 may also be programmed to detect associated physiologic failure image components by identifying divergent physiologic binaries in associated with the initially discovered divergent binaries.

According to one embodiment, the processor 394 includes an associated, connected and/or embedded eventing system. In this eventing subsystem, users may designate actions to be initiated or data to be recorded when a specific occurrence is identified. This eventing system may interface with other internal or external systems including notification systems, workflow systems, asynchronous communication systems, reporting systems, decision support systems, dashboards, data warehousing and/or data mining systems to name a few.

According to one embodiment the relational processor is self-modulating and provides an automatically expanding analysis, which is rapidly responsive to the occurrence of even a minor failure image component. The analytic activity of the processing system is capable of multidimensional growth and diminishment in direct response to the magnitude and number of failure image components detected. In this regard, the processor 394 upon the occurrence of a physiologic failure image component may generate a cascade of notification, testing, treatment, and physiologic binaries even if that failure image component includes only a single physiologic divergent binary. The beta event of the physiologic binary may include the alpha event of each of a new generation of notification, testing, treatment, and physiologic binaries. Each of these new binaries also have a beta event, each which may induce the formation of other binaries wherein the beta event includes the alpha of another binary of the same or another type. A spontaneously growing cascade of binaries thereby evolves toward assuring timely notification, timely testing, and timely restoration of physiologic stability.

A rapidly expanding, cascade of these types of divergent binaries indicates evolving patient instability of the patient or poor performance of the healthcare system. An analysis (as by objectified pattern recognition or statistical analysis) of the timed patterns of the types and sequence of the divergent binaries may allow the determination of poor health or poor responsiveness of the healthcare worker is causing the cascade to be propagated. As health is restored, and provided the healthcare workers are timely responsive, the binary cascade may automatically diminish and the various failure image components may no longer be detected. The outputs of the relational binary object processor therefore provides a self modulating processing system which may be readily used and further analyzed to track the health of a single patient, or the patients on a given floor, or the patients hospital wide. The outputs of the object binary processor also provides a self modulating processing system indicative of the quality of healthcare delivery provided to a given patient, on a given floor, or hospital wide.

The processor 394 may be applied to other complex dynamic data sets other than medical data wherein a self-modulating relational analysis and control would be useful. The processor 394 has utility for the data mining, for example in association with the processing of archived datasets to identify the failure image component process from the initial spark (the first divergent binary) to extensive system failure. The processing of archived datasets provides the opportunity to review the automatic modulation of the binary cascades which are derived of various failures and to facilitate the construction of dynamic failure image component diagrams for complex processes in the hospital, as well as in industrial processing such as the food, chemical, or pharmaceutical processing. The processor may be programmed such that the user may select each alpha event and allow the processor to detect, offer, and/or derive events and relational binaries, which have specified temporal, frequency, or spatial relationships with the selected event object. Alternatively the processor 394 may be programmed to construct its own set of convergent object binaries with a learning dataset by processing the outputs of healthy individuals and then the processor may be used to detect divergent binaries when applied to patients by identifying the lack of the expected beta events (which were defined by the learning dataset). Sensitivity for cascading (the initiation of further processing based on the detection of a divergence or a failure image component) may be adjusted by modifying the sensitivity for trueness of the beta event or by modifying the criteria such as slope, or magnitude of the objects during the objectification process. This provides a high degree of flexibility in defining sensitivity to the designation of a binary as divergent and this therefore allows a high degree of control over the sensitivity to cascade initiation, propagation, and extinguishment. Cascades may be modular or divergent or failure image component specific. A modular group of cascades may be selectable from a menu and then each one in the group modified as desired.

As shown in FIG. 23B, the processor 394 may include instructions for any number of processing functions. As shown the processor 394 may include an event editor 331 (creates event definitions 332), a convergence editor 343 (creates binary definitions sets 344), and a failure image component 355 (creates failure components 356). The event definitions 332, binary definitions 344, and failure components 356, may be used an inputs for the time series objectification processor 336, the relational binary processor 348, and the failure imaging processor 360. The time series objectification Processor 336 is programmed, with the rules and parameters provided by the event definition set 332, to convert parallel time series (324, 328) of the electronic medical record 320. The relational binary processor 348 then, with the rules and parameters provided by the binary definition set, processes the object stream s 340 to generate stream s and cascades of relational binaries 352. Further then, the failure imaging processor 360, with the rules and parameters provided by the Failure image component definition set 356, synthesizes the relational binaries, and in some cases isolated objects from the object stream, into one or more images 364. The output of each of these three processors (336, 348 and 360) as well as the original time series upon which they were applied is stored in an MPPC database 368. In an example, the processor 394 may be programmed so that detection of one or more events, binaries, image components or detection of a specific MPPC, may cause the processor to take action such as provide an outbound notification of the detection, orders for testing or treatment, or direct control signals to a treatment and/or testing device to change, cease or initiate testing and/or treatment.

According to one embodiment, the relational binary processor 348 and the time series objectification processor 336 may adapt to the output of each other to modify the analysis. For example, the detection of an event, a reciprocation, an incomplete reciprocation or other objects or patterns by the time series objectification processor 336 may cause an adjustment to the cascade responsive to the detection of a divergence. Alternatively or in combination the criteria for designation of a wave segment as an event object within the time series objectification processor 336 (for example the slope criteria for identifying a fall event object of serum sodium) may also be adjusted based on the presence of a specific alpha event. In an example, when an alpha event including a diagnosis of cerebral vascular infarction (CVA) is detected, this may cause the time series objectification processor 336 to reduce the absolute slope (less negative slope) for designating a fall event object of serum sodium, which, is preferably one of the betas in such patients. By automatically reducing the absolute slope for the designation of the beta event the alpha diagnosis of cerebral vascular infarction is adjusting the sensitivity of the diagnostic process allowing automatic and dynamic adjustment upon the occurrence and detection of different physiologic vulnerabilities. In this example, the increase in sensitivity for detection of a fall event object in serum sodium (which, combined with the alpha that includes a CVA diagnosis) would include a divergent binary), which may trigger a diagnostic cascade for close monitoring of the serum sodium and/or the evaluation of additional laboratory studies and/or the reduction of free water delivery. This is desirable due to the unique vulnerability faced by patients with CVA as a function of the potential for inappropriate increase in antidiuretic hormone due to the CVA.

Since the relational binary definitions within the binary definition set 344 may be individually defined and refined by processing large populations of historical data, correlations may be verified, rather than being simply proposed and maintained as a function of consensus or expert opinion. In one embodiment, cascades originated by criteria for divergence provided by an expert, which untimely lead to extinguishment without intervention may be automatically adapted to either change the sensitivity for the detection of the divergent beta or to change the cascade resulting for the divergent binary. In another example, cascades originated by criteria provided by an expert which continue self propagate and expand despite timely action and without progression of the physiologic divergence may be automatically adapted to either change the sensitivity for the detection of the divergent beta or to change the cascade resulting for the divergent binary. The sensitively and specificity may be further enhanced because the system may be applied to archived training data sets wherein the outcomes are known so the magnitude and direction of the cascades may be compared to the desired magnitude and direction of the cascades and adjusted accordingly. With applied archived datasets the application of auto-adaptive adjustment in event criteria, divergence criteria, or cascade generation may be applied until the cascades proceed without premature auto extinguishment and excessive propagation. Furthermore the system may be applied to hypotheticals on the missing data to allow determination as to how they might affect incomplete (null) binaries.

According to one embodiment the processors, including the time series objectification processor 336, the relational binary processor 348 and failure imaging processor 360, may output the results of their analysis into the MPPC Database 368. The MPPC Database 368 contains the time series 328 on which the analysis was performed as well as the results of analysis including the event stream s 340, the relational pairs 352, the aggregate failures 364 as well as aggregations, relationships and alternative images of these elements. In one embodiment, the metadata rule-sets (both primary and alternative and/or temporarily overridden or altered elements) are persisted as XML (event definition set 332, binary definition set 344, Failure image component definition set 356) in the patient safety image database 368.

According to one embodiment, a processor is programmed to render sequential time series components (which may be discrete and/or succinct) and which may be subsequently linked other sequential time series components along and across parallel time series to produce a comprehensive relational image of physiologic failure and/or patient care. These components may be rendered by methods defining polarity reversal or inflection points, state changes, by imaging methods to detect pattern components (for example subsequent to time series rendering into a particular format for example), and/or by another method for defining and/or programmatically "packaging" events, image components, and/or occurrences for relational imaging and analysis. According to one embodiment "time series objectification" is employed for this purpose. Time series objectification may be rendered by a time series objectification processor 336, an embodiment of which is discussed below. In one embodiment, time series objectification is the process of converting a set of time series into a stream of sequential discreet elements or objects such that substantially the entire time series of data is converted to a time series of objects in a relational hierarchy of ascending complexity. In another embodiment these objects are created by identifying boundaries within the time series based on the values of the points within the time series (for example threshold violation and/or state match to name a few) and/or the relationship between these points (for example polarity reversal, inflection point, state transition to name a few) using a set of rules based on an understanding of phenomena within the system from which the time series are derived or which are learned adaptively. The discrete objects which are created represent and characterize an occurrence providing a time location and a set of properties derived from the aggregated data within the boundary defined. These objects are differentiated by location and the properties derived and therefore individual objects can be qualified and the stream of objects can be searched against. Further, the conversion to discrete objects provides for the identification, qualification and searchability of relationships between elements. Relationships can be converted into aggregations and/or hierarchy of elements within which properties can be derived from components of an aggregation/hierarchy to the aggregation/hierarchy itself and/or from the hierarchy/aggregation to the participating components.

A time series objectification processor 336 may for example, contain instructions as provided in U.S. patent application Ser. Nos. 11/280,559, and 11/351,449 the specifications of which are incorporated by reference herein in their entirety for all purposes. Accordingly, such processors may function by constructing a time series matrix including of substantially all of the parameters derived during the process of the hospitalization and then objectify each time series in the matrix to produce an objectified time series matrix. The time series which include the matrix may, for example, include objective measured values, drug dosing, infusion rates, and subjective clinical scores to name a few. At least some of the time series may be provided as a step function. For example, time series of the weights, serum sodium values, $SPO_2$, ventilation volume or rate, heart rate, pulse amplitude, pulse slope, drug infusion dose, sedation score, pain score, stupor score, working diagnoses, an instability score, a severity of illness score, to name a few, may all be included.

The objectification processor can define objects by a wide range of methods which may be programmatic and/or image based or by another method of defining objects. In an embodiment, a time series objectification processor applies a linear and/or iterative dipole slope approach to the recognition of waveform events, as for example respiratory or oxygen saturation events. For example, the events associated with airway collapse and recovery are generally precipitous and unipolar, for this reason the linear method suffices for the recognition and characterization of these nonlinear waves. However, the iterative dipole slope approach is particularly versatile and may be used in situations whereby the user would like an option to select the automatically identification of a specific range of nonlinear or more complex waves. Using the iterative dipole slope method, the user may select specific consecutive sets of points from reference cases along a waveform as by sliding the pointer over a specific waveform region. Alternatively, the user may draw the desired target waveform on a scaled grid. The user may also input or draw range limits thereby specifying an object or set of objects for the microprocessor to recognize along the remainder of the waveform or along other waveforms. Alternatively, the processor may automatically select a set of objects based on pre-selected criteria that may be empirically determined. Since the iterative dipole process output may be shape-dependent (including frequency and amplitude) but is not necessarily point dependent, it is highly suited to function as a versatile and discretionary engine for performing waveform pattern searches. In accordance with embodiments, the waveform may be searched by selecting and applying objects to function as Boolean operators to search a waveform. The user may specify whether these objects should be in the same order. Recognized object sequences along the waveform may be scored to choose the degree of match with the selected range. If desired, (as for research analysis of waveform behavior) anomalies within objects or occurring in one or more of a plurality of simultaneously processed tracings may be identified and stored for analysis.

After the process of objectification and further processing of the time series matrix (e.g., generated from object stream s 340) the images are transferred to the patient safety visualization processor 372 (FIG. 23C) which presents and highlights the detected MPPC on an outputted display or patient safety console 306 or through a patient safety report 380 (either electronic or paper) or within an electronic representation as an interface 376 (for example the European Data Format (EDF)) which may provide an interface to external systems. In one embodiment, the aggregation of data, analysis and metadata provide the source of data for the patient safety visualization processor 372. In one embodiment, the Patient Safety Visualization Process 372 provides a visualization of a patient's condition in a comprehensive grouping defined by rows of timelines of specific signals and/or grouping and/or categories of signals and/or signals. In one embodiment the global state of each row is represented by color in a spectrum with a different color moving from stability to failure (for example, Sustained Stability [deep blue], Stability [light blue], convergence [green], Perturbation [yellow], Divergence [orange], Null [black], Failure [red], Cascading Failure [bright red]). In another embodiment colored arrows, icons, blinking or highlighted text, and/or other visual representations along each time line represent these states.

In one embodiment the patient safety visualization processor 372 represents the patient condition as a set of pixel stream s moving from left to right to show evolution of condition over time. The processor provides the navigation backward and forward in time as well as up and down through levels of analysis within the patient safety image database 368. In this embodiment the levels of analysis may be, for example:

time series—Unanalyzed data stream s in the form of time series events and Perturbation—events, state matches, state transitions and threshold violations characterized within their respective channels as to whether they represent clearly defined perturbation according to the event definition set 332

Systemic Response—convergent, divergent and null binaries representing the relationships between events, state matches, state transitions, threshold violations, perturbations and expected elements according to the binary definition set 344

Failure—Failure images that have been identified within a single patient

System Failure—Failure images within a specific category (such as the respiratory system) representing images of failure that have been identified within a single patient Failure Patterns—Trends of failure and failure images within patient population or a specific region, such as a specific hospital ward for example.

In one embodiment the patient safety visualization processor 372 composes an image on computer monitor (the patient safety console 306), which may be composed by a series of pixels oriented horizontally representing data and analysis stream s. These pixel stream s may be stacked vertically with the position on the x-axis representing a specific point in time. The processor provides for the movement of the pixel stream s horizontally to provide a pan through time.

Each pixel stream may be composed of a set of pixels, which indicate the state of the data and/or analysis at the specified point in time. The pixel has a state (e.g. represented by color) and granularity (the length of time it represents [for example 1 minute]). The size of the view as well as the selected span of time determines the granularity of the pixel. In the contemplated embodiment, the pixel is displayed by the highest level of instability found within the time span represented by the single pixel within the pixel stream. Further, each pixel has a level of abstraction, which determines which objects from the patient safety image database 368 contribute to its state. The contributing objects are shown below by level of analysis:

time series—Data points within the channel (e.g. oxygen Saturation Values)

events and Perturbation—events and threshold violations

Systemic Response—Relational binaries

Failure—Failure images

Failure Patterns—Failure trends and correlations.

In one embodiment, groups of pixel stream s are stacked vertically to create a patient safety visualization. Patient safety visualizations may be composed of pixel stream s of different patients or of data and analysis stream s within a single patient. Patient safety images provide the ability of the care worker to filter the analysis quickly to identify problem areas or areas of a specific nature. Sorting may be provided highlight emerging failure cascades or other pattern failures. In an embodiment patient safety images may be composed of different levels of analysis displayed on the patient safety console 306 at the same time correlated by time. The use of mixed-analysis level visualizations provides the care worker with the ability to quickly understand the relationship between the lower levels of data (e.g. incomplete recovery within oximetry) and the higher levels of analysis (e.g. the identification of narcotic-induced ventilation instability).

In an embodiment the patient safety console 306 provides the user the ability to trace a failure condition back to the earliest events associated with the failure to provide a visual display of a failure cascade. Alternatively, individual events and threshold violations may be selected to identify which higher-level objects in which they played a part. In other words, low-level events may be traced forward to understand their relationship within evolving patient instability. This tracing may be accomplished in many ways. For example, the processor 394 may exploit the fact that Alpha events of a relational binary are often the Beta event of a preceding relational binary. This chain of relational binaries provides a powerful tool of analysis. The patient safety visualization processor provides the ability to isolate these binary Chains showing their origin, evolution and resolution.

Alternatively, and in concert, the processor 394 may use the trend of probabilistic momentum. In one embodiment, visualizations may be filtered by the existence and character of binary Chains or a recognizable trend of Probabilistic Momentum. In one embodiment, and if selected by configuration, the patient safety visualization processor provides the ability to navigate into the metadata models at any point within the visualization. event, convergence and image Diagrams or other occurrence definition Visualizations are accessible from objects, which were composed using specified elements within these diagrams within the event definition set 332, binary definition set 344 and image definition set 356. Navigation into the metadata models provides expert care workers and researchers the ability to further understand and/or alter the analysis.

The patient safety console 306 presents a complex set of data and analysis that meets the immediate need of the busy care worker. In one embodiment, analysis at the highest levels may be collapsed into a single pixel stream or group of pixel stream s per patient that provides a simple representation of the evolution of overall patient safety. Within and from that pixel stream the care worker may drill down into the most complex displays: multiple levels of analysis, binary Chains, trends of Probabilistic Momentum and metadata models to name a few. Alternatively this drill down may be provided by for example mouse over, touch screen, or may appear automatically when the processor detects certain adverse patterns or thresholds.

SUMMARY

In one embodiment the PHM is comprised of the following components:

A first objectified time series sub matrix (called a "phenotypic sub matrix") comprised of the objectified phenotypic densities of biologic particles during health;

a second objectified time series sub matrix (called a "perturbation sub matrix") comprised of objectified perturbations of densities of biologic particles;

a third objectified time series sub matrix (called a "perturbation force sub matrix") comprised of the objectified forces inducing the perturbations of the second sub matrix;

a fourth objectified time series sub matrix (called a "recovery sub matrix") comprised of the objectified recoveries of the biologic particle densities from the perturbations of the second sub matrix;

a fifth objectified time series sub matrix, (called a "recovery force sub matrix") comprised of the objectified forces inducing the recoveries of the fourth sub matrix;

and a sixth objectified time series sub matrix (called a "chronically distorted sub matrix") which contains objectified densities of biologic particles which, after being perturbed, have remained persistently different from their phenotypic densities.

Each of these matrices may have a companion objectified expense matrix for incorporation into the PHM. Additional objectified time series matrices, for example comprised of the forces (which may be genetic code) inducing the densities of biologic particles of the phenotypic matrix and/or stabilizing the particle densities of the phenotypic matrix may also be provided. Any or all of these sub matrices may be analyzed or viewed separately or as components of a unifying PHM.

Historical information and subjective symptoms may be included as step functions in the PHM. In an alternative embodiment, historical information is entered as externally supplied events. In an example, an input of a historical symptom of diarrhea "lasting for a week about one month ago" could result in this symptom being added to the PHM at the time subjectively specified. The patient could enter this information with the PHM being built as the patient answers the questions about medical history and symptoms. Subjective times may be given a range, which may be a fuzzy range, in the PHM. In an example, the object diarrhea as subjectively specified above is marked with a range of time rather than a specific time. During an analysis of the PHM subjective times are defined by their ranges. The PHM processor 200 may be programmed with additional supplemental questions to provide greater clarification and specificity to a positive answer (like the presence of diarrhea). Annotations may also be embedded in historical objects, for example a narrative of the history of the chief complaint may be embedded as a digital, read only, or other file in the PHM with linkage to the time to which the history references and the time it was acquired. In an example if a patient indicates that he or she developed diarrhea on a particular date, the onset of diarrhea may be inserted into the matrix at the time specified but with a subjective flag indicating that the data is subjective and may not be highly reliable. The subjective history of the chief compliant and the medical history may be incorporated by the processor 200 into the matrix building a matrix which includes a timed medical history at the times wherein the historical events actually occurred (as subjectively or objectively determined). In this manner the PHM processor 200 projects the PHM back in time, filling in gaps along the historical matrix with subjective symptoms, diagnosis, and physical findings. In one embodiment subjective physical findings are incorporated into the matrix at the time they are discovered and/or they placed at a time along the matrix when they were discovered if the physical findings were present in the past. Subjective physical findings may be recovered as step functions in the matrix. If they are quantifiable a numerical scale suitable for subjective granularity may be included (for example O-5 for normal, marginal, mild, moderate, severe, profound).

While portions of this historical narrative (called "hot" portions) may become timed structural objects of the PHM (from which force, perturbation, and recovery analysis as described herein may be performed), the narrative itself may be stored in the PHM with the portions which are "hot" also representing hot links from the narrative to their timed positions in PHM. A similar approach may be taken for tests such as an echocardiogram, chest radiograph, or CAT scan. The "hot" portions from these studies are added to the PHM while the narrative reports are also embedded in the PHM at the time of acquisition. Examples of hot portions in the report may include the presence of a diagnosis and any numerical, measuring, scoring, or grading, (such as the presence of heart failure with lung congestion severity grade 2 of 5, cardiothoracic ratio of 0.6, a left ventricular ejection fraction of 0.24). The digital studies are also embedded in the PHM (for example, as read only or interpretable files) accessible through the PHM or the hot links in the narrative.

The ability of a physician or other worker to perform program assisted or unassisted interpretation of such studies is greatly enhanced by the availability of the PHM in relation to the study at the time of interpretation. In one example, the interpreter, or the processor 200, in response to the interpretation, may add links to events, binaries and/or force cascades in the PHM thereby assisting the processor 200 or healthcare worker in interpretation of the clinical relevance of the findings of the study to the global PHM. As with the PHM assisted history and physical examination, the PHM, upon identifying primers comprising, for example, findings in the study linked to relevant images in the PHM, may generate one or more questions for the interpreter, the answers and/or results to which may help improve the image in the PHM. At the discretion of the interpreter, the PHM may ask the interpreter directly in text or voice. In this way the PHM processor 200 uses dynamic image primers (or the lack thereof) to focus or expand the interpretation of clinical tests such as chest radiographs, CT scans, electrocardiograms, echocardiograms, or peripheral blood smears to name a few.

One example of a hot portion of a study is a result or finding which warrants detection of the force which caused the result or finding or which warrants detection of recovery or stability of the test or result. For example, a finding of a cardiothoracic ratio of 0.6 results in a detection of the force (for example, heart failure, pericardial effusion, cardiomyopathy, or valvular heart disease) which caused the high ratio. A high cardiothoracic ratio is therefore a hot portion of the chest radiograph interpretation and comprises an theta for which the processor 200 will seek an falpha and designate the binary as unsolved if an falpha is not identified. The processor 200 may also be programmed to expect hot portions in the interpretation (in this example, an indication of the measured cardiothoracic ratio) and to consider the interpretation incomplete if a hot portion is missing. The processor 200 may be programmed to send a notice to the interpreter to complete the hot portion or to warn before saving of the interpretation that a hot portion is incomplete. The processor 200 based potential linkages may proceed in real time and may displayed with the relevant segment of the PHM for the interpreter as in a window, as he or she dictates or enters the interpretation. In an example, the identification of the high cardiothoracic ratio may link to a high brain naturetic peptide (BNP) result, a low left ventricular ejection fraction, a pericardial effusion identified on a chest CT scan, and/or a high blood pressure result. These real time linkages do not indicate cause and effect but rather are parts of the dynamic image of the PHM.

An PHM may be generated which is comprises of all the data, narratives, reports, objects, and sets for which medical related data is available, from the beginning of data acquisition to the point of analysis. In one embodiment, the PHM is constructed as a single integration, comprised of all the objects and time series of objects available. The PHM comprises a medical records repository of linked objects comprising, perturbation forces, perturbations, recovery forces, and recoveries. The configuration and distortions of the PHM and its objects are monitored and analyzed to detect disease, drug reactions, recovery, the need for additional testing or treatment, etc.

The PHM may be divided into compartments or regions. A region of the PHM may be comprised of a set of time series of objects which relate to a specific organ or system. In one embodiment, the PHM is a large compartmentalized matrix dynamically changing in configuration in response to continuous or intermittent flow of medical data. According to some embodiments, the dynamic states of human disease are analyzed by the PHM monitor and outputted to health care workers as direct function of the detection and analysis of dynamic distortions of the PHM.

The PHM is constructed so that the biologic forces and biologic particle densities are highly interrelated. Furthermore, the particle densities and forces are substantially all potentially linked, or otherwise connected to each other in the PHM. For this reason, a new perturbation or a new perturbation inducing force in one region of the PHM will generally induce a dynamic distortion of the PHM which may extend to other regions of the PHM. This distortion will push or pull on other connected portions of the PHM causing secondary, tertiary, and at times cascading dynamic distortions along the PHM. These distortions (as comprised of polyquaternaries) are linked, and the processor 200 is programmed to follow and build the distortions and the motion image of and/or responsive to the linked distortions, and to output the motion image.

Pathologic PHM distortions are not present or are minimal in health. However, physiologic distortions of the PHM are normal in health, as during exercise, or stress. These physiologic, time-dimensioned distortions extend along anticipated regions of the PHM from perturbation force, to perturbation, to recovery force, to recovery, each linked in the PHM to each other to generate a complex physiologic PHM distortion. This distortion may be a "physiologic polyquaternary". A time segment portion of the PHM before a physiologic polyquaternary and after a physiologic polyquaternary is essentially identical whereas they are often different after a pathologic polyquaternary due to residual injury of the matrix.

As discussed in detail below, one embodiment comprises a PHM processor 200 which renders motion images derived from a limited PHM and/or the entire PHM. These images of the PHM may comprise for example, motion images of, indicative of, and/or responsive to a human phenotype or to PHM distortions. In one embodiment the distortions are outputted as complex, linked, cascading PHM distortions indicative of human disease and/or recovery from disease. The distortions may include linked images of objectified expense perturbations associated with the PHM distortions. Distortions of the PHM in one region may be compared with distortions of the PHM in the expense region.

The biologic particles which potentially comprise the PHM of some embodiments are vast in number and diversity. Yet, virtually all of these particles present in the PHM in high density relative to the environment. These particles comprise for example; ions, (such as; H+, K+, or Na+), endogenous molecules; (such as H2CO3, glucose, albumin or brain naturetic peptide); therapeutic molecules (such as levofloxacin, spironolactone, furosemide or cyclophosphamide); endogenous cells or other macro structures, (such as red blood cells, nucleated red blood cells, neutrophils, or platelets); and invasive particles (such as group A *Streptococcus*, lipopolysaccharides, *Strongyloides stercoralis*, peptidoglycan fragments, or bacterial DNA fragments).

The densities of various types of biologic particles in any given compartment of the PHM are generally different than the environmental density of that particle and often different than the density of the same particle in other compartments of the PHM. The relative particle densities in each compartment of the PHM are derived by clinical testing of human compartments (which may be invasive or non-invasive testing). Each patient has density defining forces which determine the densities of the biology particles under their influence. These density defining forces generally maintain each specific particle density at virtually a single density value, pattern of values, or within a very narrow density range. In health and the non-stressed state, the density range for each particle in each PHM compartment in relation to environmental and nutritional factors is specific to the genetic code of the individual human under test. Each patient generally has his or her own phenotypic density range for each biologic particle type in each PHM compartment. These phenotypic density ranges are much different than population defined "normal" densities. In one embodiment, the processor 200 determines the phenotype for the PHM compartmental densities of biologic particles by analyzing the phenotypic components of the PHM (derived in a state when the health of the patient and densities are at their resting baseline and wherein the densities are "unperturbed", for example, not acute or sub-acutely stressed) or of the phenotypic sub matrix.

One embodiment defines the phenotypic or population variability of a test around a measured value (which may, in some cases, be less than the inter-measurement variability due to the testing instrument itself. The patient's baseline and the phenotypic or population variability are used to define the phenotypically normal range for the patient rather than the use of the population normal range.

Each of the biologic particle density objects in the phenotypic sub matrix has, for example, the characteristics of absolute unperturbed density value, relative unperturbed density, and unperturbed density range, variability, and/or pattern. A phenotypic sub matrix may comprise a dynamic image of the densities of any or all compartments, physiologic systems, or physiologic grouping of cells. In one embodiment a segment of the PHM from a healthy young human at rest is used to define the future phenotypic values and ranges for future reference. The phenotypic ranges change as the patient ages and may be reassessed periodically.

As discussed, when defined statistically, the human population generally has a much wider range of so called "normal" particle densities than is defined by the unperturbed variability associated with any individual particle density phenotype. The common use of, for example, defining "normal" for an individual patient as a range of 2 standard deviation for the high limit of a population and a 2 standard deviation range for the low limit of normal of a population is incomplete. While the PHM may incorporate objects which relate to these traditional thresholds for reference, distortions of the PHM induced by these types of thresholds are considered along with the actual distortions in relation to the phenotypic ranges in the analysis process.

According to some embodiments, the phenotypic range for each density value is defined as the phenotypic range of the density value in a phenotypic sub matrix or when the PHM is undistorted by any active non-genetic force. The phenotypic range is ideally determined for each individual by making multiple measures over time but this is often not practical. For this reason, in one embodiment, the phenotypic range is determined by examining the individual ranges within individual phenotypic sub matrices of a large population. This range is then applied around the density value of the phenotypic matrix which is generated for the individual during a clinical state of health. The range may be defined by statistical methods but in this case it may for example, be the standard deviation of the individual ranges of unperturbed density variations in the population, rather than the standard deviation of densities in the population itself. Since the position of the density value in the range may not be known, an additional cushion may be added (such as one or two average deviations or standard deviations) to the high and low phenotypic range. Measurement of additional phenotypic densities, when available may be used to better identify the range and allow elimination of the cushion.

In one embodiment the PHM processor 200 is programmed to generate a large set of phenotypic populations sub matrices from healthy individuals during a non-stressed state of health and, analyze the sub matrices to define the phenotypic ranges of objects in the sub matrices and to define the phenotypic ranges of the unperturbed variability around the individual density values.

According to some embodiments, at least one phenotypic PHM distortion may be defined by analysis of a PHM distorted by a non-genetic force. This may be identified if a known perturbation force, such as a new or increased particle density of a drug, is introduced into the PHM and the perturbation induced by the force was within the expected range. The specific or general distortion of the PHM in response to the perturbation force induced by the drug may be defined as a specified force induced phenotype of that PHM.

Both the phenotypic sub matrix and the PHM distort with age but are often highly stable within periods of an individual's life. In one embodiment the rate of distortion with age of the phenotypic sub matrix and/or the PHM may be tracked and compared with other individuals or populations.

In one embodiment, the processor 200 defines human compartmental particle; densities, density perturbations, density recoveries, density rate of change, and density momentum mathematically by time series derived amplitude and slope formulae. The movement of a mass of particles into or out of a human compartment, or the consumption of particles within the compartment is inhibited by an aggregate resistance (modeled for the purpose of illustration as a human particle flux resistor) which is initially genetically defined and comprises a phenotypic density flux resistor. Particle flux resistance is particle and compartment specific and is initially phenotypically defined but may then be affected by disease, injury, environmental, nutritional, and/or aging factors. Particle flux resistance is a function of human systems, and may include a combination of factors such as membrane flux resistance, molecular buffers, molecular or ion pumps offsetting the flux, and organ compensation, to name a few.

Particle flux resistance may not be measured but is rather generally inferred by the time series pattern of the particle density in relation to the time series pattern of forces which potentially affect the particle density. These forces may or may not be detectable or measurable but are inferred as a function of particle density time series patterns. Low particle flux resistance may also be identified when particle densities which are stable phenotypically begin to vary widely (for example, oscillate) when no major exogenous forces are active. One example of this is the development of oscillation of oxygen molecules in the arterial blood compartment which may occur in association with severe decline on left ventricular function. In this example resistance to particle density flux (of arterial oxygen particles) has declined due to loss of sufficient flow rate of arterial blood. A normal arterial blood flow rate normally allows a central controller of the brain to respond to changes in oxygen density rapidly and therefore promptly resist the particle flux. Particle flux resistance may be also affected by exogenous factors (such as medications). In an example, an ACE inhibitor which improves left ventricular function may increase the resistance to the particle flux of arterial oxygen in the example descried above but decrease the resistance to positive K+ particle flux in venous blood.

A perturbation of particle density is generally caused by a force change which is associated with energy and work. According to some embodiments, a relative indication of the energy or work associated with a perturbation may be calculated. The density change is a direct function of the cumulative mass of the particles which are moved by the force (or the mass of other molecules such as water, which are moved into or out of the compartment to dilute or concentrate the particles). For the purpose of relative measurement, the density change may be substituted for the particle mass moved so that the amplitude of the particle density change may be substituted for the magnitude of the particle mass which moved across the resistor during the perturbation. The aggregate momentum of the density change (for a given perturbation or group of perturbations) may then be calculated as the product of the change in density (surrogate for the mass which moved) and the rate of density change (the velocity of movement of the mass).

Since the particle flux resistor actually comprises a system resistance to particle mass movement and is not generally calculated or known, the momentum associated with any perturbation is relative. A decline in resistance will increase the perturbation for the same force (and increase the apparent momentum as calculated above) but since both a decline in resistance and increase in a force are simply components of the same density change vector, the model of aggregate particle momentum for the purpose of medical diagnosis remains valid. In other words, since disease, such as infection, may lower the resistance to particle mass movement and/or may apply a force to induce particle mass movement, these relative effects are not readily separated and are therefore combined to generate the value of the "functional momentum" of a perturbation or recovery. Human life, and the integrity of the human system, is functions of the particle density and, as noted, this is substituted for the mass in the above equation for this model. Furthermore for the purposes of processor 200 based assessment various measurements such as milliequivalents (meq) may be substituted for the mass in the calculation of density.

As it relates to the state of life and health of a human system, the absolute values of a particle density or the absolute values of a particle density change of different particle types are not mathematically comparable either from a severity or probabilistic perspective. For example, a density rise of 7 meq/100 cc of bicarbonate in venous compartment (which would, in most cases not generally cause distress) does not comprise the same severity as a density rise in density of 7 meq/100 cc of potassium (which would generally be fatal). In many cases a severe a deviation above a threshold of one particle density may comprise a much less severe event than a mild deviation of another particle. To adjust for this disparity provide and image which is indicative of global perturbation severity and recovery, one embodiment comprises a processor 200 programmed to convert the absolute particle value types of; densities, density changes, density perturbations, and density recoveries, density rates of change, and/or density momentums, to "human numbers" called R which are more indicative of the human relevance of those values and which are comparable across a wide range of particles and value types. The conversion generates a "Human Life Relevance scale" (an "R scale") for the densities, density perturbations, density recoveries, and density velocity (rate of change), and density momentum (the product of the rate of change and the duration of the perturbation or recovery) thereby providing a comparable mathematic quantifications of these values in relation to the stability of human life.

In one embodiment, the processor 200 applies a process of conversion of particle density values to the human life relevance scale which may, for example, comprise the application of direct conversion formulae but generally a conversion table for each particle and value type is preferred because these relationships of these values to human life are not linear or readily defined by formulae. Using the conversion method, the processor 200 converts the absolute value into density relevance values DR which are unit less numbers. These conversions are processed in relation to a central point which comprises the normal range for the individual human which can, for example be designated by as 0 DR. A similar approach may be applied to convert perturbations, forces, recoveries, binaries, and images to respective R scales.

In one embodiment the density value range above the phenotypic range are converted by the processor 200 to a range of values from a first DR to a second DR (such as 1 DR and 15 DR). The particle density range below the phenotypic range may also be normalized from a first DR to a second DR (such as −1 DR and −15 DR). The value 0 may be specified for all densities in the phenotypic range, or may be set to the median or average value of the phenotypic density for the individual or the normal range for the individual human may, for example be designated as noted above by a range of 0-0.9 DR. If the phenotypic range is unknown 0 may be set to the median or average value of the population range until a phenotypic range may be established.

These conversions may be designated by the processor 200 with the particle, the compartment, and the DR (such as potassium, venous, −12 DR which indicates a dangerously low venous potassium). The term low may be added (−12 DR low) to assure the position of the potassium is instantly recognized by the researchers and programmers (as these designation are not for use by the healthcare workers, who, being trained with absolute density values, may become confused by the conversion).

As with the conversion of density changes discussed above, one purpose of the conversion is to allow comparison of severity of density values across different particle types. In one embodiment the conversion curves derived from the absolute values are configured with a hysteresis so that the values become more rapidly closer to 15 or −15 as the extremes of the potential range of the values are approached.

An example of a heuristically derived DR for venous H2CO3 when sepsis, diabetic ketoacidosis, methyl alcohol intake, or lactic acidosis pattern or image primers (which may for example include an elevated anion gap) are present comprises:

Venous H2CO3 (in meq) (on left)-converted to DR (on right)
<16-15, 16-15, 17-15, 18-14, 19-13, 20-12, 21-10, 22-8, 23-4, 24-2, 25-1, 26-0, 27-0, 28-0, 29-0, 30-1, 31-2, 32-3, 33-4, 34-5, 36-6, 37-7, 38-8, 39-9, 40-10, 41-11, 42-12, 43-13, 44-14, 44-15, >44-15

In this conversion the elevated DR even in the low "normal range" and the rapid elevation of DR for each incremental H2CO3 value below 26 reflects the acuity of danger these densities may reflect. Since acidosis reflects often reflects a more dangerous dynamic in sepsis then in diabetic ketoacidosis higher DR may be selected for sepsis then for diabetic ketoacidosis. When two venous H2CO3 data values are available an actual perturbation will be detectable and this can be converted to PR using a perturbation conversion set. A second conversion below of H2CO3 (on left) to DR (on right) provides gradation of severity only in the direction of progression of sepsis. In this example high normal and high Venous H2CO3 are given no severity weight.
<16-15, 16-15, 17-15, 18-14, 19-13, 20-12, 21-10, 22-8, 23-3, 24-1, >25-0, If preferred the phenotypic range or the population normal value may be converted to DR from −0.9 and 0.9 so that density changes within this range may be tracked. The conversion curve for DR between −0.9 and 0.9 may also be configured with a hysteresis so that the DR become more rapidly closer to 0.9 as the extreme of the normal range is approached.

Like the conversion for densities, the conversion to R values also allows, for example, "human life relevant perturbation" (RP-) to be comparable across different types of perturbations. For example, for a potassium rise, the conversion to RP may be formulaic or a direct conversion of for example 0.2 miliequivalent of potassium rise for each RP between 1 and 15. Alternatively the RP-may be a combination of the density change and the absolute peak or nadir value reached. For example, a rise of 2 meq. of potassium to a peak of 5 meq. may generate a lower RP—then a potassium rise of 2 meq. to a peak of 7 meq. Each density rise may be combined with the peak produced by that change to generate a RP between 1 and 15 and this may be performed heuristically and then modified over time to enhance performance as it becomes evident that different RP are preferred. The use of the peak value in combination with the density change is consistent with the flux resistor model as applied in one embodiment as described above as the resistance to a density change is reasonably assumed to be higher as the peak of the change vector encroaches into extreme and/or dangerous density levels. The human system may have secondary layer of protective resistance near extremes so that resistance may suddenly increase when density levels rise or fall to values near the extremes. According to one aspect of some embodiments, the conversion curve for particle densities and peak or nadir values which fall within a specific range compatible with life, may demonstrate a prominent hysteresis near extremes.

In addition to the lack of direct comparability of absolute density changes between particles, one perturbation or abnormal value of a particle density caused by one force, may be much less severe, as it relates to immediate risk, than an identical density perturbation of the same particle density caused by another force. This may not be accounted for by a conversion severity scale unless the scale is adjusted for different perturbation forces or clinical conditions which inducing the density. In an example a H2CO3 of 22 which has fallen due to volume expansion is considered representative of mild severity whereas the same H2CO3 due to sepsis is considered representative of high severity. A universal conversion scale to a human severity value will not solve this problem of diversity of severity. The PHM may be programmed to have to apply different severity scales or otherwise adjust the severity of the particle density based on the image (for example a sepsis image) of which it is a component or based on a detected force which may be inducing induced the particle density. This is referred to herein as conditional severity adjustment. Alternatively or in combination the severity of the H2CO3 is not adjusted in this manner by the processor 200 upon detection of the image or force, but rather the force binary itself is designated with the high severity, that is the force binary comprises the conditional severity adjustment as a function of its components. This may be achieved by applying different severity scales to different force binaries even though the severity of the theta of the binary is not adjusted. This may prevent confusion by many healthcare workers who may find it difficult to mentally accept different severity indications for the same density value of the same particle.

One embodiment estimates a density velocity associated with the aggregate movement of particle mass associated with a single perturbation or recovery or a combination of a perturbation and recovery. The output of the density velocity as defined by the slope of density change may be converted to adjust the R scale from, for example 1-15 velocity R (VR), so that the severity of momentum is reasonably comparable across particle types. One embodiment estimates a density momentum associated with the aggregate movement of particle mass associated with a single perturbation or a recovery or a combination of a perturbation and recovery. The output of the momentum estimation may be converted to adjust the R scale from, for example 1-15 "momentum R" (MR), so that the severity of momentum is reasonably comparable across particle types. Other converted severity values such as perturbation force may also be calculated if multiple measurements are made allowing the detection of acceleration. It may be preferable to use the various R only as tools to generate images and not to output or quote R to clinical staff as clinicians may confuse these normalized severity measurements with actual density values. The displayed numeric outputs in the organelles are preferably the absolute values of density or density change, whereas the color, size, shape, movement, or position, of a given organelle may be a function of one or more R or other indicator of severity such as relational indicators.

With this approach density changes may be defined as a function of the R. In one embodiment changes in density toward normal are considered recovery changes or recovery vectors. These may be quantified as recoveries and designated with the direction, momentum, and duration of the vector. For example a low venous potassium density of 2 meq/100 cc may be designated with a conversion to 12 DR (as it is a life threatening low density) whereas a potassium value of 4 meq/100 cc may be converted to 0 DR as this value is likely to be phenotypically normal. If the potassium moved from 2 meq/100 cc to 4 meq/100 cc in 24 hours, the converted perturbation severity may be calculated as 0 PRP as the movement from 12 DR to 0 DR is not considered a perturbation but is rather considered a recovery. In this example the recovery change will be designated as 12

Recovery R (RR) reflecting excellent recovery from a severely perturbed density value.

One example of DR and PR designated heuristically. In this example, if the potassium was 2 meq/100 cc and then measured 24 hours changed to 5 meq/100 cc this may, for example, generate a first venous potassium DR of −12 and a second venous potassium DR of +4. However, the movement of such a large mass of venous potassium into the venous compartment may pose a risk if the force causing the movement remains operative. However movement toward normal carries less risk than movement away from normal so this may be weighted (for example by multiplying a recovery movement by 0.5 or another value as reflected for example in a weighting table). Therefore, the conversion for the above rise event from 2 meq to 5 meq to R would comprise three vectors, two sequential positive R vectors, the recovery R vector and the perturbation (overshoot) R vector, and the vector sum of the two R vectors, all three of these may be described by R values with the third representing a vector sum, the vector sum representing the total movement of particle mass during the sum of the duration of the two vectors. For some particles, anytime the total change is high there is reason for concern whereas with others, such as invasive particles, a fall may only be favorable so that for this particle the weighting of the severity of a change may be different for different particles, for example with invasive particles change, the absolute value of any fall in particle density may always be designated by RR.

The connections and interrelationships of the forces and the particle densities which comprise the PHM are extensive and the PHM is temporally and spatially interdependent. For this reason, a local primary distortion of the PHM often induces secondary distortions of the PHM. These secondary distortions comprise dynamic changes of other particle densities and/or other forces which comprise the PHM. This secondary distortion may be self-limiting and may be reversed by secondary recovery forces or this secondary distortion may induce a tertiary distortion or a force cascade of PHM distortions which may spread across the PHM and overwhelm even cascading density stabilizing and recovery forces until these forces are no longer sufficient to return the PHM to a state where sustained life is possible. The PHM now is in a state of terminal distortion. Terminal distortions are generally initially highly complex and may further increase in complexity despite the inability of the matrix or healthcare workers acting on the matrix to return the matrix to a state which will remain living very near death and after death the matrix may exhibit a progressive more entropic pattern over time as life forces progressively diminish to the no life force state. The entropic progression may be more rapid in specific compartments of highly complex function and high dependence on high instantaneous oxygen density, such as the brain, whereas it may be less rapid in compartments with less complex function and less dependency on instantaneous oxygen density.

According to some embodiments, the presence of a density modifying force in the PHM is identified by identifying a density perturbation of at least one biologic particle in at least one PHM compartment. The density perturbation (and the related severity of the perturbation) may comprise, but is not limited to, at least one of a magnitude, a slope, an acceleration, a pattern, a polarity, a percent change, a frequency, an amplitude, and relational combinations of the preceding variations of the same or with other particle densities. Density perturbations commonly occur as a rise (increasing biologic particle density) or a fall (decreasing biologic particle density) or in the alternative a perturbation may comprise a deviation form a normal (phenotypic) pattern of a particles density over time. However, two instances of increasing density of the same particle, for example, may comprise different types of events which only share the common feature of comprising a rise in the same particle density. Since, in one embodiment, as will be discussed, the processor 200 links perturbation inducing forces with perturbation events, the two instances may not be otherwise related in terms of causality. In an example a fall in platelets with a low slope may be defined by the processor 200 as a different event (rather than a less severe event) from the decrease in platelets with a high slope. In this way perturbations of similar polarity but with different patterns suggestive of different causal forces may be readily linked by the processor 200 to the forces more likely to have inducing them. In one embodiment the linkage is of variable strength and based on probability of the linkage.

The linkage may be scaled between 0 and 15 with 15 representing the highest probability of causal linkage. For example a H2CO3 fall associated with a rising anion gap, and a rising lactate, and a low SVO2 provides a linkage of 15 indicating the pattern of forces is sufficient to render a definitive causal diagnosis that these forces caused the negative perturbation of H2CO3. However, neither a rising anion gap, nor a rising lactate, nor a low SV02, are apical forces which may begin the process. In one embodiment the processor 200 is programmed to proceed with searching and testing until the apical force is identified.

In one embodiment the PHM processor 200 builds the PHM and its distortions by linking objects to produce basic relational objects which may comprise 2 linked events (binaries), three linked events (trinaries) or four linked events (as coupled binaries or as quaternaries) and builds more complex objects (for example force cascades of events or force cascades of binaries, trinaries or quaternaries) by adding objects. Binaries include but are not limited to: An image binary may be comprised of, a first event or exogenous action (called an ialpha event) and second event or exogenous action which occurs in relation to the ialpha (called an ibeta event).

A perturbation force binary may be comprised of, for example an endogenous force or exogenous action (called a falpha event) which potentially induces a perturbation event (called an theta event). This is contrasted with image binaries which are linked due to their relationship in an image or cascade and not necessarily due to a force-density perturbation relationships.

A recovery force binary may be comprised of, for example an endogenous force or exogenous action (called an fsigma event) which potentially induces a recovery event (called an ftau event).

In one embodiment, an fbeta cascade comprises a cascade of perturbations (which is the typical early image of a cascade). An ftau cascade comprises a cascade of recoveries (which is the typical late image of a treated cascade). An theta cascade-ftau cascade reciprocation may be comprised of the combination of a perturbation cascade and a recovery cascade. These are the types of incomplete images of distortions which often exist before the polyquaternary which defines the identity of the distortion of the PHM is solved.

One or more variations of falpha may induce or otherwise cause or contribute to the same type or types of variation or a different type or types of variation of the fbeta event. A particle density modification which comprises an fbeta event is often both a threat to the health of the human and also a marker which the processor 200 analyses along with other binaries or image components to generate a distortion comprised of the falphas and thetas and to identify to the source(s) of that threat.

Within one compartment of the PHM, such as, for example, venous blood, a first particle density induced by a first force may comprise a second force which alters or tends to alter the density of at least one second particle within the same or another compartment. The second density modifying force may be induced by the second particle density directly or indirectly (as, for example, through the action of the particle on an organ or group of cells which induces the density modifying force). The processor 200 continues to links new forces and densities to generate images and cascade of linked forces and perturbations. Alternatively dysfunction or failure of an organ or group of cells, and/or the increased or decreased intake or output of a given particle, may comprise a first density modifying force without an intermediate particle.

A first perturbation of particle density responsive to a first force may comprise a second density modifying force on at least a second particle density. These events and forces are linked by the processor 200 to generate cascades of particle density perturbations and the companion cascades of particle density modifying forces which induce the perturbation cascades. These generate apical or primary, secondary, tertiary and cascading distortions of the PHM and of the motion images responsive to or representative of the dynamic distortion.

In one embodiment, a density modifying force is defined as a recovery if the direction if the force vector is toward a normal range and as a perturbation of the direction of the vector is away from a normal range. The density modifying force is further defined as positive (and/or the perturbation or recovery is defined as positive), if the particle density perturbation or recovery responsive to the force comprises a rise in density of the perturbed particle. The density modifying force is defined as negative (and/or the perturbation or recovery is defined as negative), if the particle density perturbation or recovery comprises a fall in density of the perturbed particle. The density modifying force may be a direct force or may be mediated by one or more controlling sensors responding to the perturbation, and/or one or more other particle densities or perturbations.

In an example, an alpha (a perturbation force) comprising a rise in the density of the molecular particle, $H_2CO_3$ in venous blood away from the normal range, may induce an theta (perturbation event) comprising a rise in the density of the gaseous particle $CO_2$ in arterial blood. In another example, an alpha comprised of arise in the density of the particle cortisol (as defined by the administration of the drug or a measured drug level) may further comprise a positive falpha in relation to particles glucose, insulin, and neutrophil and a negative falpha in relation to particles lymphocyte and eosinophil. In a further example an falpha comprised of the infusion or at least a minimal density of the particle heparin may further comprise a negative falpha on the particle platelets in the presence of an falpha comprised of a minimum density of a companion falpha particle, antiplatelet factor 4.

The processor 200 is programmed to manage exceptions to this approach. For example, during a sepsis cascade, a rise in the density of neutrophils may peak and then the neutrophils may fall back toward, into and then below all of the normal ranges. In one embodiment, this is identified and designated as a bipolar perturbation which is a subclass of a perturbation wherein the positive perturbation force is later replaced by a negative perturbation force (in the case of neutrophil case comprising relative failure of bone marrow production or release) and is divided into two sequential force binaries, a first perturbation binary and a second negative perturbation binary which is corrected by a positive recovery.

The processor 200 may be programmed to consider a plurality of factors in discriminating a bipolar force perturbation from a force quaternary. For example, if the processor 200 detects at least one of, parallel perturbations or the slopes of parallel perturbations which have not become less severe, the interval after treatment to the onset of the reversal in polarity is insufficient to expect recovery, or a new perturbations suggestive of increasing severity has developed adjacent in time to the reversal, then the processor 200 designates the perturbation as a bimodal perturbation and identifies the second portion of the bimodal perturbation as a second force perturbation having the same force as the first force perturbation. In the above example if the processor 200 detects a rise in neutrophils followed by a fall, the processor 200 looks for the forces which induced the rise and the force which induced the fall. The processor 200 also evaluates the parallel perturbations or the lack thereof. If, for example, if the processor 200 detects that a negative perturbation of $H_2CO_3$, a negative perturbation of platelets, and/or a positive perturbation of heart rate continue without reversal of slope or improvement then the processor 200 may identify the neutrophil pattern as a potential bimodal perturbation of neutrophils and then may designate the rise in neutrophils as a first perturbation and the fall in neutrophils as a second perturbation not a recovery. These two sequential perturbations will have the same falpha (in this case sepsis). However, the processor 200 may seek to identify another other force or other forces (other than sepsis) along the PHM which may have triggered a fall in neutrophils (such as chemotherapy).

For particle densities which may potentially exhibit a bipolar pattern, for example in response to a common a single force, the designation of a recovery (ftau) by the processor 200, will occur if an antecedent theta (which is at least partially reversed by the ftau) has been detected and no competing perturbation, force which would explain the reversal and solve the change as a new force perturbation is identified. If no theta has been detected a change in such a particle is designated as a perturbation.

A recovery may overshoot and this will comprise an overshoot perturbation and will be detected by the processor 200 as a continuation of the recovery vector until it turns into a perturbation as it passes the normal range. A recovery force comprises the perturbation force of the overshoot perturbation. One example which may produce a positive perturbation overshoot is a neutrophil recovery in the above example.

The particle density which induces a perturbation force may be external to the compartment wherein the perturbation of particle density occurs. A positive or negative perturbation force, or a high or low value of particle density, in relation to the patient's phenotypic range (or the relevant population's normal range of a the particle density) indicates that one or more forces, which may induce that range of positive or negative perturbations, has likely occurred.

In one embodiment the processor 200 is programmed to detect a perturbation in density of one particle along the matrix and then to determine at least one value indicative of the perturbation or one or more features or measurements of the perturbation (for example a change in density value, density slope, etc.). The processor 200 is programmed to order, detect, and/or quantify the density of other particles and/or to detect a perturbation force or recovery force which would be expected to induce the perturbation or recovery the at least one value indicative of the perturbation or recovery. In one embodiment the processor 200 builds a time matrix of particle densities, actions, and dysfunctions, objectifies the time matrix, and then identifies the occurrence of objects comprising potential perturbation forces by identifying the occurrence of positive or negative density perturbations or of high or low density values, and then identifies and/or outputs the potential perturbation forces as well as the projected forces on other particle densities as well as the matrix or an image representative of the matrix.

In an example, if a positive density perturbation and/or high density value of the particle K+ is identified in the venous blood compartment of the PHM, then this indicates that a perturbation force has occurred because the K+ particle density or at least one feature of the perturbation is outside the range or otherwise is varying in a manner, which would, without the presence of this perturbation force have been prevented by the density normalizing force that particle. The recognition by the processor 200 that a density modifying force either has occurred, or is occurring, triggers a search for the perturbation force which could have caused the detected density value or density perturbation. This force may, for example, be one or more of: an action causing an increase in intake of K+, an increase in intake of K+ itself, another particle density which causes a positive change of K+ such as a beta agonist particle or aldosterone antagonist particle, or an organ dysfunction such as renal dysfunction (which may, for example, also induce a perturbation force on the particle creatinine so that venous creatinine density may be used as a marker for the force (for example, a positive perturbation force comprising an increase in the venous density of creatinine may then comprise the falpha for an beta event comprising high or increasing venous K+ density). The perturbation force binary would comprise a linked increase in creatinine density and an increase in K+ density. The processor 200 would then search for other potential falphas such as the intake of aldosterone antagonists and/or an angiotensin converting enzyme inhibitor, and/or the intake of KCL or other molecules containing K+. The processor 200 will then search for the one or more fsigmas, (the recovery force(s) which will induce the recovery of the perturbed K+ density), such as, for example the discontinuation of the angiotensin converting enzyme inhibitor. If no suitable fsigma is detected, the processor 200 may be programmed with protocolized order for at least one fsigma and then to detect the occurrence of the fsigma which was ordered, and to order additional diagnostic testing to assure the expected or desired ftau (recovery of the venous K+ density occurs) within the specified time interval.

In addition to the sequence above the increase in venous creatinine density represents both an ialpha and a falpha. In one embodiment five or more ranges or relational ranges of density values are stored for a particle density (such as creatinine) for any given compartment; a first population range as defined by the relevant general population, a second phenotypic range, a third personal baseline range as defined by the patient's baseline values around which is the phenotypic range, a forth risk range, as defined by that particle density related risk values (if any) in relation to the PHM, which may include the medications received, the images and or cascades generated by the patient, or the patient's known conditions, and a fifth range as defined by a range of preference or for some specific purpose by the healthcare worker(s) managing the patient.

In the instance of creatinine, a positive perturbation of venous creatinine density outside the patient's phenotypic range comprises an theta for which the processor 200 will search for the falpha which could have induced that perturbation in relation to the PHM. The falpha (perturbation force) may comprise a medication, an inflammatory cascade, sepsis cascade, a fall in fluid intake, a fall in cardiac output, to name a few. If a suitable falpha is not identified or if a detected fsigma (recovery force) fails to reverse the falpha, when reversal would be expected if the falpha was the only force active in relation to creatinine, then a range of testing for falphas may be ordered by the processor 200 as protocolized. In addition, this theta of creatinine comprises a positive sentinel falpha for many other positive particle density perturbations of, such as medications cleared by the kidney. Furthermore, this theta of creatinine comprises a negative sentinel falpha for negative particle density perturbations such as H2CO3.

The processor 200 may be programmed to search for, analyze, and link each potential theta and to order tests for particle densities which, given other distortions along the PHM, may be affected and to reduce particle densities (such as drug dosages) which are likely to be affected. In one embodiment, a perturbation of a single particle density (such as a positive perturbation of venous creatinine density or a negative perturbation of venous platelet density) may trigger a range of object linkages extending from the falpha objects generated by processor 200 which characterize the positive perturbations. These objects may then be linked to the theta. The theta will be linked to the fsigma, which will be linked to the ftau. The combinations of these many linked objects generate an image and physiologic characterization of the global impact on the PHM and in particular on the dynamic patterns and values of densities of a wide range of particles in the venous compartment that an falpha may be inducing (or signaling in the instance of a sentinel falpha).

Perturbation force binaries may be identified as having a solution if one or more falphas, which would be expected to induce the perturbation values or range, has been identified. Perturbation force binaries are identified as having no solution if no falphas have been detected which would be expected to induce the perturbation values or the range which has been detected. Binaries with no solution, comprise for example; perturbations and or high or low density values, without the expected forces or relational events, perturbation forces without the expected perturbation, recovery forces without the expected recoveries, and recoveries without the expected recovery forces. A time matrix or other rendering of binaries which have a solution may be generated and displayed in combination with or separate from the time matrix or other rendering of binaries without a solution. In one embodiment, a PHM may be comprised of binaries with and without solutions which may be differently designated or displayed.

In an example, a positive perturbation of venous density (or a high venous density value) of neutrophils may be induced by a range of forces. As noted, the presence of a minimum density of corticosteroid particles comprises one potential falpha inducing a positive perturbation of neutrophil density. However, the increase in density of neutrophils induced by corticosteroids is generally modest and corticosteroids would not be expected to induce marked increase in density of band particles. Therefore, a perturbation indicated by a modest increase in the density of neutrophils (a first theta event) would have one solution identified if corticosteroid administration is identified as an falpha event by the processor 200. However, if a positive perturbation in temperature (a second theta event) and a positive density perturbation theta in band particles 9a third theta event) is identified, the forces inducing these two fbetas cannot be solved by a corticosteroid falpha. Furthermore, since the three fbetas are all potentially relational (relate to a common falpha), the corticosteroids are designated by the processor 200 as an unsolved perturbation force binary for the relational binary wherein the theta is a complex object comprised of a combination of the three related fbetas. In one embodiment, the processor 200 is programmed to output the presence of two perturbation force binaries with no solution and a third perturbation force binary with a solution. The processor 200 may then output a visual indication of all three thetas and variations of the relational pattern of all three thetas (as derived from the increase in venous neutrophil density, increase in temperature, and increase in density of band particles) along with the designation that the falpha for these thetas and particularly for the combination of these thetas (when grouped as a single theta object) has not been identified.

In one embodiment all elements that have a potential to form any binaries—exogenous events, occurrences, patterns, and forces to name a few—are continuously monitored (e.g. searched for) such that the absence of an element, after a sufficient processing delay or cycle indication, may be recognized as a failure of identification for a given time span, and therefore may indicate a binary without a solution.

Overlapping dynamic visualizations such as weather maps responsive to binaries with solutions and without solutions may be generated. In one embodiment annotations or other indications are provided which may indicate that a patient storm cell or group of patient storm cells does not have a solution and the falpha (and particularly the apical falpha) inducing the storm cells is unknown.

In one embodiment, the processor 200 is programmed to display which binaries have complete solutions and which do not. Overlapping weather maps responsive to binaries with solutions and binaries without solution may be generated. In one embodiment annotations or other indications are provided which indicate that a patient storm cell or group of patient storm cells does not have a solution (and the forces or inducing the patient storm cell is not yet known).

The unsolved falphas and fsigmas may be mapped on a time matrix in relation to the position of associated positive and/or negative density perturbations (and/or high or low density values) and recoveries which indicated the presence of the undetected forces. A large or expanding matrix of many binaries with no solution may be indicative of diagnostic delay (for example, caused by inadequate protocol, a breakdown in protocol, inaccurate diagnoses to name a few). The processor 200 may be programmed to quantify the number of individual and relational binaries which do not have a solution and to provide an output indicative of unsolved forces per unit time.

Early in the presentation of the patient, there may be many binaries without a solution. As time progresses, the number should progressively reduce. A graphical representation of the number of unsolved binaries may be presented to QA personnel and protocol violations may be indicated. At discharge, binaries without a solution which remain may be outputted by the processor 200 along with orders or recommendations for solving the binaries if warranted. The identification and quantification of density perturbation forces according to some embodiments provides more sensitivity to residual and dynamic diagnostic deficiency then the conventional identification of abnormal laboratory or vitals values at discharge.

One embodiment programmatically images the parallel physiologic time series to render a relational pyramid of data with the top of the pyramid representing data at the highest level of analysis and abstraction while data moves down through layers of analysis, the bottom layer being the raw data stream s. The healthcare worker may investigate the pyramid in the following ways to name a few: (1) Drilldown—the care worker may navigate into the details of the data and the rationale of the analysis (i.e. both the conditions that exist and the rules by which the analysis has arrived at its conclusion); and (2) Aspects—view ports into the system which emphasize certain elements/conditions and de-emphasize (and/or filter out) other elements/conditions). These two examples above may be used together allowing the healthcare worker to navigate through the relational pyramid vertically (drilldown through levels of analysis) and horizontally (through filters/aspects).

In one embodiment the relational pyramid may be manipulated by the healthcare worker and/or researcher to consider hypothetical scenarios or scenarios based on the rejection of certain test results or events which may be considered in error, anomalous or otherwise inaccurate. Alternate pyramids may be stored in whole or as differential images. Alternate pyramids may be compared against the working pyramid to understand the results of the altered data.

In one embodiment, the processor will automatically consider alternate pyramids under certain conditions—such as the existence of perturbation for which no precursors may be identified. The sudden existence of perturbation or of divergence may, by considering the range of possible precursors, suggest anomalous conditions: inaccurate diagnosis, faulty monitoring equipment, labeling mistakes, the failure of a patient to take medication as prescribed, to name a few. According to one aspect, the values and/or patterns of the blood tests such as the inflammatory mediators is/are compared to the image(s) of physiologic perturbation or to the pattern(s) or values of at least one physiologic parameter, such as the pulse rate, respiration rate, and/or ventilation oximetry index to name a few. Upon the detection of an apparent relationship, the processor may automatically order a sufficing number of sequential blood tests to confirm that the pattern of the parameter is convergent with the pattern of the blood test thereby providing strong supporting evidence, reinforcing redundant evidence, that the physiologic parameter and the mediator have a common physiologic failure based linkage, such as the failure of sepsis for example. One embodiment extends that analysis to incorporate specialized inflammatory mediators into the moving picture of failure so that comprehensive comparison of the marker or indicator to the image of the physiologic parameters and treatment may be provided. One embodiment generates dynamic images of relational variations of a set of time series associated with a complex system to generate a real time motion picture of a failure of the system and/or of forces applied to the system and condenses the complex data of the EMR into a single motion picture of perturbations, treatments, physiologic responses, diagnostic testing, recoveries, diagnoses, missing data, patient locations, and/or other datasets and further provides treatment, and/or testing, alarms, notifications, diagnosis, and/or orders based on the motion pictures.

One embodiment provides a system and method for programmatic characterization of a plurality of related complex and dynamic processes, which; converts patterns along a plurality of parallel times series derived from each of the process into discrete objects, organizes these discrete objects into relational objects, and, organizes the relational objects to render a unifying programmatic image of a complex and dynamic process, and then, applies expert systems to automatically recognize images or image portions, or the specific motion pictures which are indicative of at least one failure of the complex processes and/or provides a relational object image generating and processing system to provide characterization and quantification of physiologic systems by generating an organized analytic construct defined by a time series matrix of relational objects.

Figure 1:
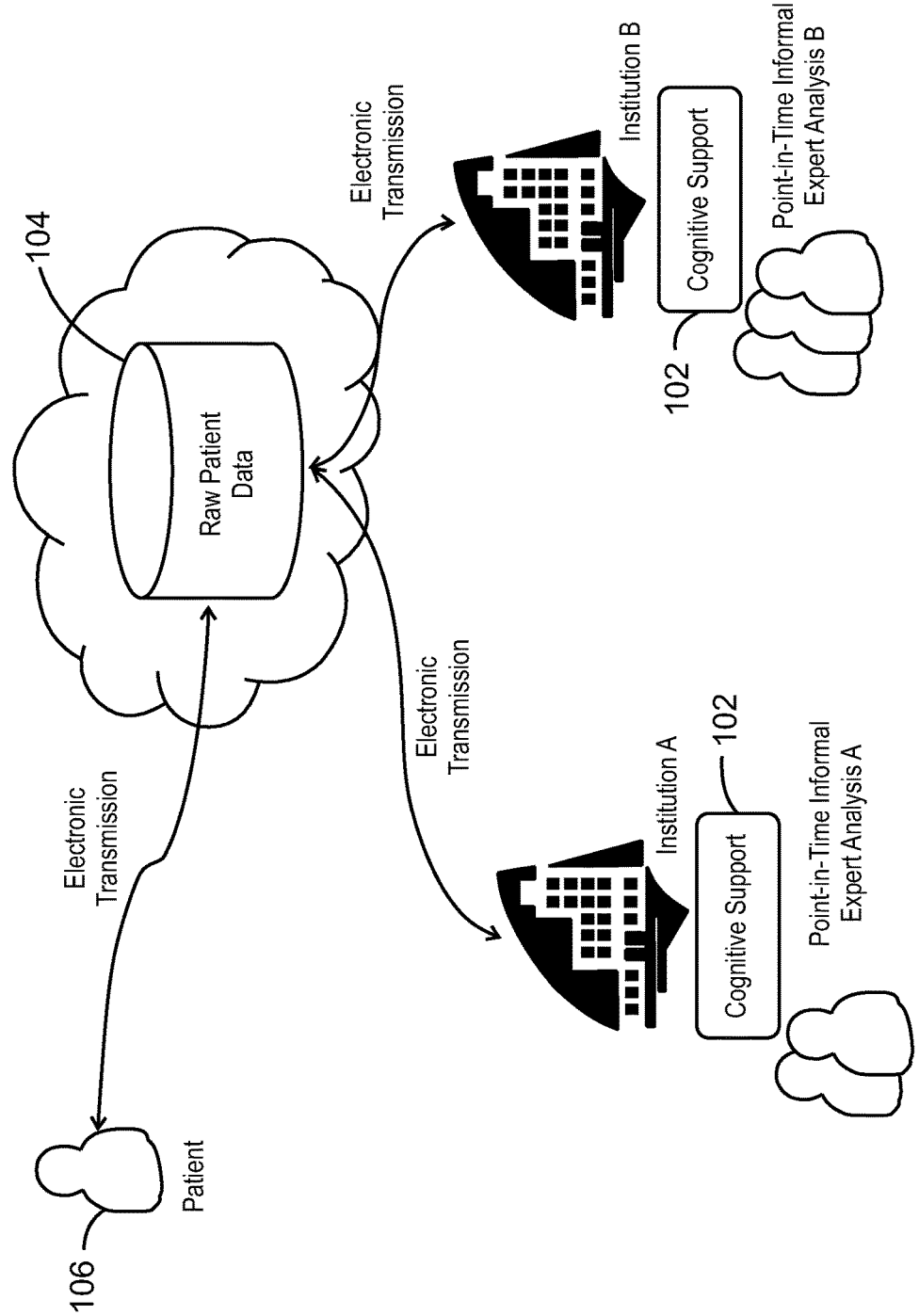
FIG. 1 depicts a conventional medical repository system with associated cognitive support.

Although the number of potential modes of failure is very high in any hospital environment, the occurrence of certain modes of failure is reasonably likely under a given set of circumstances in the hospital. A failure mode diagram illustrating common modes of failure given a combination of a group of diseases is shown in FIG. 1. The number of potential failures may be very large (in the hundreds) for a given patient in a hospital setting and the nurse or physician is often expected to monitor many such patients on the floor while timely detecting the failures such that the nurse is expected to timely detect even a single failure from as many as a thousand failures which may occur among the patients under his or her care. For this reason, processor based failure imaging and detection is desirable.

In one embodiment the processor 200 is programmed to differentiate in the display image binaries (which represent image components) from force binaries (which, in addition to representing image components may also be defined by the density modifying force exerted by the falpha on the theta or by the fsigma on the ftau). The display of the force binaries as overlays, or in-combination with the image binaries may be provided. The forces or the force binaries may be presented as a semi-transparent overlay.

The physician may have the option, as by right clicking on the displayed density modifying force or force binary of the PHM or on the display such as a weather pattern produced by the density modifying force or force binary, to identify or select the falpha and particularly the apical falpha likely inducing weather patterns or to select an action, such as testing, to identify the falpha. At the time of patient discharge a relational timed display and/or listing of the residual binaries without a solution may be provided. The physician may then select the falphas likely inducing the perturbations detected by the processor 200. Since, with more data and time, the processor 200 may identify the falphas and thereby find the solution for these binaries, additional information and further processing after discharge may disclose whether or not the physician's designations were correct. The processor 200 may be programmed to provide a context sensitive group of testing choices (as from a drop down menu) known to potentially identify one or more falphas which could have induced the detected theta.

The processor 200 may be programmed to automatically order future testing to determine the future of the falpha, or may be programmed to provide an option for the physician to instruct the processor 200 to ignore one or more of the forces. In one example, when there is sufficient time, without undue risk of diagnostic delay, to perform tests in sequence, the processor 200 may process a risk cost based analysis to determine the next tests to be performed. For example the processor 200 may rate the probability that the test will identify the falpha, rate the potential risk of the test, rate the risk of failure to perform the test, and rate the cost of the test. The processor 200 may be programmed to rate the risk of the test from 1 to 5 with 1 being the lowest risk, the risk of failure to rapidly diagnose rated from negative 1-negative 5 with the lowest risk being negative 1, the probability that the test will identify the falpha may be rated from 1-5 with the highest probability being 1, and the cost of the test from 1-5 with the highest cost being 1. The risk of the test or the risk of failure to rapidly diagnose may be weighted to provide 2-3 times its value. Alternatively another factor may be weighted. The test selected to order first may be the one with the lowest sum. (Alternatively non-invasive and minimal or non-irradiating tests may be prioritized and quantified separately from invasive tests because to place the do-no-harm doctrine as a prime objective.)

In an example a negative perturbation of venous platelet density is identified by the processor 200 along the PHM as a 10% decline in platelets over 24 hours with a fall slope of 5/6 per hour and an absolute fall of 20 from 200 to 180. The processor 200 searches for an falpha, for example, prior infusion of heparin, inflammatory augmentation, recent transfusion, recent treatment with clopidogrel, positive antinuclear antibody, to name a few and searches for other potential falpha or sentinel falpha along the PHM (which may include for example prior infusion of heparin and/or an evolving sepsis cascade). If the processor 200 identifies heparin infusion within the appropriate time, the processor 200 may be programmed to proceed with testing as a function of a threshold or a derivative of the combinations of the numbers or based on a pattern of the time series of the sum or a derivative of the combination of the numbers. For example the processor 200 may be programmed to proceed with ordering a test if the sum is less than 5. Platelet factor 4 is an expensive test which may be rated a 4 in terms of cost, but it is a simple blood test it has a low risk which may be rated as 1 in terms of risk. However, the risk of failure to diagnosis heparin induced thrombocytopenia is high but, if present, it is still very early so this may be rated as only negative 3 and finally the probability the test will be positive is low given the marginal decrease in platelets and brief decline so this may be rated as 5. The sum is 7, which is above the threshold so the processor 200 will not order the test unless overridden. The processor 200 may be programmed to calculate the time, as projected by the slope, wherein the sum would be 5 if the slope of the decline continued and to repeat the platelet count at that time and make another programmed decision about which tests to order (if any). These ratings may be heuristically derived by expert panels and then readjusted as determined by assessment of cost and performance associated with the ratings.

Even seemingly minor density modifying forces may be deadly because they may irreversibly distort the PHM. This is especially true if the forces continue unabated or progressively increase (as may be the case when a self-replicating microbe has invaded the human, distorting the PHM). Often only a few organisms initially invade the PHM and produce minimal distortion of the PHM. Distortion of the defense (immune) system of the PHM often comprise the first fbetas and falphas which are readily detectable when the numbers of organism which have invaded the PHM is still too low for detection even by blood polymerase chain reaction testing. Here it is the dynamic distortion of the PHM, and not any single or relational density value, which best characterizes the state and cause of invasion. As the organisms increase in numbers, the PHM distortion they induce in the immune system increases and the invasive proteins generated by the organism may induce PHM distortion, for example in the clotting system. Each distortion in this comprehensively connected PHM pulls or pushes on another portion of the PHM dynamically distorting that portion. Each time a distortion occurs in the PHM, dynamic compensatory perturbation forces may be triggered to protect the PHM. In addition dynamic recovery forces may also be triggered to move the PHM into a more life favorable matrix configuration which may not be the original configuration of the PHM. Compensating forces, while responsive to perturbations are different from recoveries in that they will not mitigate the falpha but are rather temporizing and often simply mitigate the theta producing a false sense of recovery. In one embodiment, compensating forces and compensating events comprise companion falpha and fbeta to the perturbation being compensated. The severity vector of the compensation fbeta may be combined by the processor 200 with the severity vector of the primary perturbation fbeta to reveal the actual severity induced by the combined perturbation and compensating perturbation.

Upon detection of early distortion of the PHM, the risk of excessive or irreversible distortion of the PHM posed by one or more perturbation forces (such as that induced by invasive bacteria) may be reduced by empiric treatment in programmed response to one or more fbetas and/or falphas or larger pattern along the PHM. In one embodiment, perturbation force binaries have four basic states presented in order of increasing risk; solved and falpha and/or theta treated, unsolved but potential falpha and/or theta empirically treated (as by processor ordered and processor confirmed treatment), unsolved and potential falpha and/or fbeta untreated, solved but falpha and/or fbeta untreated. The last two risk categories may pose an equivalent risk.

The processor 200 may be programmed to detect a new increase in binaries without a solution and identify as by display when an increase and/or a cascading matrix of such binaries occurs and to indicate the presence of the development of a new undiagnosed condition or complication and to suggest or automatically order testing in search of the missing binary components which may provide the solutions for the binaries. Binaries or cascades of such binaries without a solution may be severity indexed based on the potential risk associated with the binaries and the index outputted.

In an example, a negative perturbation of the density of venous H2CO3 in combination with a preceding positive density perturbation of venous bands, a subsequent negative perturbation of the density of venous platelets, may be displayed on the PHM as either as a grouping of perturbation image binaries, perturbation force binaries, or both. This grouping of binaries, if unsolved and not empirically treated, has a high severity risk indicating that a rapid solution comprising determination of the falphas (one of which may be sepsis) is mandated. With these binaries and the cascade distorting the PHM, the risk of failure to rapidly diagnose is high, for this reason the processor 200 is programmed so many tests will be immediately ordered by the processor 200.

Domain of Sets of Biologic Particle Densities of Living Human Beings

A formal domain exits which comprises measurements of compartmentalized biologic particle densities in human beings. This is a primary domain in the field of medical diagnostics. However, data sets of this domain generally lack formal objective mathematical solutions so that large sets of data (such as those in the cloud or on hospital servers), existing with little or no mathematical solution, is a normal final state of data for this domain. For a typical data set in this domain, the lack of a mathematical solution is supplemented by subjective solutions to render highly variable diagnostic results. This renders a domain wherein: a perpetual state of even a large data set with little or no mathematical solution is typical; simple data points existing as "numbers on a page" are acceptable final data formats; and incomplete data sets commonly exist without being so identified.

This explains the crisis which exits in this domain. There is a need to define a formal mathematical solution for data sets in this domain.

Axioms of the Domain of Sets of Biologic Particle Densities of Living Human Beings Given a biologic particle density set D of a living human there exists a force set F, whose members induced exactly those members of D.

Given a biologic particle density set D there exists a probabilistic force set P(F), whose members have a probability >0 of having induced exactly those members of D.

Given a collection of biologic particle density sets there exists a normal set N, whose members are exactly within a phenotypically normal range.

Given a normal set N there exists a normal force set $F_{ii}$, whose members induced exactly those members of N.

Given a normal set N, there exists a probabilistic force set $P(F_n)$, whose members have a probability >0 of having induced exactly those members of N.

Given a collection of biologic particle density sets of a living human there exists a perturbed set P, whose members are not the same as the members of set N.

Given a perturbation set P there exists a variation force set $F_v$, whose members induced exactly those members of P.

Given a perturbation set P there exists a probabilistic variation force set $P(F_v)$, whose members have a probability >0 of having induced exactly those members of P.

Given a collection of density sets of biologic particle density sets of a living human there exists a recovery set R, whose members are not the same as the either the members of set N or the members of set P.

Given a recovery set R there exists a recovery force set $F_r$, whose members induced exactly those members of R.

Given a recovery set R, there exists a probabilistic recovery force set $P(F_r)$, whose members have a probability >0 of having induced exactly those members of R.

According to one embodiment, this set of axioms, analysis may proceed with standard mathematical methods of reduction, inference, simplification and synthesis to engage the science of human medical diagnosis through application to the parallel human time matrix.

In an embodiment, a display is provided indicative of a PHM comprised of solved perturbation image binaries; recovery image binaries, perturbation force binaries, and recovery force binaries, as well as unsolved binaries. Compensating image or force perturbation binaries, which may comprise a sub class of perturbation binaries, may also be uniquely designated in the display so that the severity of compensatory perturbation force and/or compensatory perturbation may be readily visualized. Since in response to severe r progressive perturbations, compensation is often limited in severity and time the processor 200 may show a display indicative of the severity of compensatory perturbation in relation to its projected limits. Binaries and/or the graphical representations derived from them (such as weather map type images) may have a different colors, or other markings to differentiate different binaries and between solved and unsolved binaries or the storm cells associated with different binaries.

While the ialpha of an image binary is not generally a medical condition (although it may be), at least one falpha of a force binary is often a medical diagnosis. A plurality of force binaries may be generated with the same falpha or the same theta. For example, one perturbation force binary may have a theta comprising an increased density of lactate in the venous compartment and/or metabolic region of the PHM and its falpha comprising the diagnosis of sepsis, while a second perturbation force binary may be comprised of the same increased density of lactate but with an falpha comprising a decreased density of central venous oxygen, while a third perturbation force binary may be again comprised of the same increased density of lactate but with an falpha comprising a decreased cardiac output. The decreased cardiac output may also be the falpha for the theta comprising the aforementioned decrease in density of central venous oxygen. Furthermore a decrease in density of venous H2CO3 may be the theta for the three falpha comprised of; increased density of lactate, the decrease in density of central venous oxygen and the decrease in cardiac output. Finally the low central venous oxygen density may be an theta for the decrease in cardiac output. A low vascular volume may be one falpha for the theta which comprises a decrease in cardiac output and sepsis may be another falpha for that same theta. Finally active sepsis may be an falpha of perturbation force binaries for each of these fbetas. In this way, an embodiment generates cascades of perturbation force binaries comprising falphas (force inducers) and fbetas (for example particle density changes) responsive to the force inducers.

These linked sequences and cascades of binaries define the mechanisms and physiologic basis for the operative pathologic process and source of the primary distortion of the PHM, which for example with sepsis as an apical falpha comprises the common or global falpha for the entire perturbation force cascade. However although sepsis may be designated as an apical falpha, sepsis cannot comprise a completed proximal end of a cascade. The cause of the sepsis (the triggering event, the invasive organism, and the primary and secondary compartments invaded) are all potential proximal falphas for systemic sepsis which need to be solved for the binary which contains sepsis as the theta to have a designated solution by the processor 200.

The processor 200 is programmed to follow the cascade back in time to its origin to detect the apical falpha and also the actions (such as central line insertion or surgery which may have triggered the apical falpha.

In one embodiment a single diagnosis (such as active sepsis) may comprise an apical falpha for each component of a perturbation force binary cascade and a single treatment, such as penicillin infusion may comprise an apical fsigma for each component of the subsequent recovery force cascade. Many other falphas will also be identified for smaller patterns of fbetas or for individual fbetas.

Many diagnoses which comprise active disease have companion events embedded within the PHM, which related to treatment or to another condition or sprigs of early recovery from another condition. In an example, perturbations which would not be expected to be induced by the force of active sepsis (such as a sever fall in density of venous potassium) will not, if detected, be included in the cascade of perturbation force binaries having an falpha of active sepsis and despite the detection of a massive sepsis cascade, the processor 200 will search for another falpha to explain the severe fall in density of venous potassium. The detected falpha may be, for example, the administration of furosemide anther force.

In one embodiment all particle densities are designated as falling into at least a portion of the following categories; particle density in normal population range, particle density in the phenotypic range for the patient, particle density chronically stable and elevated or decreased in relation to phenotypic range, particle density chronically changing and elevated or decreased in relation to phenotypic range, particle density high or low in relation to phenotypic range but stability is unknown, particle density acutely increasing or decreasing. Any of these may be identified by the processor 200 as ibetas or fbetas. In this way the processor 200 tracks all densities and density variations, establishes the phenotypic density range or another range for each patient and determines when the densities have been perturbed and searches for one or more falphas which may have induced that perturbation. The processor 200 may generate outputs for healthcare workers wherein all densities have the above designations and densities which are not stable are flagged and automatically tracked by testing. The timing of testing may be, for example, defined by the rate of change and/or the falpha (if known), or by other healthcare worker or statistically testing defined protocols. The above categorization of betas and testing protocols, according to some embodiments, provides a mechanism to prevent density changes from proceeding without, at least, process based analysis of that density change and healthcare worker notification, if indicated.

In one embodiment, the healthcare worker may choose to visualize at least one time segment of the PHM in a format such as a color radar weather map as derived from solved and/or unsolved perturbation image binaries, recovery image binaries, perturbation force binaries, and/or recovery force. Drill downs requesting the binary information relating to the patient storm cells may reveal the spatial and temporal pattern relationships of both density modifying forces and density changes. Drill downs, as by touching a storm cell, or passing a pointer or mouse over a storm cell requesting the image binary information relating to the patient storm cells may reveal the spatial and temporal pattern relationships of events, patterns and cascades comprising the image of a patient's condition and care.

Perturbation of the phenotypic dynamic relational range and/or a pattern of densities may also comprise an theta or ibeta and a force modifying one or more components of the dynamic relational range or pattern of densities may be a falpha producing a perturbation force binary of the dynamic relational density range or density pattern.

In one embodiment, other events other than values or perturbations of particle densities may be included as fbetas or ibetas of the PHM. For example the frequency or consistency of bowel movements may be entered as by subjective assessment by a nurse or by sensor on the toilet which automatically detects bowel movement frequency and/or consistency. If diarrhea is identified by the nurse or detected by the sensor this becomes the theta and the processor 200 searches for an falpha. If, for example, recent prior or present cephalosporin administration is detected along the PHM this may trigger an order for example *Clostridium difficile* testing on the stool by polymerase chain reaction. If this testing is positive then both the cephalosporin and the *Clostridium difficile* becomes the falphas for the theta diarrhea. Together they comprise two perturbation force binaries as the cephalosporin will become the falpha for the theta comprising a minimum particle density of *Clostridium difficile* in the large bowel compartment. The PHM processor 200 may be programmed to check the PHM for allergies and order treatment if protocolized to do so, which may include discontinuation of the cephalosporin or substitution with another antibiotic if the PHM suggests incompletely treated infection requiring continued antibiotics. The perturbation force binary now has a solution and both the theta and falpha of the binary are under treatment. The processor 200 will then search for recovery of the fbetas (for example recovery of the diarrhea, and a fall of in *Clostridium difficile* in the stool).

If despite the fsigma, which may comprise the administration of vancomycin, discontinuation of the cephalosporin and/or other recovery inducing force, the ftau is not detected (recovery does not occur within the expected time) then the recovery force binary is considered unsolved and the perturbation force binary is designated as a perturbation force binary with recovery failure. Processor 200 identification of perturbation force binaries with recovery failure generates an output indicative of recovery failure despite treatment for the healthcare workers.

In another example, an increase in venous density (for example form zero density) of chemotherapy as indicated by chemotherapy infusion may be designated as an falpha. If the chemotherapy is known to be myelosuppressive one expected theta of a perturbation force binary may include a decrease in density of neutrophils over a time period following the chemotherapy. The processor 200 projects the expected range of values and slope of the theta over time as for example determined by population studies. A change in neutrophil density and a slope of the change falling within this range comprises a solved perturbation force binary whereas a neutrophil density change or lack thereof or slope which is out of this range comprises an unsolved or incompletely solved perturbation force binary. The incomplete perturbation force binary then becomes the theta for which the processor 200 may be programmed to detect the falphas by ordering additional or more frequent testing or other diagnostic or therapeutic action, such as blood or fluid polymerase chain reaction testing, blood cultures, and/or the administration of granulocyte growth factors provided the processor identifies no contraindication. In this manner all chemotherapeutic administration events are processed to assure that the perturbation force binaries are promptly solved and recovery detected and assured, if possible.

In another similar example, a surgical procedure may comprise an falpha, which is expected to produce a range of thetas including, for example, a modest increase in venous density of neutrophils and a decrease in venous density of lymphocytes or of one group of lymphocytes such as T helper lymphocytes (as for example determined by population studies for that surgical procedure). The processor 200 projects the expected range of values and slope of the thetas over time as for example determined by population studies. A rise in venous neutrophil and a fall in lymphocyte density and slopes of rise and fall within the expected ranges comprises solved perturbation force binaries whereas a neutrophil density change or lymphocyte change or slopes which is out of this range, comprises an unsolved or incompletely solved perturbation force binary.

Likewise after surgery a segment of the PHM with a change in the density of bands outside the expect range comprises an unsolved or incompletely solved perturbation force binary. The presence of one or more unsolved perturbation force binaries may comprise new falphas which trigger additional or more fbetas and falphas such as testing or other diagnostic or therapeutic action, such as polymerase chain reaction testing, blood cultures, and/or empiric antibiotic therapy. The binary linkages are continued until the recovery force binaries are solved or otherwise resolved along the post-surgical segment of the PHM.

In one embodiment one or more human genes, gene variations, or mutations may comprise the falpha (the force inducer) for a given particle density or relational density change. The identification of a density which is outside or nearly outside the statistical range identified for the relevant population or demonstrating a dynamic particle density response to a force (such as the venous density of a pharmaceutical) which is outside the range which is expected statistically in response to that force may generate a review a comparison with the genetic code of the patient.

In one embodiment the PHM processor 200 is applied to test the relationship of a wide range of human genes to the resting particle densities and/or particle density variations in response to at least one force. Each gene (which may be a mutated gene) may be the equivalent of a fixed step function on the matrix as for example is the genetic sex of the patient. Perturbation force binaries wherein theta are at least one of density values, density variations, relational densities, or cascades of density variations, are combined with each known gene of the patient as the falpha to produce hybrid force binaries containing genetic information. The hybrid force binaries may then be statistically evaluated to determine if specific genes or clustering of genes are associated with one or more specific perturbation force binaries, one or more density modifying forces, or one or more thetas.

In one embodiment when multiple perturbation force binaries are identified with a single theta instance the processor 200 may aggregate the forces to determine whether a possible complete or partial solution has been identified.

In one embodiment, the health care worker may be provided with an environment to explore "what if" scenarios to examine what conditions may adequately solve the perturbation force binaries present. In this way, the health care worker may narrow proposed solutions even before lab results have been returned. For example, a health care worker may believe that a force would solve a binary but not realize that the severity of the theta cannot be adequately explained by the proposed falpha. In this way, simplistic or inadequate explanations which may, without an environment containing the rigor of force aggregation and projection, have been considered possible answers can, through the application of the PHM be quickly ruled out or considered suspect.

In one embodiment, the solution of the force binary is designated as a function which compares properties of the falpha or fsigma to properties of the theta or ftau in, for example, a ratio. For example, the slope of the theta may be defined in relationship to the magnitude of the falpha. In the case in which the falpha is a diagnosis, ranges may be provided for the severity of the diagnosis in a manner discussed previously for forces perturbations and recoveries.

Organ or cellular failure may first induce a density modifying force on a passive (non or minimally force inducing) particle which provides indication of the organ dysfunction or failure and may therefore be designated as a sentinel falpha. Perturbation of the density of a sentinel falpha indicates that a density modifying force is likely being generated (or may be generated in the future) on at least one other particle density.

In one embodiment, the time relationship between the falpha and the theta may include a phase shift based on presentation delay. If the mechanism of acquiring the density values includes a delay, this delay may be included in the time relationship and may even include the possibility that the theta may be identified before the falpha presents to the system.

According to some embodiments, the value of a test, such as a measure of a compartmental density of a biologic particle, as an "enhancer" of the probability that a given clinical condition is present, is a function of the effect the incorporation of the test into the PHM has on the probability of the PHM for that condition at the time of incorporation. In other words, the sensitivity and specificity of a measured biologic particle density for a condition, such as sepsis, is a function of the sensitivity and specificity of the PHM which incorporates the particle density measure, minus the sensitivity and specificity of the PHM when the has not been so incorporated. Using the PHM, the value of a diagnostic test is defined by its ability to more completely fill in the missing components of the dynamic PHM image so that the image is more sensitive and/or specific for a clinical condition than was the original image which did not incorporate the test.

In one embodiment the PHM includes a probability matrix as one of its components which may be integrated with the other components of the PHM. The probability matrix comprises a matrix of time series wherein each times series is comprised of the timed probabilities of a condition (for example sepsis) as defined by the PHM (including the other probability time series).

The time series matrix of probabilities, correlation, and/or probability discriminating measure (such as sensitivity and/or specificity) is preferably objectified and analyzed to define probability perturbations (theta) and to identify the forces (falpha) inducing those perturbations of probability (such as a diagnostic test result, historical or physical finding). For example, the processor 200 identifies a 30% increase in specificity of a time segment PHM for sepsis after a high density of procalcitonin has been added to the PHM, in this case procalcitonin is identified as the force (the falpha) inducing the positive perturbation (the (beta) along the sepsis probability time series of the PHM. A positive polymerase chain reaction test for bacterial DNA in venous blood may be a very strong falpha inducing a positive perturbation in the objectified sepsis probability time-series of the PHM sufficient to alter treatment and testing.

According to one embodiment of a method of some embodiments, clinical trials to determine at least one diagnostic probability or discriminating measure (such as sensitivity and/or specificity) for example, of a new test are performed using the PHM. One method for evaluating the at least one value indicative of the diagnostic discriminating value of a diagnostic test comprises; obtaining medical data, which may include for example, genetic, historical, or test derived data, from a set of patients, generating a PHM for each patient derived from the medical data, determining a first result comprised of the probability or discriminating measure of a condition using a PHM which does not incorporate the result of the diagnostic test, incorporating the result of the diagnostic test into the PHM, determining a second result comprised of the probability or discriminating measure of a condition using the PHM having the diagnostic test incorporated into the PHM, comparing the first result to the second result and calculating a comparison result and defining at least one diagnostic probability or discriminating measure as a function of the comparison result. The comparison result may for example be derived by subtracting the first result for the second result.

After a biologic particle has been sampled its probabilistic value begins to move away from the sample value and defines a probabilistic range of values which may be considered a probabilistic wave function of the particle. The distance between the sampled value and the probabilistic range of values after a given time interval will be affected by the clinical condition of the patient.

One approach for projecting a path of the PHM and particularly the path of a distortion in the PHM and for determine a patient specific frequency of automatically ordered lab testing is to calculate a potential worst case path or value of a parameter and then identify the retesting time based on the minimum change of the parameter which would have clinical relevance given the potential condition or conditions identified by the processor 200. For example, if the processor 200 has identified severe sepsis as a potential condition, then a projected bicarbonate (or other lab values) may be calculated by Equation 1:

$$V_p = V_s + T_D(dV/t) + T_i(dV/t) \qquad \text{Eq(1)}$$

Where:
$V_p$ is the projected value of the parameter at the projected time;
$T_i$ is the time interval between the last sampling time and the projected time;
$T_D$ is the delay between the sampling time and the display time;
$V_s$ is the value of the parameter at the sampling time (this may not be known until later if there is a transport and/or testing delay); and
$_dV/t$ is the worst case or near worst case slope of the parameter given the condition(s) identified as potentially present by the processor 200 (such as sepsis).

An efficient timing of retesting which would enhances the ability to early detect change may be made by setting the next sampling time to an interval calculated from specifying the minimum or maximum (depending on the polarity of the trajectory) of the projected value which would (if known) affect diagnostic or therapeutic action given the condition(s) identified as potentially present by the processor 200. For example, suppose the bicarbonate value at the sampling time (Vs) was 20 and is identified by the processor 200 as falling at a rate of 0.5 meq/hour and the processor 200 further identified the image as representing a high probability that sepsis is present, yet the processor 200 identifies the next test for bicarbonate has been ordered by the physician at 8 hours and the average, worst 10 percentile (or other measure), of delay from sampling time to display time (TD) is known or calculated to be 1 hour for this particular hospital ward. Then in one embodiment the processor 200 may be programmed to identify an improved sampling interval based on a projected "near worst case" bicarbonate fall of 1 meq/hour for the condition of sepsis, and adjust the repeat bicarbonate testing to 2 hours since a fall in bicarbonate to 17 (the value which could reasonably be present in 3 hours (sampling interval plus delay interval) would (if known) affect diagnostic or therapeutic action given the condition(s) identified as potentially present by the processor 200 (in this case sepsis). In the alternative, when managing this patient without the processor 200 intervention of some embodiments, the bicarbonate could have fallen to 11 (before outputted as 12 on the display) and this value in this range may result in death (perhaps before the sample is even taken). As demonstrated in this example, the condition or pattern specific projection of individual parameter values provides both warning and a means to improve sampling time and therefore the diagnostic utility of the motion image and improved protocolization of treatment. Furthermore the projection of multiple parameters may be used to render one or more possible paths which the patient storm may take if, for example, intervention in not provided.

The processor 200 may be further programmed to, based on the diagnosed clinical condition, or a distortion along the PHM, calculate or project a potential path range of the first particle density, and then calculate or project at least one other path range of at least a second particle density based on the first particle path and the clinical condition and or distortion. The processor 200 may project or calculate a cascade of paths based on the first particle path and the clinical condition and or distortion. The processor 200 may be programmed to generate a color rendering of an image of the matrix and to project the path as a color rendering. The rendering may have an appearance of radar weather display and the path may be projected as a color rendering, which may be a time lapsable motion image having an appearance of a path of weather progression over time.

In an example, based on the projections for H2CO3 provided in the above example, in a patient with sepsis, the processor 200 may project a H2CO3 of 12 in 12 given a projected fall rate of based on the present rate of fall and a value of 12 in 6 hours based on a "near worst case" fall rate. The projected respiratory rate when the H2CO3 is 12 likely exceeds 30. Therefore a rate range may be projected by placing the rate at 30-36 in 12 hours for a present rate based display and at 30-36 in 6 hours and the paths connected back by the processor 200 to the instant respiratory rate on the display. A similar approach may be taken for heart rate which would be projected in an individual less than 60 without heart disease or beta blocker to be about 130-140 when the H2CO3 is 12. These projections need not be precise as they are presented to warn of the likely dynamic consequence associated inaction in the face of this projected perturbation in particle density and to teach the physician to think of the projected future based on the dynamics of the particles in the present and the disease or disorder present.

The processor 200 may be programmed to project the time range of arrest or intubation based on these parameters. Similar projections may be made for example the anion gap anion may be projected and the dyspnea index.

In one embodiment the efficiency of testing is quantified. In one embodiment the pattern of testing is analyzed to determine the pattern of testing and the pattern of testing is analyzed to determine the correctness, timeliness, and the efficiency of testing. The pattern of testing includes, for example the distribution and timed frequency of a single type of test, or all tests, particularly in relation to a clinical condition such as sepsis. According to one aspect of some embodiments, the processor 200 identifies the pattern of distribution of testing for sepsis. Patterns of sepsis diagnosis associated with a favorable outcome are then compared to identify the most efficient patterns such as a pattern which demonstrates a high frequency of tests early along the sepsis pattern or a pattern which comprise a high testing frequency maintained until the onset of recovery has been identified or a decision to reduce care due to futility or family preference has been specified.

One processing method for optimizing the detection of sepsis comprises, generating a distribution of testing in relation to time and/or at least a portion of the image of the sepsis, comparing the distribution to destitutions of testing associated with a favorable outcome, comparing the cost of testing, identifying at least one testing distribution for sepsis, which has a favorable cost and outcome. The method may compare the distribution of the number of tests per unit time and the distributions of each type of group of tests per unit time in relation to the onset of the sepsis pattern or another aspect or portion of the sepsis image.

In one embodiment the relationship between binaries, and in particular, falphas and their fbetas are non-consuming. In other words, the processor 200 creates binaries of all possible connections rather than the first or a statistically preferred connection. Once all possible connections are created (i.e. those that meet the criteria as specified) then the processor 200 may further characterize the set of possible falphas per theta to indicate a continuum of probabilities per binary identified. This continuum may be constructed using the probability matrix as described above as well as other mechanisms of proximity, similarity of severity to name a few. Further, the PHM processor 200, once a non-consuming pass has been accomplished, may include a second consuming pass in which at least one "best fit" models is proposed. In one embodiment, the healthcare worker is provided with an environment in which a set of "best fit" models are presented. The healthcare worker may interact with the models through gestures using a mouse, touch surface, keyboard, and/or natural interface to name a few. For example, the healthcare worker may identify links to be "suspect" or otherwise unlikely. As well, the healthcare worker may indicate a link as "highly likely" or otherwise indicated as preferred. The processor 200 continuously processes the "best fit" algorithms given the new weights provided by the healthcare worker. Outputs of the "best fit" models would provide transparency indicating the alternatives that were rejected as well as the results of the healthcare worker gestures which were included in the weighting of diagnostic options.

In an alternative embodiment, the healthcare worker and/or student is provided with an environment presenting the model with no force designations, or only very low level force designations. The healthcare worker and/or student may then "solve" the model by selecting forces that satisfy the extant occurrences. One or more diagnosis may be added at a specific point in time to indicate the apical force.

In one embodiment, a perturbation (and/or a force, recovery, binary, quaternary or polyquaternary) is programmed to be aware of its state as a solved or unsolved perturbation and to have a "seeking state" wherein it seeks its binary and quaternary links. The seeking state may be defined by game theory and the strength of the seeking may be defined by the type of perturbation and the potential time dependency and severity of the risk associated with the potential solutions. As other seeking perturbations find their forces and recoveries, the new binaries or quaternaries become potential matches for the seeking perturbation. The seeking state may continue after one or more solutions. The seeking and self-solving binaries and quaternaries and manual, semi-manual, or automatic distortion building also provides an education function. This education may be provided as a video game for dynamically building PHM distortions (for example theta cascades or polyquaternaries) and rendering a diagnosis and treatment as a function of the building. With this game, the student is learning a new science of computer assisted dynamic relational diagnostics.

In one example of such a video game, the student is first presented with an PHM to review for a time interval, the PHM provides a history by going back in time along the PHM or viewing historical segments which may be compressed or time-lapsed and by reading the linked narratives or attached digital files. For those who may be inclined, the PHM may also be viewed as a naked objectified matrix (as for example in FIG. 6), with the forces, perturbations, and recoveries, and their features identified and color coded for severity. The student may use supplemental viewers presenting for example weather maps or other dynamic views, examine the raw data in tabular form or as manipulate able time series matrices.

After preparing, the student is then shown the PHM with a dynamic distortion (which may change more quickly that the real distortion) emerging which will generally be comprised of only perturbations such as particle density perturbations. The student can link a sufficient portion of the perturbations and recoveries if any for the student to identify a disease or disorder which likely as induced the polyquaternary. The student is expected, upon seeing the primers, to recognize the need for other tests, order them, and link the new test results in the PHM to grow the distortion (for example the polyquaternary). The distortion (and the polyquaternary if the entire distortion is being built) at this time will be incomplete and comprised primarily of linked perturbations. The student is then expected to solve the polyquaternary (the distortion of the PHM), by for example inserting the correct apical falpha which comprises the final diagnostic step in the solution and the insert the correct treatment falpha, which may comprise the final solution step. Upon insertion of the treatment, the game may then insert a range of other forces along the distortion and present a time lapse of the PHM showing the anticipated recovery and resolution of the distortion of the PHM. In one scenario, a new distortion (as for example induced by an adverse drug reaction) may arise and the student will need to solve this distortion without allowing the original distortion from recurring.

In one embodiment the processor 200 may generate a dynamic two or three dimensional parallel construct from medical data, and to analyze the construct for dynamic distortions indicative of at least one of disease, drug reactions, age related declines in function, or clinical failures, the construct comprising a highly organized time matrix comprised of grouped, bonded, linked, related, encapsulated, or otherwise connected; perturbations, perturbation forces, recoveries, and recovery forces. The processor 200 may generate a time-matrix construct of electronic medical data comprised of perturbation of particle densities linked to the forces which may have induced the perturbations.

In one embodiment a processor 200 may be programmed to generate one processor 200 programmed to generate a time-matrix construct of electronic medical data comprised of perturbation of particle densities linked to the forces which may have induced the perturbations. Alternately or in combination a processor 200 may be programmed to generate an image of electronic medical data comprised of dynamic color displays responsive to linked dynamic quaternaries comprised of perturbations, perturbation forces, recoveries, and recovery forces.

A processor 200 may be programmed to generate a time matrix which comprises linked particle densities, exogenous forces, endogenous forces, perturbations, and recoveries and an analysis comprising; detection, identification, quantification, and tracking of cascading perturbations, the forces inducing the cascading perturbations, as well as triggering events (such as a surgical procedure) which may have induced the forces. Alternatively or in combination at least one processor 200 may be programmed to process medical data, detect a grouping of linked perturbations and perturbation forces, detect a cascade comprised of the grouping, search the medical data for at least one apical force which induced the cascade, and output an indication of the apical force.

A processor 200 programmed to process medical data, generate a time matrix comprised of the medical data, detect a grouping of linked perturbations and perturbation forces along the time matrix, detect a cascade comprised of the grouping among the time matrix, detect a grouping of linked recoveries and recovery forces along the time matrix, and output a dynamic timed image responsive to the time matrix. Alternatively or in combination at least one processor 200 may be programmed to convert the medical data into a time series matrix of objects comprised of linked objects of binaries comprised of perturbations and the perturbation forces which induced the perturbations, and recoveries, and the recovery forces, and recovery forces which induced the recoveries, store the time series matrix in a data repository, and periodically adding new binaries onto the matrix over time.

A processor 200 may be programmed to process medical data, generate a time matrix comprised of the medical data, detect a grouping of linked perturbations and perturbation forces along the time matrix, identify linkages which comprise history primers and, upon the detection of one or more primers generate one or more questions for the patient to focus the history in response to the linkages. Alternatively or in combination at least one processor 200 may be programmed to identify linkages which comprise image primers and, upon the detection of one or more image primers generate one or more tests to be performed on the patient to complete the image.

One processor 200 may be programmed to generate an image of a patient's medical data comprised of at least one perturbations, perturbation cascade, force binary, force binary cascade, quaternary, or polyquaternary. The processor 200 may generate a parallel construct such as a time matrix of a patient's medical data comprised of a plurality of linked binaries wherein each binary is comprised of a perturbation and the force which induced the perturbation, or wherein each binary is comprised of a perturbation and the force which induced the perturbation, or wherein each binary is comprised of a perturbation and the force which induced the perturbation.

A processor 200 may be programmed to order tests based on detection of at least one force binary, force binary cascade, quaternary, or poly quaternary. The processor 200 may generate an image of a patient's medical data comprised of at least one perturbations, perturbation cascade, force binary, force binary cascade, quaternary, or polyquaternary, and identify an image primer comprising a partial image of a clinical condition, and order tests and/or treatment based on detection of the image primer to a render sufficient portion of the image to identify the image and/or to treat the likely condition inducing the image. One embodiment comprises a processor 200 programmed to generate a time matrix comprised of force binaries, the processor 200 further being programmed to provide a process for linking of lab values in the time matrix to build a distortion so that the student may learn to construct mental images of the dynamic building process of human pathophysiologic distortions in response to disease or adverse drug reactions.

A processor 200 may be to identify a clinical condition or pattern, based on the clinical condition or pattern calculate a potential worst case path or value of the lab value, identify the retesting time based on the minimum change of the parameter which would have clinical relevance and which may include the expected delay in lab reporting in relation to the ordered testing time, and order the lab test for a future time, based on the calculated retesting time.

A processor 200 may be programmed to identify the clinical condition or pattern, and based on the clinical condition or pattern calculate or project a potential path range over time of at least a first particle density, and output the expected path range of the first particle density on a display. The processor 200 may be further programmed to, based on the clinical condition or pattern, calculate or project a potential path range of the first particle density, calculate or project at least one other path range of at least a second particle density based on the first particle path.

The processor 200 may be further programmed to, based on the clinical condition or pattern, calculate a potential path range of at least a first particle density, and calculate a plurality of path ranges for a plurality of other particle densities based on the clinical condition and the first particle pathway. The processor 200 may be further programmed to, based on the clinical condition or pattern, calculate a potential path range of at least a first particle density and calculate a path range for a cascade of particle densities based on the clinical condition or pattern and the calculated or projected path range of the first particle density.

One processor 200 may programmed to compose interconnected cascades of physiological occurrences by combining into a quaternary four elements or objects comprising, a perturbation, at least one perturbation force which is capable of inducing and may have induced the perturbation, a recovery, at least one recovery force which is capable of inducing and may have induced the perturbation. The quaternary may be defined or its construction triggered by the detection of at one of the elements. The quaternary may be characterized as solved or unsolved. A quaternary may be are considered solved when all four elements are included, the collection of perturbation forces is determined to be compatible with the perturbation, and the collection of recovery forces is determined to be compatible with the recovery. A perturbation in one quaternary may be a perturbation force in another quaternary. A perturbation in one quaternary may be a recovery force in another quaternary. Any element in a quaternary may also be any element in a different quaternary. Interconnected cascades of quaternaries may be identified as candidate causation models for a patient condition. At least one candidate apical force 700 may be determined as the first perturbation force within a cascade. The identification of apical force may 700 be used by the processor 200 to identify or produce a diagnosis. At least one causation model may be displayed to a healthcare worker. At least two causation models may be compared. At least one preferred or "best fit" causation model may be determined. Unsolved quaternaries such as 702A and 702B of FIG. 7 can be displayed and/or initiate testing or a change in frequency of testing and/or be tracked as a time series and/or initiate an alarm. Solved and unsolved quaternaries 702A and 702B are identified on a color weather map visualization. A healthcare worker may select and/or weight the solution to a perturbation and/or recovery.

As discussed, in one embodiment perturbations, recoveries, binaries, quaternaries and polyquaternaries have seeking states and non-seeking states. The "seeking gravity" of the state can depend on factors such as risk, cost of finding solutions, and/or other factors. A high number of unsolved perturbations or perturbations with a large "mass" (as defined, for example by a potentially high risk), generate an "unstable" image with high internal gravitations forces. The image is stabilized when the seeking state of the perturbations is mitigated or resolved by either finding the matches or by being instructed (manually or automatically, as by internal "seeking buffers") to stop seeking.

In one embodiment a game can be constructed to show how the program functions and to teach the pathophysiology of distortions. The program can have a "game mode" allowing insertion of real or simulated physiologic data to generate a plurality of perturbations and forces. At least a portion of these will have no solutions so they will begin seeking. The presence of seeking perturbations can be designated by moving or otherwise enhanced graphical avatars, geometric shapes, or icons. As a first perturbation finds its match(es) a resulting solved binary and/or quaternary (which may be seeking) is generated. A second seeking perturbations may then find the solved binary and/or quaternary as its solution. This may produce a automatically growing cascade comprising a global solution and relieving the gravitational instability. All of this can occur on a graphical image building a moving image as the components seek each other and come together to for a solved game.

In one embodiment the seeking is bilateral and the gravitational pull between two mutual seekers is defined by a new and often much larger force related to the risk associated with the combination of the seekers. In an example a perturbation comprising a fall in bicarbonate is seeking a plurality of perturbation forces, one of which is a rise in absolute band count. A rise in absolute band count is also seeking a plurality of perturbation forces is a fall in bicarbonate. If a rise in absolute band count finds a fall in bicarbonate they are attracted by a very high force because the combination suggests a time dependent dangerous condition which can evolve rapidly.

In one embodiment, vector analysis is performed to provide insight into diagnostic paths for patient conditions, failure modes, and clinical failures. Patient conditions, failure modes, and clinical failures are associated with one or more object types. Each object type has a set of instances (occurrences) per patient. Vector analysis reviews the paths leading to the condition or failure in time to provide insight into the evolution of perturbation and/or recovery. The analysis also provides a method for improving retrospective quality review. Further, vector analysis can be utilized to refine the definition of occurrences within an image or cascade to improve sensitivity, specificity or other correlativity feature.

A complex object type represents a tree structure of other object types of which it is composed. For example, if X is a binary of type A and type B, then X has a tree structure in which X is a tree and A and B are leaves of the tree. In this simple case, if X was associated with a condition, failure mode or clinical failure then vector analysis would consider X to have two diagnostic paths: A→X, B→X. In the domain (XAB) A and B are considered initial types and X is considered a diagnostic type. Were a single instance of X to be identified for a patient, then there would be two diagnostic path traversals (OA1→OX1) and (OB1→OX1) where OA1, OB1, and OX1 are Occurrences of types A, B and X respectively in which OA1, OB1 are components of the binary OX1.

Figure 8:
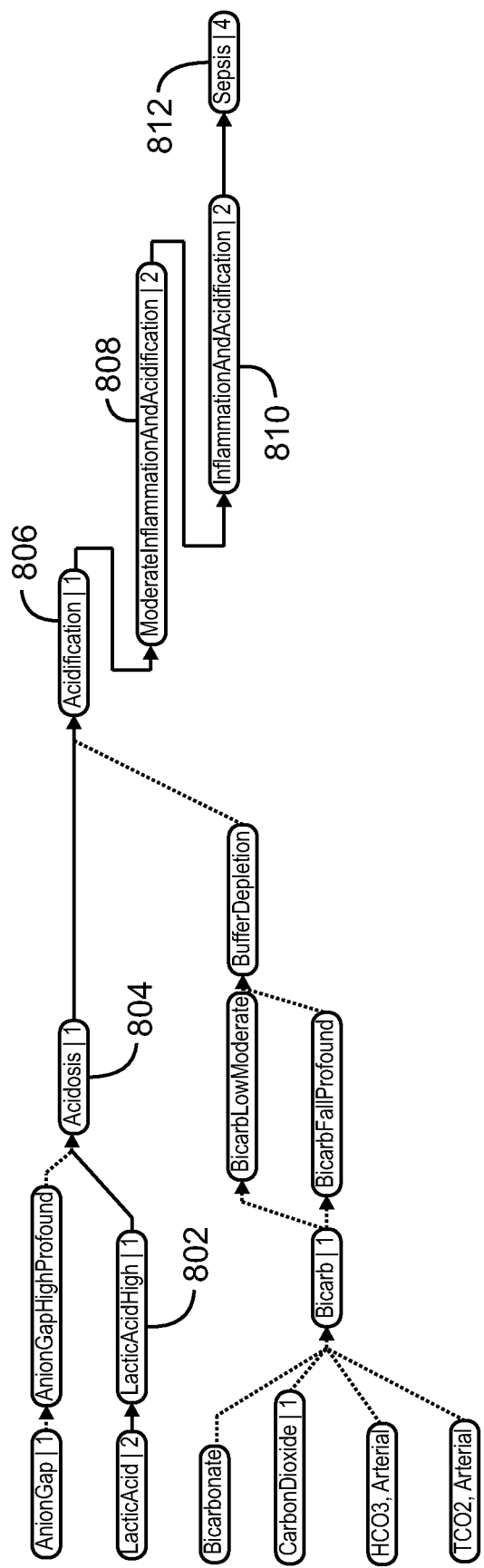
FIG. 8 depicts a single complete diagnostic path traversal for Sepsis in which solid lines between types of perturbations indicate traversal and dotted lines between types indicate no traversal. The instance depicted has an initial occurrence of LacticAcidHigh traveling through Acidosis, Acidification, ModerateInflammationAndAcidification, and InflammationAndAcidification to Sepsis.
Figure 9:
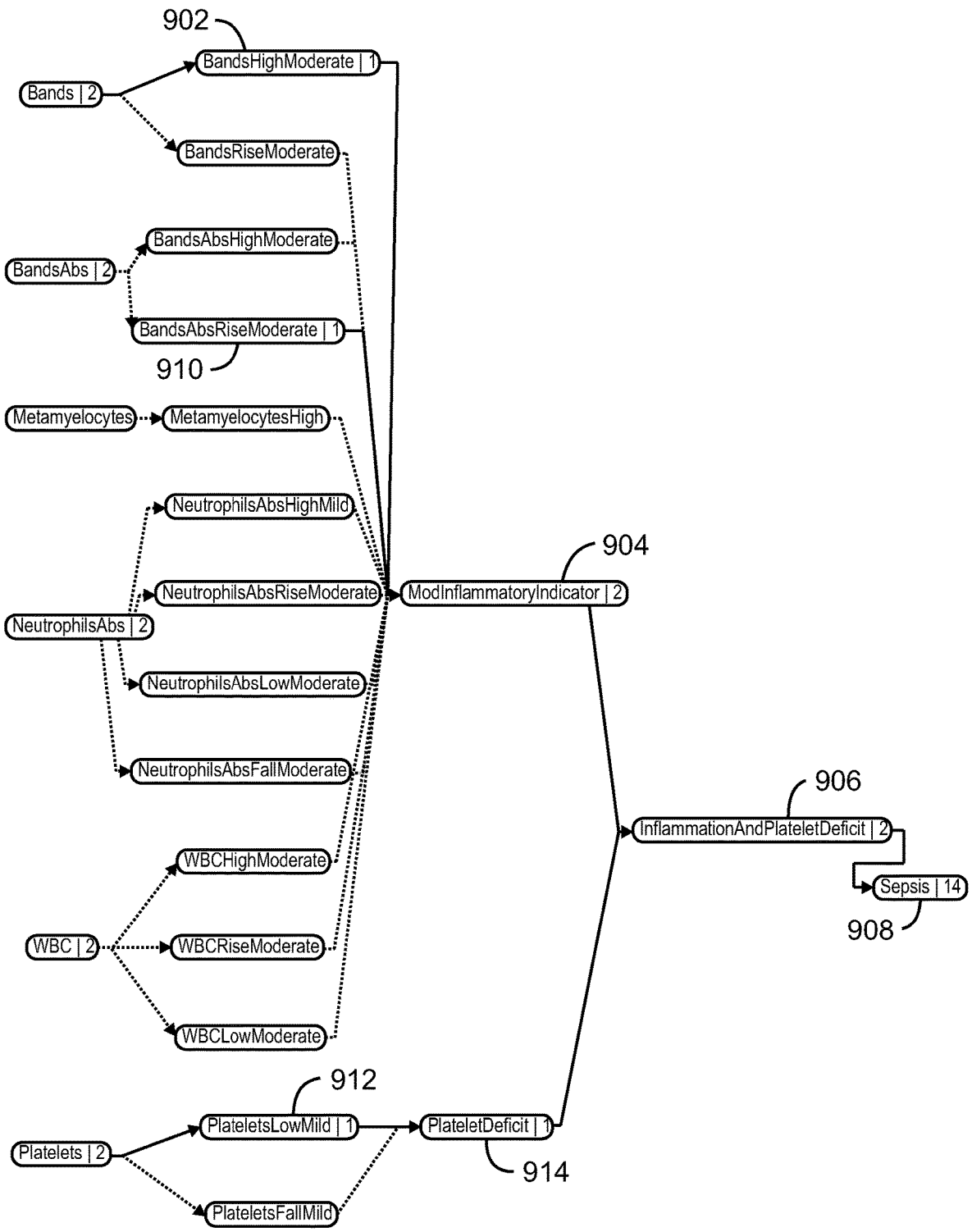
FIG. 9 depicts multiple complete diagnostic path traversals for Sepsis in which solid lines between types of perturbations indicate traversal and dotted lines between types indicate no traversal.

In more complex scenarios, a diagnostic path traversal would have the structure of I→L1→Ln→D where I is the initial occurrence, D is the occurrence indicative of the condition and L1 through Ln are linking occurrences. For example, in FIG. 8 a single diagnostic path traversal is shown. The path with a solid line (as opposed to a dotted line) indicates the actual traversal of one or more occurrences. FIG. 8 shows a single traversal traveling from LacticAcidHigh 802 through Acidosis 804 through Acidification 806 through ModerateInflammationAndAcidification 808 through InflammationAndAcidification 810 to Sepsis 812. As another example, in FIG. 9 we can identify three complete diagnostic path traversals. The first diagnostic path traversal has an initial occurrence type of BandsHighModerate 902 and then proceeds through ModInflammatoryIndicator 904 then InflammationAndPlateletDeficit 906 and then to Sepsis 908. The second diagnostic path traversal has an initial occurrence type of BandsAbsRiseModerate 910 and then proceeds through ModInflammatoryIndicator 904 then InflammationAndPlateletDeficit 906 and then to Sepsis 908. The third diagnostic path traversal has an initial occurrence type of PlateletsLowMild 912 and then proceeds through PlateletDeficit 914 then InflammationAndPlateletDeficit 906 and then to Sepsis 908.

Given a patient matrix, vector analysis will derive 0 or more complete diagnostic path traversals. For example, given the domain (XAB) used above, if a patient has two instances of the X object then (given that both components of a binary are required) there will be 4 complete diagnostic path traversals.

Object types, such as classification which have optional or variant sources provide variability in paths. For example, if a classification Q is defined as R or S or T then in the domain (QRST) there are 3 diagnostic paths: R→Q, S→Q and T→Q. If a patient has two instances of Q then (given that a classification is created from any one of its sources alone) there will be two complete diagnostic path traversals.

Diagnostic path traversals provide the basic building block of vector analysis. In one embodiment, diagnostic path traversals are represented as records with the following fields: condition, patient id, diagnostic instance id, diagnostic instance type, diagnostic instance earliest identification time, initial instance id, initial instance type, initial instance earliest identification time, diagnostic path traversal signature, and primary sub-path.

In one embodiment, the diagnostic path signature is defined as a string containing the path elements listed with a connector (e.g. "→"). For example a path signature from the complete traversal in FIG. 8 is the string: "LacticAcidHigh→Acidosis→Acidification→ModerateInflammationAndAcidification→InflammationAndAcidification→Sepsis".

Since conditions are often defined in terms of a classification (i.e. a statement with a list of alternatives separated by an 'or' operator) it is useful to consider primary sub-paths into a condition. If, for example, Sepsis is defined as "SIRSSevere or InflammatoryAugmentationProfound or SIRSandRespFailureMod" then there are at least 3 primary sub-paths into Sepsis. If any of these three elements specified are themselves simple classifications (e.g. a list of alternatives separated by an 'or' operator) then the members the classification will replace the original classification as primary sub-paths. This process is repeated until all primary sub-paths are identified. Therefore, the primary sub-path is a direct unqualified gateway into the condition. More formally this is specified as a type for which an occurrence will be guaranteed to become an instance which indicates the condition but for which arriving occurrences to the type are not.

Primary sub-paths provide a top-level differentiation of diagnostic paths and are much more cognitively manageable than an entire diagnostic path.

In one embodiment the diagnostic path traversal record contains any reference information necessary to access the occurrence instances represented in the path.

In one embodiment additional key characterizes (e.g. Severity Category) are included in the record and in the path signature to provide additional specification.

In addition to instances of complete diagnostic path traversals, vector analysis identifies and maintains partial path traversals. Further analysis can be done to identify the reasons that the path did not become a complete diagnostic path traversal. Failure reasons are derived by determining all of the next steps that could have been taken. For each candidate next step a failure reason (e.g. no SevereInflammation found within 1 day) is derived and stored.

In one embodiment, failure reasons are stored by the real-time engine during execution. In one embodiment, a minimum distance is specified indicating the number of steps required from the end of the path traversal to the type indicating the condition. In one embodiment additional information is provided to quantify the failure (e.g. indicating by "how much" a qualification was missed).

In one embodiment partial diagnostic path traversals are aggregated along with complete diagnostic path traversals. These records include failure reasons, distance from diagnosis and potential primary-sub paths to name a few.

Figure 10A:
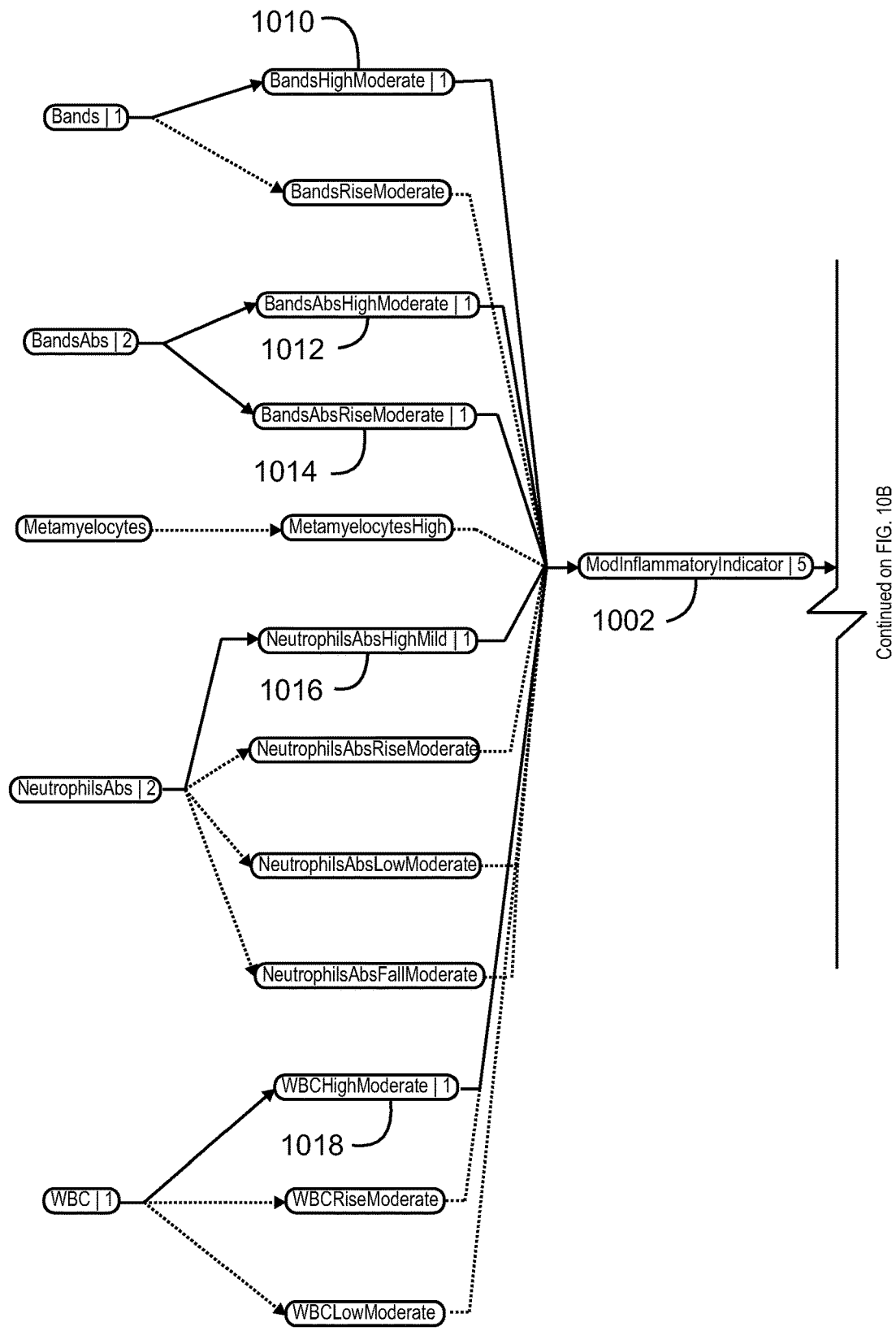
FIGS. 10A and 10B depict multiple complete diagnostic path traversals for Sepsis. In the example illustrated in FIGS. 10A and 10B, the path traversal for Sepsis includes the ModInflammatoryIndicator. The solid lines between types indicate traversal and dotted lines between types indicate no traversal. In the case illustrated in FIGS. 10A and 10B, 3 primary sub-path traversals are shown—SequentialInflammationInjury, InflammationAndPlateletDeficit, and InflammationAndAcidification. Further, 3 other primary sub-paths are shown as not being traversed—InflammationAndIonCalciumFall, InflammationAndAlbuminFall, InflammationAndCalciumFall.
Figure 10B:
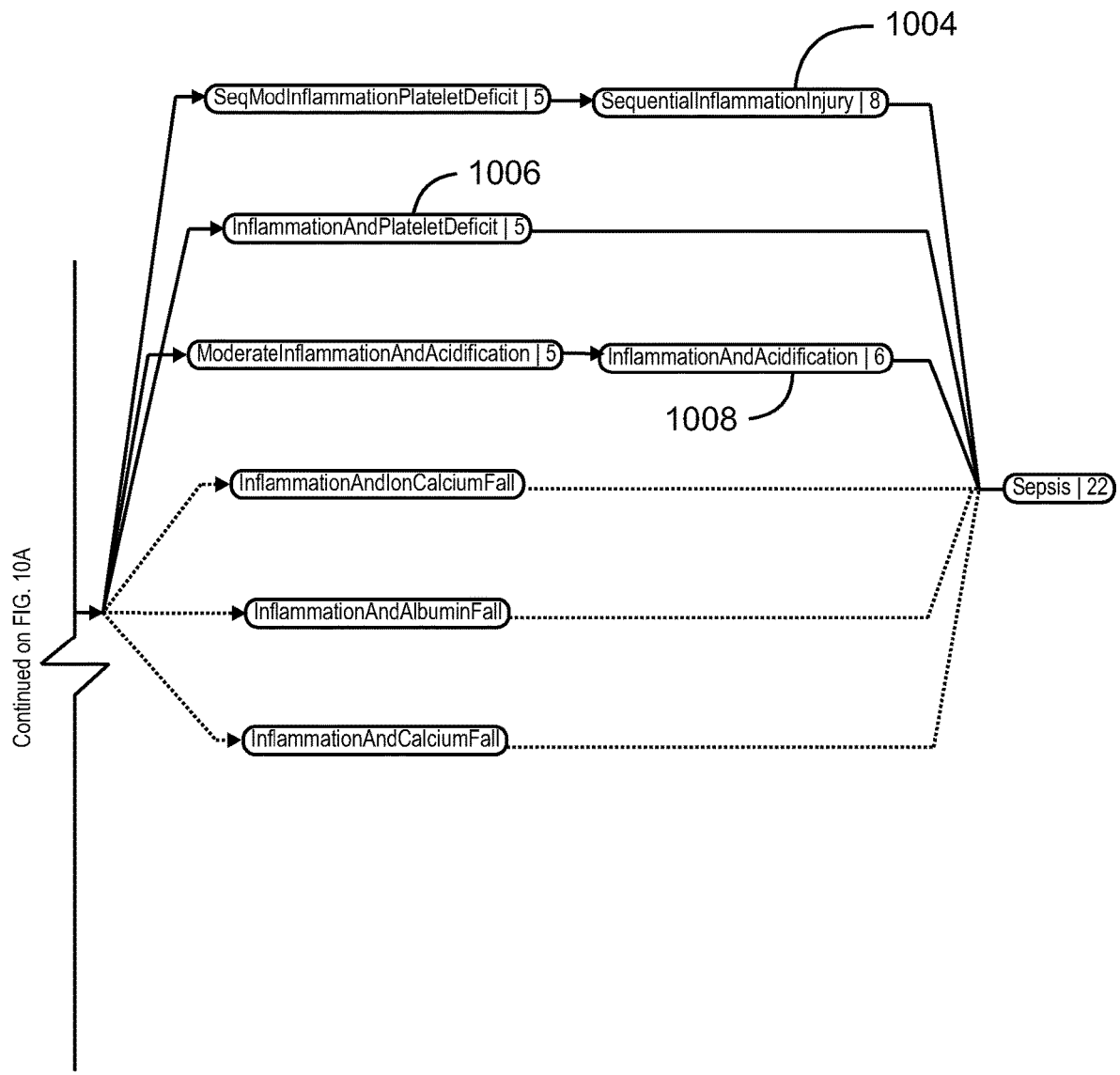

Having a comprehensive set of partial and complete diagnostic path traversal records provides a powerful mechanism for analysis and deriving insight into patient condition, disease evolution and recovery. For example, in FIG. 10 the filtering of path traversals by ModInflammatoryIndicator 1002 shows initial types, paths and primary sub-paths through which Sepsis identification was accomplished for a given patient at a specific point in time. FIG. 10 shows, for example, that 3 primary sub-paths used for the traversals (SeqentialInflammationInjury 1004, InflammationAndPlateletDeficit 1006 and InflammationAndAcidification 1008) are dependent on the identification of ModInflammatoryIndicator 1002. Further, it is clear that 5 different initial types (BandsHighModerate 1010, BandAbsHighModerate 1012, BandsAbsRiseModerate 1014, NeutrophilsAbsHighMild 1016 and WBCHighModerate 1018) are triggering ModInflammatoryIndicator 1002.

In one embodiment researchers work from the bottom up to define failures from a set of time series. Researchers may begin with a set of actual time series from patients diagnosed with known failures, with a set of time series generated by the processor to simulate certain conditions or a set of time series simulating no perturbation at all within a patient. This set of time series may be designated as immutable (for example with the set of actual time series) or may be edited to provide a sample of the patterns being defined. Researchers may select portions of the time series, which the image editor then will analyze to provide candidate event definitions. Alternatively the researcher may select parameters to define an event and the time series displayed will indicate the results of that definition overlaid on top of the time series to provide visual guidance to the researcher. Once the researcher completes the definition of an event the image editor will compare that definition with other definitions within the same channel. If similar patterns are found the researcher is alerted and allowed to create a new event type or select one of the event types already selected. If the event is a relational event, the researcher may select a corresponding event from which relational parameters may be defined and experimented with or the researcher may simply define a function (e.g. >2× Relative Magnitude). Once an event has been fully defined then the researcher may choose to relate the event to another event within the image or to a search window within the image (e.g. to indicate a missing or null event). The researcher may indicate that a processor-ordered event as the beta of a relational binary. Groups of events and relational binaries or any other occurrence may then be selected to define an images. images already defined within the image definition set are highlighted such that they may be included into the image the researcher is working with or the researcher may simply select to alter its definition. Access into the occurrence property Subsystem is available and the expression editors included indicate immediate results with respect to the current image or other occurrences selected. This allows the image editor to work on all aspects of the image including scope definition, qualification rules to name a few.

Alternatively occurrence definitions can be analyzed in the context of sensitivity/specificity analysis or other statistical analysis to refine the definitions either automatically or through the direction of a medical expert. In either case, metrics can be derived by sorting, filtering and aggregating this set. Analysis can be executed against large patient populations, sub-groups or single patients to name a few.

For example, given a patient set, vector analysis can indicate what the top 5 initial paths to Sepsis are for patients over 60 who contracted Sepsis in-hospital.

Basic metrics can be derived around an occurrence within the traversal, a type within the traversal, an initial occurrence, an initial occurrence type, a condition, a diagnostic path, a path signature, a traversal signature, a primary sub-path, a potential primary sub-path, or a failure reason to name a few. Metrics can be derived in counts and percentages both of instances and/or patients.

In one embodiment, a time series of metrics is derived by performing or deriving vector analysis at multiple points in time over the patient stay. In one embodiment, metrics are derived continuously per point received within the system. It is particularly useful for a comprehensive understanding of condition evolution that filters and a time-series approach be used in concert. In one embodiment a patient group is filtered down to limit the set to patients which acquired the condition while being monitored (e.g. in which initial identification of the condition is >28 hours past admit time) and a time series of metric points is created using time in reference to the initial condition identification point. For example, starting with 18 hours before initial identification of Sepsis the primary sub-path percentages are sampled in 2 hour increments. In this way a set of metric time series is created that can be further analyzed. For example, it may be determined that a particular primary sub-path is the ranked as the highest sub-path for the first 12 hours of Sepsis within a specific patient group.

Within these time-series patterns of thresholds, trends, binaries, images and repeating occurrences to name a few can be derived, analyzed and displayed. For example it may be determined that a particular primary sub-path tends to increase from 6 hours since identification to 24 hours since identification and then fall off.

Metric analysis has a wide range of applicability. It can be used for real-time analysis of patient state, analysis of overall disease and recovery evolution in patient populations, and in support of condition script creation/refinement to name a few.

In terms of script refinement/creation vector analysis can provide both false-positive and false-negative analysis.

In one embodiment, false-positive analysis is accomplished by limiting the patient set to patients that have been identified to false positives. Further, within that group, sub-groups can be defined and focused on. For example, a researcher could choose to work on a sub-group of false positives that are identifying patients through a specific primary sub-path (e.g. SIRSandRespFailureMod). Once a patient group has been defined (or a single patient selected) vector analysis provides insight in to the initial occurrence (events that became components of the condition), paths, and primary sub-path.

Top Initial Occurrence Types can be identified and further analysis can be done on them. For example, range analysis can show a distribution of values that fell within the range required indicating whether a small adjustment in the qualification range may eliminate a number of path traversals. In one embodiment, this analysis is automated to combine range-analysis with "what if" scenarios to find range adjustments that eliminate false-positives without creating false negatives.

Top Primary Sub-Paths gives a high-level insight into how false-positives are reaching the condition providing direction into what adjustments will be most effective.

Hot paths can give more detailed insight into how the approach vectors are being reached. Traversals can further be analyzed to find hot links—specific relationships that may be defined to liberally in terms of time or qualification.

In one embodiment, false-negative analysis is accomplished by looking at partial diagnostic path traversal within a condition and reviewing failure reasons within a false-negative group of patients. Near paths can be determined by finding failure paths with the minimum distance values. Ranking can be done by distance or quantification of failure to name a few.

In one embodiment partial and complete traversals are viewed, sorted, filtered, grouped and ranked at the same time. In this way true positives and true negatives can also be engaged to strengthen the script by increasing the mean distance from diagnosis in true negatives or increasing the mean number of identification paths in true positives.

Further, in one embodiment, ignore lists can be maintained to focus on/strengthen aspects of scripts. Ignore lists can be of occurrences within the traversal, types within the traversal, initial occurrences, initial occurrence types, conditions, diagnostic paths, path signatures, traversal signatures, primary sub-paths, potential primary sub-paths and failure reasons to name a few. Ignore lists can be added, updated, deleted and stored.

In one embodiment the brain is identified as a system in the matrix (and distortions may be shown on a weather map or other visualization. Cells may be defined by EEG analysis, for example the detection of severe slowing (a perturbation) and then the cause (the perturbation force) of the severe slowing sought to solve the force binary. Other perturbations such as seizures, or frequent arousals. Outputs of cognitive testing may be converted to R values and/or presented in cells and treated as perturbations in the matrix. In this way persistent perturbation of brain function, for example after sepsis, comprise distortions in the matrix which may be tracked using visualizations such as persistent storm cells on a portion of the map relating to the brain.

As described earlier in one embodiment features of perturbations (slopes, magnitude, duration, and absolute values) are quantized in relation to phenotypic or other reference range of the features. In a similar way, features of relational perturbations (such as pathophysiologic divergence (decoherence)) may be quantized in relation to phenotypic or other reference range of the features. The term "decoherence" may be used interchangeably with pathophysiologic divergence and with refers to the pattern and/or dynamic behavior or relational pattern and/or dynamic behavior of a density which is not expected. For example, the pattern or dynamic behavior of a biologic particle density may be described as decoherent or decoherent in relation to the matrix, when the pattern or dynamic behavior is exhibiting pathologic behavior. The pattern or dynamic behavior of a biologic particle density may be described as decoherent in relation to the phenotypic matrix, when the pattern or dynamic behavior is exhibiting pathologic behavior. The pattern or dynamic behavior of a biologic particle density may be described as decoherent or decoherent in relation to a distortion when the pattern or dynamic behavior is exhibiting behavior which is not the expected pattern or behavior given the pattern or behavior of the distortion.

The quanta of the features of perturbations or recoveries may be mapped on fixed or movable organelles each of which is responsive to changes in the feature which is mapped on the organelle. Organelles may be positioned in a predefined format (such as, in aggregate, defining a hexagon or another shape) within fixed or movable "perturbation cells" or "recovery cells" respectively. "Perturbation force cells" and "recovery force cells" with corresponding organelles responsive to these cells may be on a mapped on the system and/or organ region to which the perturbation corresponds. Regions which comprise relational regions (for example a combined inflammatory-hemostatic region) may be provided, which are comprised of cells which are "relational perturbation cells", the organelles of relational perturbation cells being responsive to relational features of the perturbations. Each organelle may change (a change may comprise for example, a change in color, density, texture, shape, blinking frequency, or another change) in response to changes in the feature which is mapped to that organelle.

This generates a quantized motion image of a distortion and recovery from the distortion and of the forces inducing the distortion and the recovery. By placing all of the cells and organelles in fixed relationships on a preformatted map with a known format, a large mass of complex relational quantized data is presented in relation to a phenotypic, normal, or baseline state so that distortions due to a one type of pathology exhibit predictable ranges of images on the preformatted map which are useful for facilitating the detection, identification, quantification, characterization, and tracking of that pathology type.

In addition the quantized motion image or fixed snapshots or short segments can be imaged and are analyzable by image based pattern and/or pixel recognition systems or other analysis systems.

As discussed, in one embodiment, perturbations, features or quanta derived from the perturbations and/or features may be converted into image components which may comprise; cells, organelles, shapes, bar codes, shape codes, shades, colors, shapes, numbers, and/or pixels, or other image component renderings derived from the perturbations, features, or quanta.

The image components may be aggregated in relation to the perturbations from which the features are derived and/or in relation to the physiologic system to which the perturbation or features relate and/or in relation their relation to treatment, to which the perturbation or features relate.

Image components may be aggregated in relation to whether they are perturbations, perturbation forces, recoveries, or recovery forces. They may also be derived as relational image components and/or aggregated as relational image components. They may be mapped onto relational systems, or maps for relational perturbations, perturbation forces, recoveries, or recovery forces, binaries quaternaries or other relational patterns.

Any of these image components may be placed into fixed and predetermined positions on the display to render images which would be substantially identical same if the perturbations and features are substantially identical thereby producing reliable image changes. These can then be sequenced over time segments and displayed as fixed or changing images or the predetermined format. Training sets of images can then be displayed to one or more image recognition system, as are known in the art, to train the image recognition system to recognize the clinical condition by imaging the displays.

Large archives of displays can be derived using reliable, definitive, gold standards to train the image recognition systems.

The converting the biologic particle densities and other physiologic data into fundamental features, generating image components responsive to the fundamental features and then generating predefined images mapping provides a data processing and mapping and displaying system which takes advantage of advances made in the field of image recognition by the conversion of these complex data sets into images of sufficient granularity and dynamic relational granularity to allow subtle image differences to be recognized in the training set and then applied in the recognition of the image under test.

The maps which display the image components derived from the perturbations, forces, perturbation features, and/or force features can be standardized, as with the development of an ASTM standard or ISO standard for use of the human or animal biologic particle maps worldwide.

A field of image recognition professionals, similar to the field of radiology may be developed, wherein the professionals are trained in the images and the pathophysiology of the diseases under test and are provided other images, such as the time series matrices of the data to over read the diagnostic output of the image recognition software and thereby protect outlier patients.

In one embodiment the image is divided into components or sections and each section, grouping of sections, and/or the entire image may be used to train an image recognition system. The sections section, grouping of sections, and the entire image may be presented to the recognition system in sequence or otherwise marked for their timing relationships.

The image recognition system can then generated probabilities for the diagnoses which at least partially matched by the image or image segment. The image recognition system or processor 200 may also generate a probability matrix or other probability construct and/or a group of time series or a matrix of time series of the probabilities generated.

In one embodiment the time series matrix of probabilities is objectified and processed in the same way as the time series matrix of biologic particle densities to generate perturbations of probabilities, features of perturbations, and image components of the probabilities, which can themselves be mapped to generate an training archive of probability images which are used to train an image recognition systems. This process may be recursive.

One embodiment comprises a medical device for monitoring dynamic patterns of biologic particle densities comprising a processor 200 programmed to detect and analyze perturbations of biologic particle densities, detect and analyze features of biologic particle densities perturbations and to convert the perturbation features into discreet perturbation feature quanta in relation to a phenotypic, baseline or expected range of the perturbation features.

One embodiment is programmed to generate a first set of images responsive to the perturbations, generate second set of images responsive to the perturbation feature quanta, aggregate the first set and the second set into a time-lapsable motion image to generate a motion image of visualization of combined of perturbations and perturbation feature quanta.

The device may be further programmed to detect and analyze forces which induced or caused said perturbations of biologic particle densities, detect and analyze features of biologic particle densities forces, convert the force features into discreet quanta in relation to a phenotypic, baseline or expected range of the force features and to generate a third set of images responsive to the forces and generate fourth set of images responsive to the force feature quanta.

In one embodiment the processor 200 is programmed to aggregate the third set and the fourth set into a time-lapsable motion image to generate a motion image of visualization of combined of the forces and the force feature quanta. The processor 200 may be future programmed to aggregate the first set and the second set with the third set and the fourth set into a time-lapsable motion image to generate a motion image of visualization of combined perturbations and perturbation feature quanta and forces and the force feature quanta. Quanta may be defined by colors, gradation of colors, integers and ascending and descending sequences of integers or other discrete gradation methods.

Figure 11:
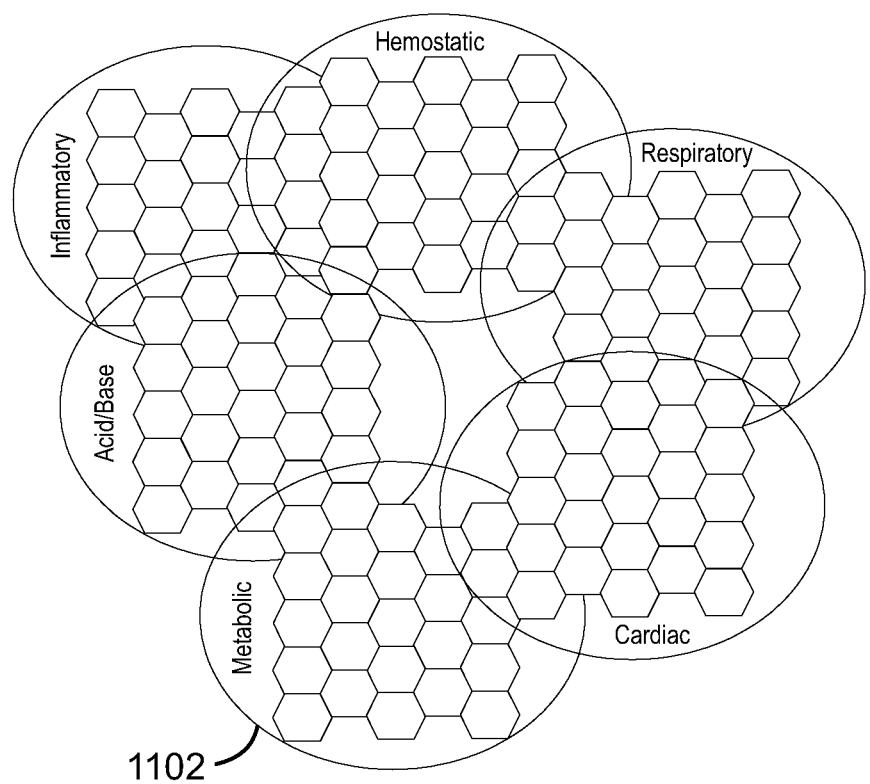
FIG. 11 depicts perturbations, perturbation forces, recovery and recovery forces and/or their features are rendered as hexagons placed within related clinical space systems.

In one embodiment perturbation, perturbation forces, recovery and recovery forces and/or their features are rendered as hexagons 1102 placed within related clinical space systems as shown in FIG. 11. In one embodiment, the hexagons have a fixed location. In one embodiment, the location is based on the severity of the quanta to which the hexagons are responsive. In one embodiment, the relative locations are responsive to severity and/or relationships within and among the associated perturbations and associated features. Alternatively other visual aspects of the hexagons are responsive to the related quanta such as the size, orientation, fill color or texture, border color or texture, transparency to name a few.

Figure 12:
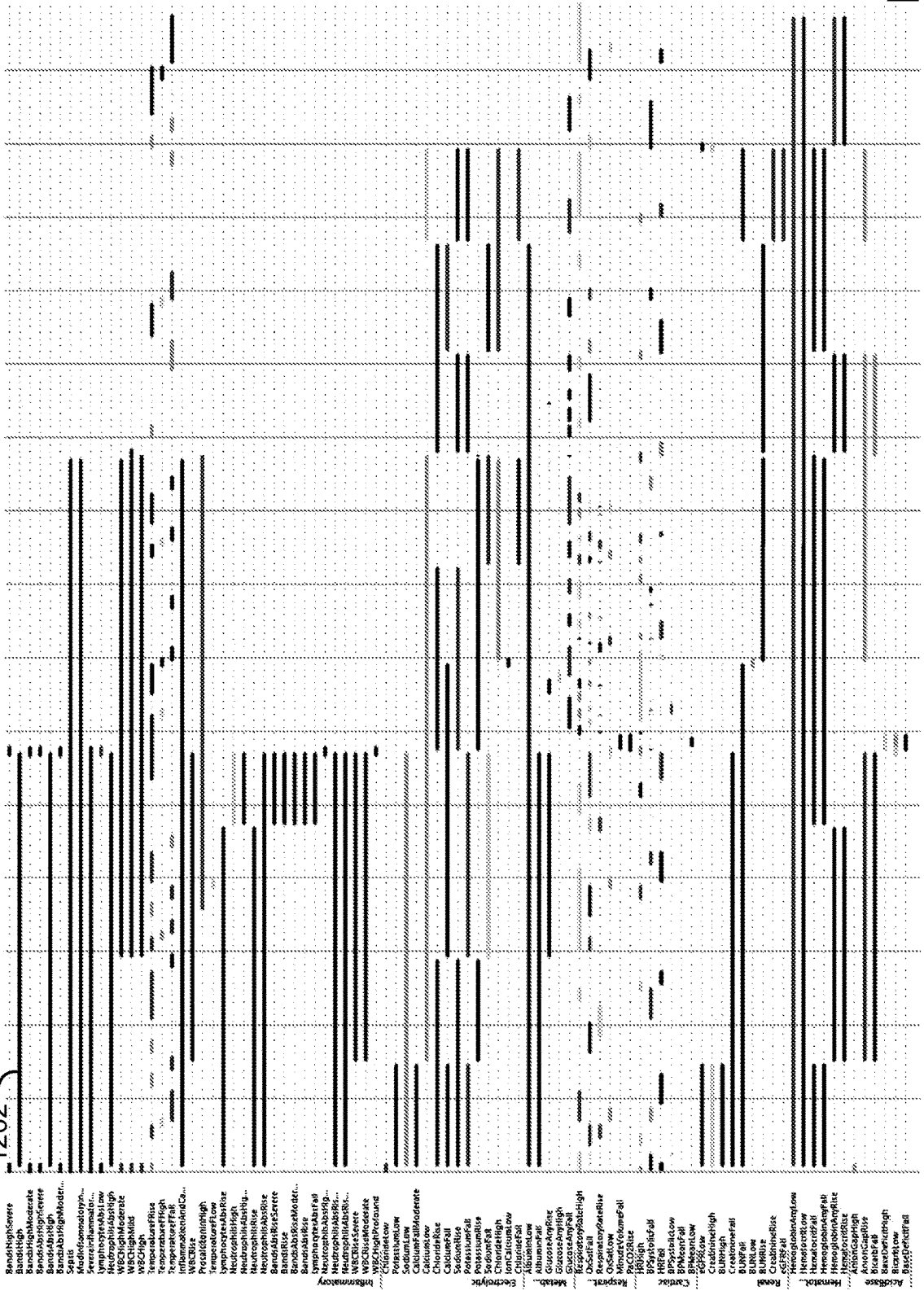
FIG. 12 depicts an image of a severe sepsis patient in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.
Figure 13:
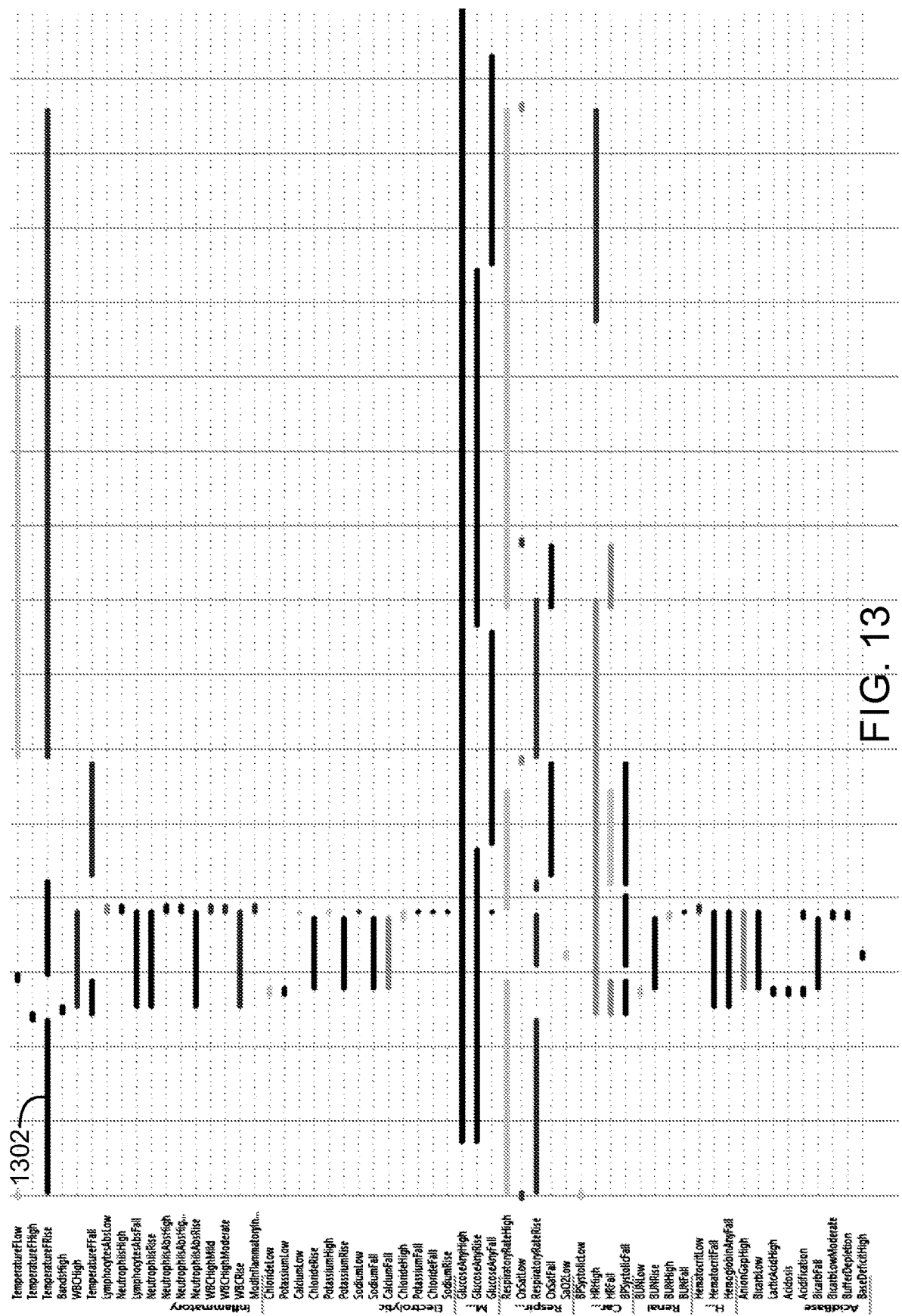
FIG. 13 depicts an image of a sepsis patient which recovered from sepsis in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.
Figure 14:
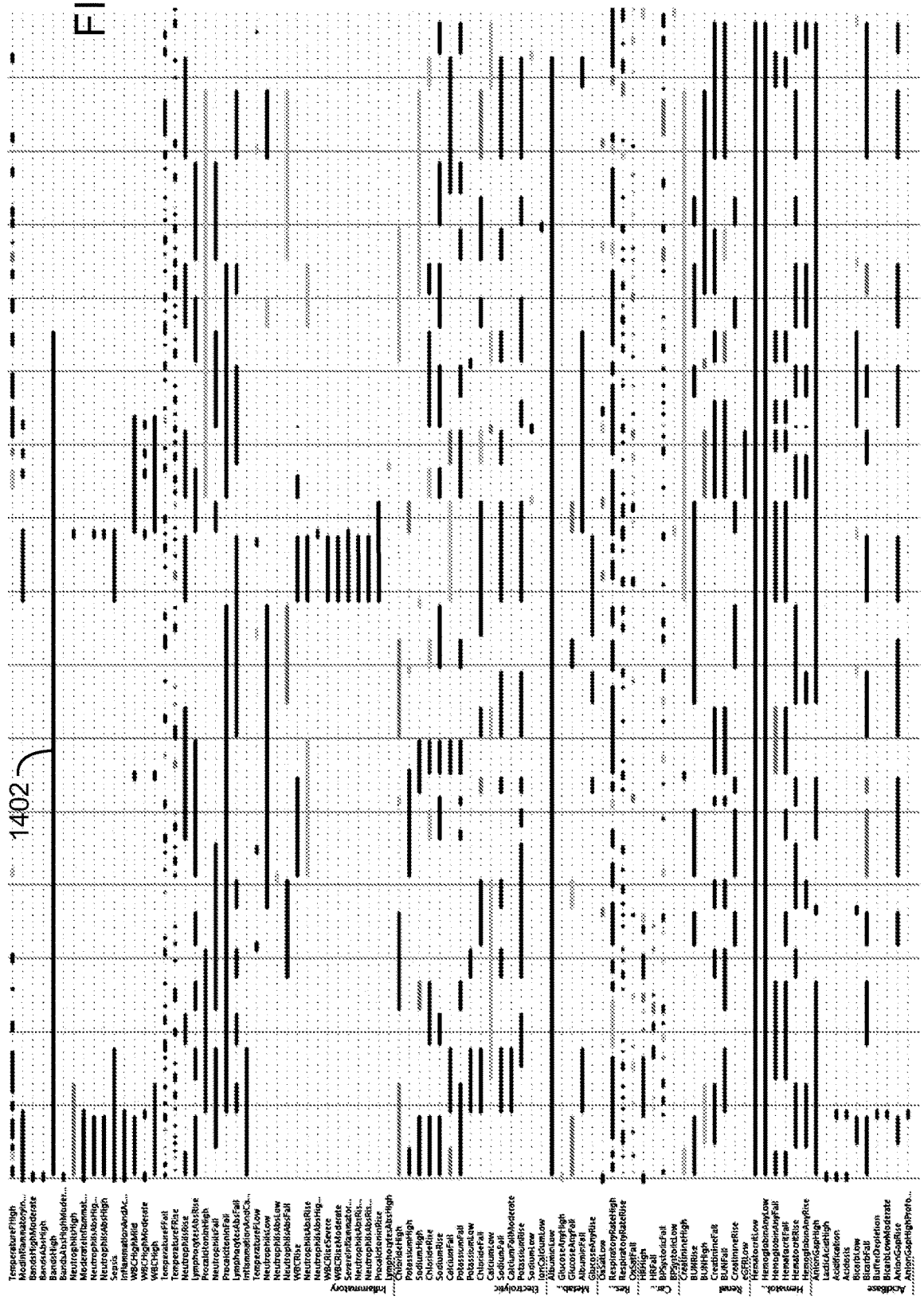
FIG. 14 depicts an image of a long-term severe sepsis patient in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.

In one embodiment, as shown in FIGS. 12 through 14, perturbations, perturbation forces, recoveries and recovery forces and/or their features are rendered as bars 1202 across a two dimensional area in which the location and length of the bar is based on the start and end time of the associated perturbation or recovery. The vertical location is set by the type of the perturbation or recovery and may be further grouped by clinical space as shown in FIGS. 12 through 14. Other visual aspects of the bars are responsive to the related quanta such as the size, fill color or texture, border color or texture, transparency to name a few.

FIG. 13 depicts an image of a sepsis patient which recovered from sepsis in which perturbations, perturbation forces, recoveries and recovery forces and/or their features rendered as bars 1302 across a two dimensional area in which the location and length of the bar are based on the start and end time of the associated perturbation or recovery and the vertical location is set by the type of the perturbation or recovery grouped by clinical space.

FIG. 14 depicts an image of a long-term severe sepsis patient in which perturbations, perturbation forces, recoveries and recovery forces and/or their features rendered as bars 1402 across a two dimensional area in which the location and length of the bar are based on the start and end time of the associated perturbation or recovery and the vertical location is set by the type of the perturbation or recovery grouped by clinical space.

The bars 1202, 1302, 1402 may be provided in a fixed location and be filled in or otherwise enhanced, modified or visible, only if the data needed to generate the bar was available to the processor 200. Although, predominately perturbations are displayed in the exemplary maps of FIGS. 12 through 14. Each feature or a wide range of relevant features may be mapped onto the map. In this example, a map may contain hundreds or thousands of potential bars 1202, 1302, 1402 which can be very thin lines and/or very thin linear patterns for the purpose of providing them on a single view.

Figure 24A:
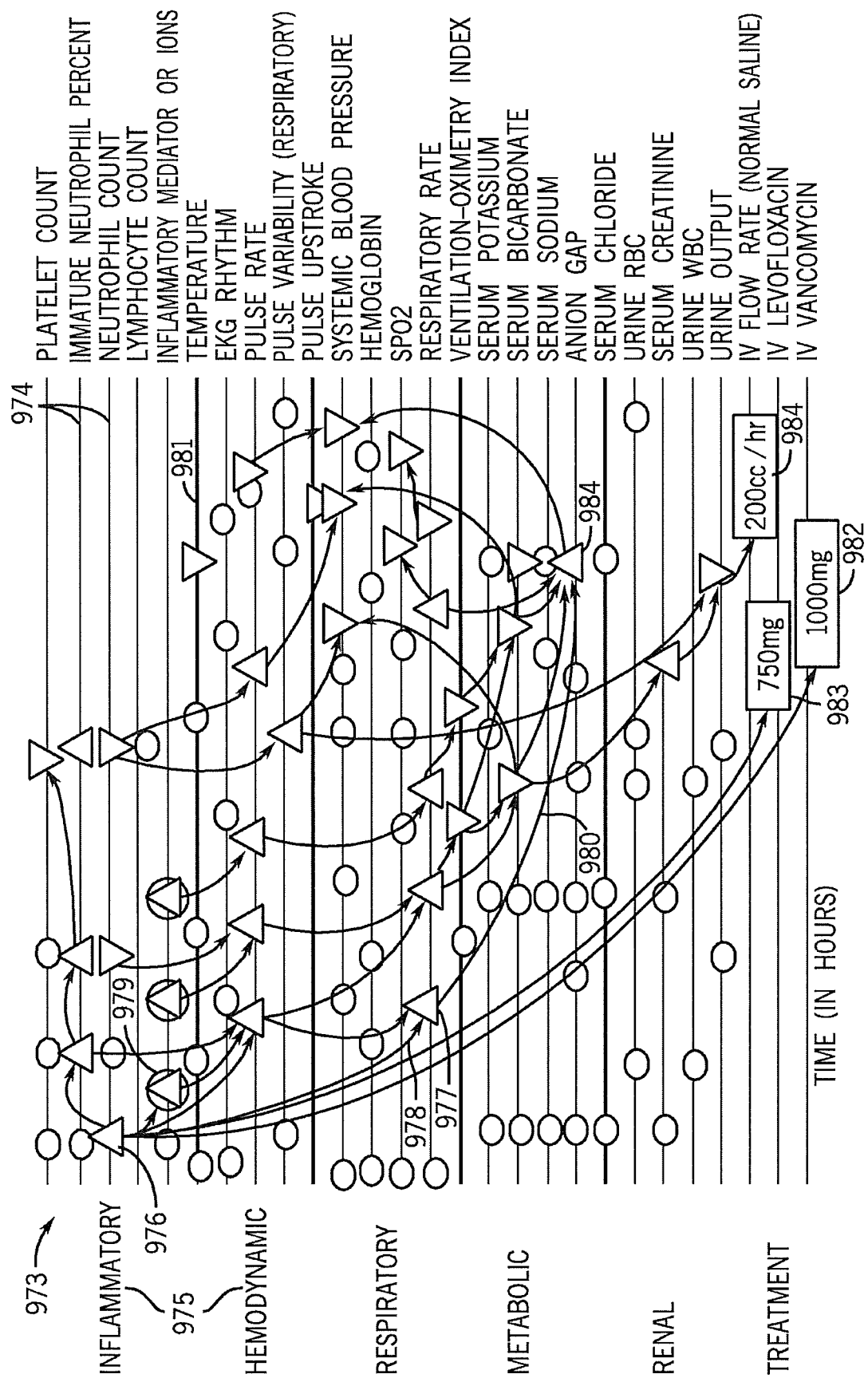
FIG. 24A is an image frame with a plurality of timelines organized into groupings, which shows an image of an expanding cascade of septic shock.

FIG. 24A shows an image frame 973 of a patient's physiologic system and care and demonstrates one exemplary image according to one embodiment as generated by the image processor. The image shown is indicative of dynamic progression from an image suggestive of stability to an image suggestive of a cascade of septic shock. The image displays objectified events, which met criteria as up and down arrows indicating whether they are, rise events or fall events respectively. Minor time series variations (such as detected minor rises or falls typical of signal noise, which fail to meet criteria by the objectification processor as events) are represented on each time-line as open circles along parallel time lines. (The visualization of such variations may be turned on or off as desired.) The detected events are combined with other events to form binaries which are then combined to produce an image of relational patterns including aggregate binaries and individual events defining the dynamic state of the patient's physiological system and of the medical care applied to the physiologic system during the time interval of each respective image Within the complete image, smaller images aggregate to produce the larger image of failure (in this case, of septic shock).

Since FIG. 24A is a late "time lapsed" frame of a MPPC, which has exhibited many earlier frames, wherein the processor 394 suggested that confidence of septic shock was high. The figure is readily understood by the representations of rise events or fall events as up-arrowheads and down-arrowheads respectively on each time line 974, each of which is labeled on the left. The timelines 974 are grouped into categories 975 designated on the right. The first event detected within the time interval of the image is a perturbation event—a rise event of the Neutrophil count 976 shown by the upward pointing arrowhead on the Neutrophil timeline. This perturbation event is combined by the relational processor to a second perturbation event—a rise in respiratory rate 977 also shown by an upward arrowhead, to generate the first relational binary 978 (combined in the figure by the arrow connecting 976 and 977). (While the respiratory (tidal or ventilation rate) may be used the respiratory amplitude (tidal or ventilation amplitude) may alternatively be used or a mathematical combination of both may be used to generate a time series and/or a derivative of the tidal curve (in one example the slope and amplitude, the area under the peak to peak and/or the area above the nadir to nadir) may be used. time series of all of these may be incorporated into the matrix for at risk patients or the time series may include only one or two but expanded to include derivatives retrospectively and prospectively upon the detection of a pattern or image or upon the identification of risk factors. In one embodiment the respiratory time series are monitored using a nasal cannula whereas in another they are monitored using a sound sensor placed on an airway or chest. Both the rate of the tidal sounds and the amplitude of the tidal sound and the length of the tidal sounds in each cycle can be used to provide an indication of tidal amplitude. Early termination of tidal sounds (especially inspiration) before the next breath suggests that the tidal amplitude is not high. The duration of the tidal sounds and the tidal sound amplitude can be used in a manner analogous to the duration and amplitude of the nasal thermister temperature in a single direction.) Each subsequent perturbation in the image is designated by its timeline and arrowhead. An arrowhead with a circle around it designates perturbations determined by testing automatically ordered by the processor 394 in response to the detection of a particular image. In an example the rise event in inflammatory mediators or indicators 979 was ordered by the processor 394 to better define the inflammation portion of the image which was somewhat obscured because the early images demonstrated a rise in neutrophil count, a rise in pulse, and a rise in respiration rate but with a normal temperature. Since this ambiguous image must be better defined to decide care, testing for inflammatory mediators/indicators is automatically ordered by the processor to better complete the image.

Using these basic designations the image of FIG. 24A becomes self-explanatory and FIG. 24A reveals a clear image frame (a time lapsed snap shot) late an MPPC including perturbations of inflammation, followed by a hemodynamic perturbations, followed closely by respiratory perturbations, and then renal perturbations in an expanding and linked cascade 980. Note that the initial rise in Neutrophil count 976, the first detected perturbation event, will have completely disappeared later in the cascade such that frames late in a failure process are best viewed with the sufficient scale to observe the onset of the cascade 980. Note the image shows a complete lack of any events along the temperature timeline 981. Without the Patient safety processor, the lack of a fever could easily fool a healthcare worker who may think of fever as a reliable indicator for the early detection of sepsis. Note however that the processor 394 is programmed to recognize that it has rendered an incomplete image and the processor 394 seeks to complete the image by ordering testing for inflammatory mediator 979. This testing serves as a "surrogate images" for a rise in temperature thereby establishing that the entire image does in fact exhibit an early component of inflammation.

Two drug treatments are evident in the image, the antibiotics Vancomycin 982, designated by its dose on the time line, and Levofloxacin 983, similarly designated. Also a rise in IV fluids in the form of normal saline 984 is indicated. All of these treatments come late after the image has long been indicative of a high probability of sepsis. (This delay, which may be detected in real-time by the patient safety processor, suggests poor and ineffective care, which has ignored or otherwise been poorly responsive to the patient safety processor. The processor may be programmed to provide an indication of the quality of the care provided. time lines, which include the care worker or ward may be provided so that delays may be linked to particular locations or care workers.)

Figure 28:
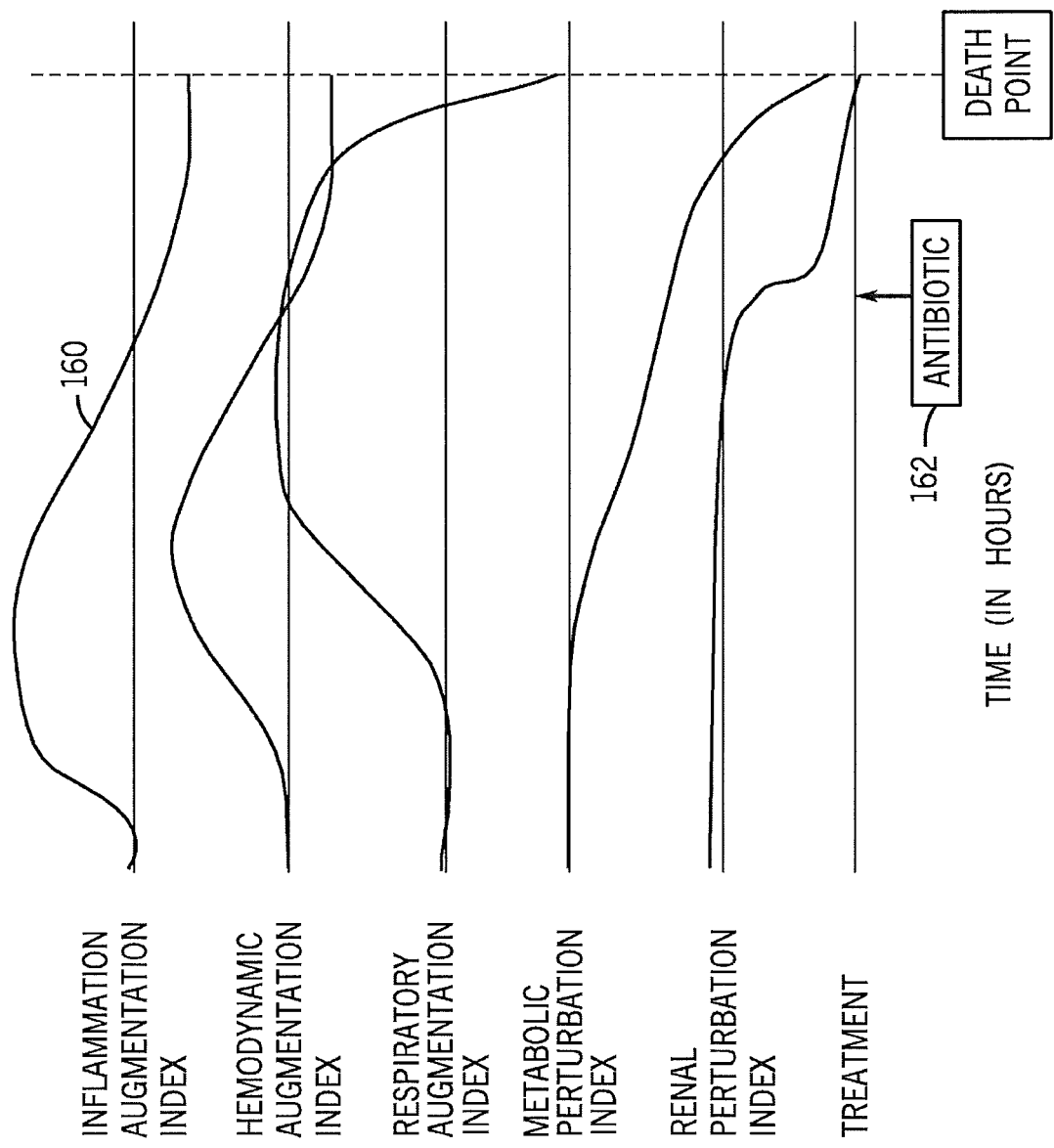
FIG. 28 shows overview image of perturbation onset and progression as derived from the time lapsed MPPC of FIG. 5A wherein the perturbations in each grouping are incorporated into an aggregate index along a single smoothed time series for each group.

The image of the progressive cascade 980 shows the drug treatments components 982, 983 of the image are too late because they appear within the image very late along the cascade 980. The late portions of the image of the cascade 980 also include a very ominous beta including a rise in anion gap 985. The addition of this new image provides a mature image of cascade 980, which is now strongly indicative of a stage of septic shock. Other image views may be for example; specific expanded portions of the time lines, specific expanded views of images (or other occurrences) along the timeline portions, specific groupings of the timelines, overviews of perturbation progression from group to group (an example of this is shown in FIG. 28), to name a few.

Figure 24B:
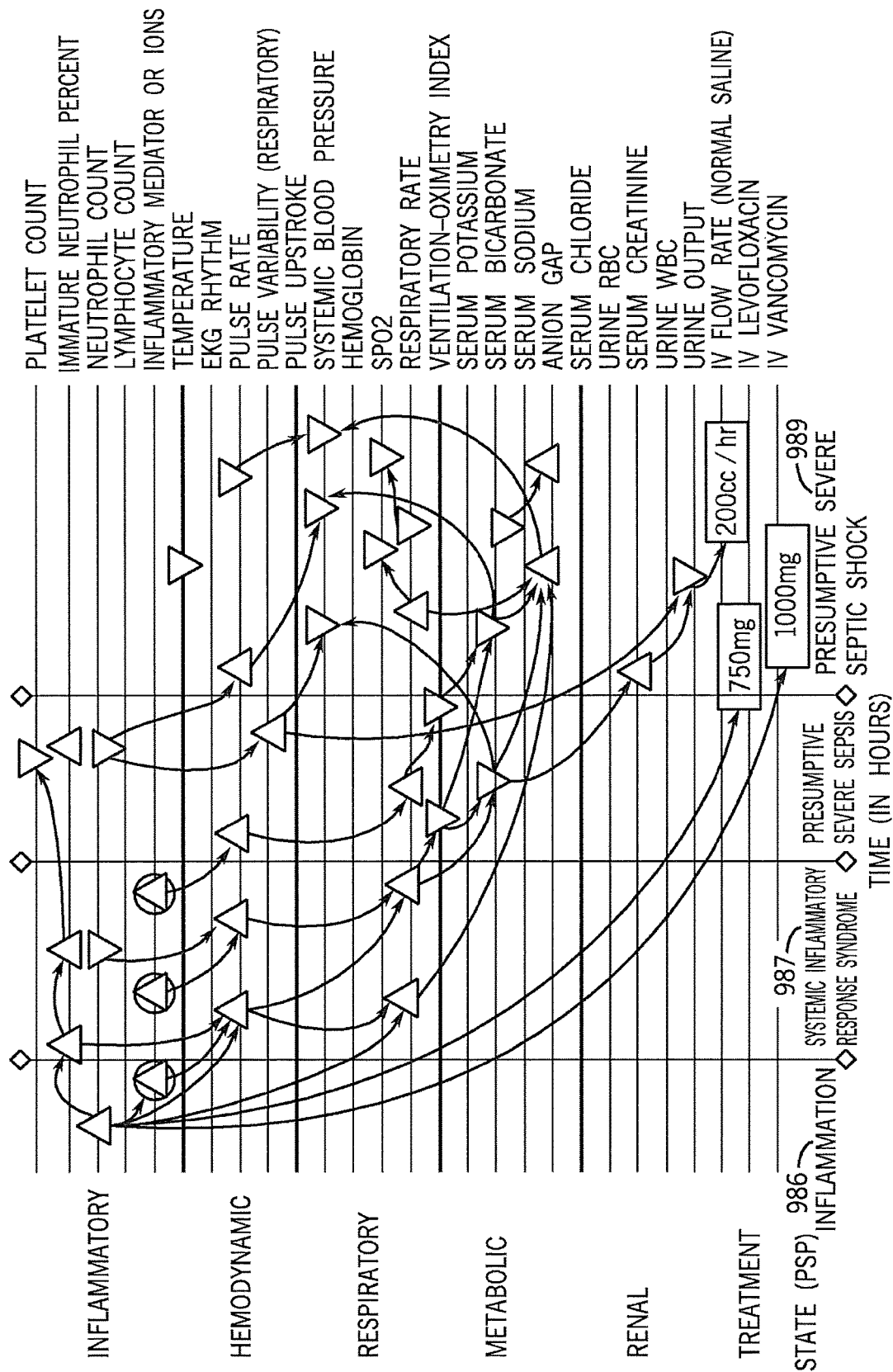
FIG. 24B is an image frame with a plurality of timelines organized into groupings, which shows an image of an expanding cascade of septic shock with portions of the image being separated into sequential states.

FIG. 24B is the image frame of FIG. 24A with portions of the image being separated into sequential states of inflammation 986, systemic inflammatory response syndrome 987, presumptive severe sepsis 988, and presumptive severe septic shock 989.

Figure 15:
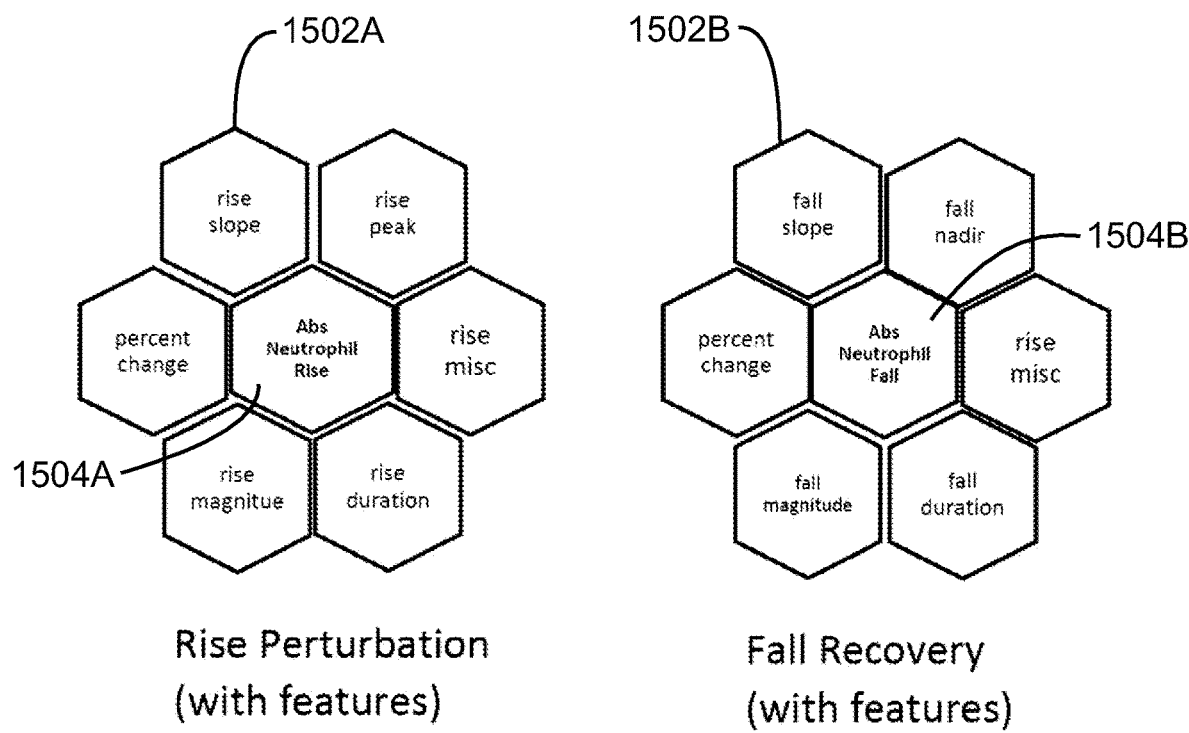
FIG. 15 depicts an AbsNeutrophil rise perturbation and an AbsNeutrophil fall recovery rendered as hexagon clusters that include both the fall and recovery along with their associated features.
Figure 24C:
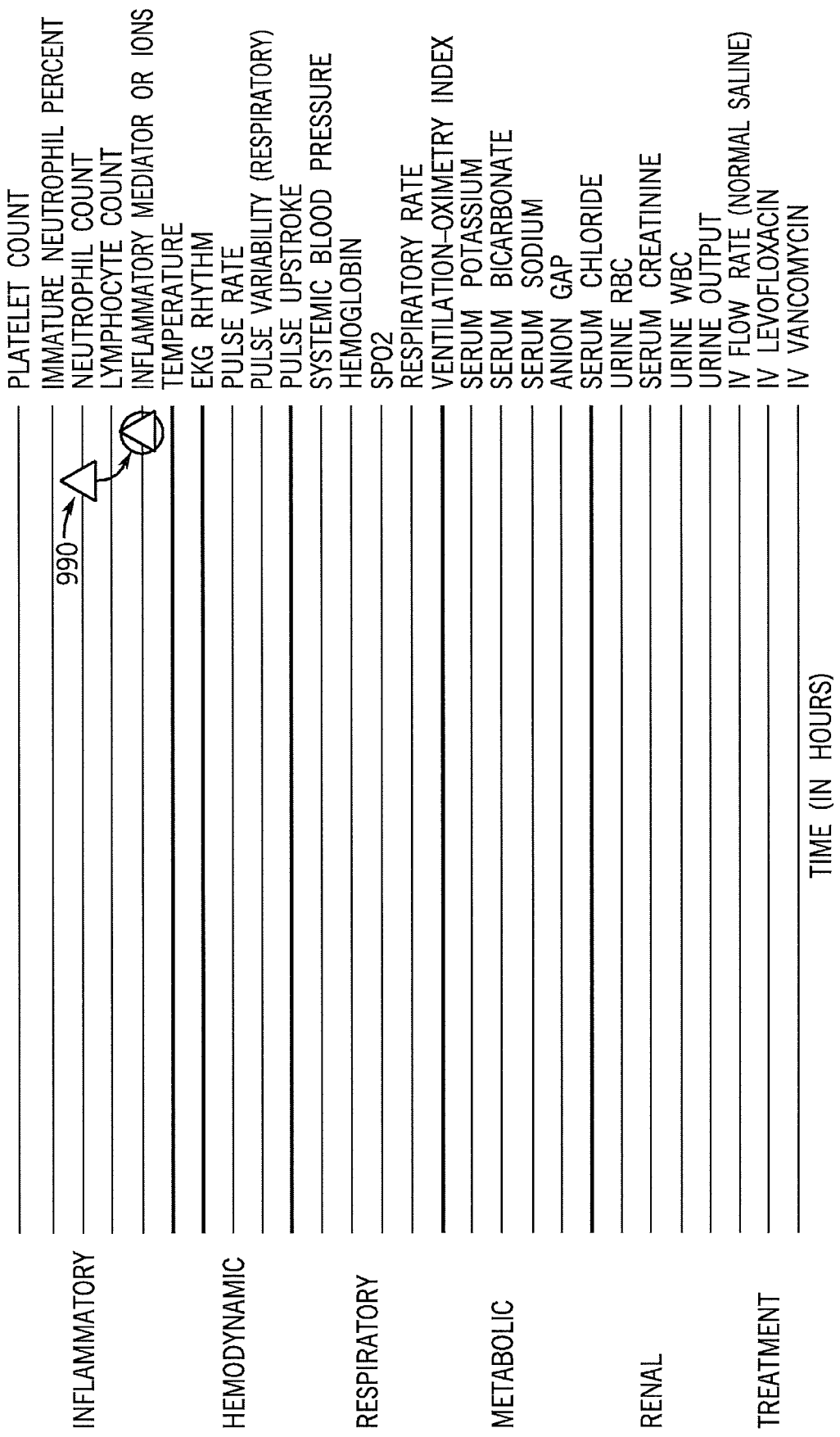
FIG. 24C is an image frame with a plurality of timelines organized into groupings, showing an image of an expanding cascade of severe septic shock an early image of septic shock as presented in real time to demonstrate that there is little in these first perturbations to warn of the impending deadly cascade.

FIG. 24C is an early image frame from real time imaging of the process in FIG. 15. The first "spark", a rise in Neutrophil count 990 evident in this image, is entirely non-specific despite the fact that it, in retrospect, heralds the onset of septic shock, completely disappears by the time this motion picture has reached the point illustrated in FIG. 24D focused testing, more frequent CBC testing, and/or more frequent vital sign measurement to determine the significance of this rise in Neutrophil count may be suggested or ordered by the processor to expand the image to more quickly move toward a more specific image.

Figure 24D:
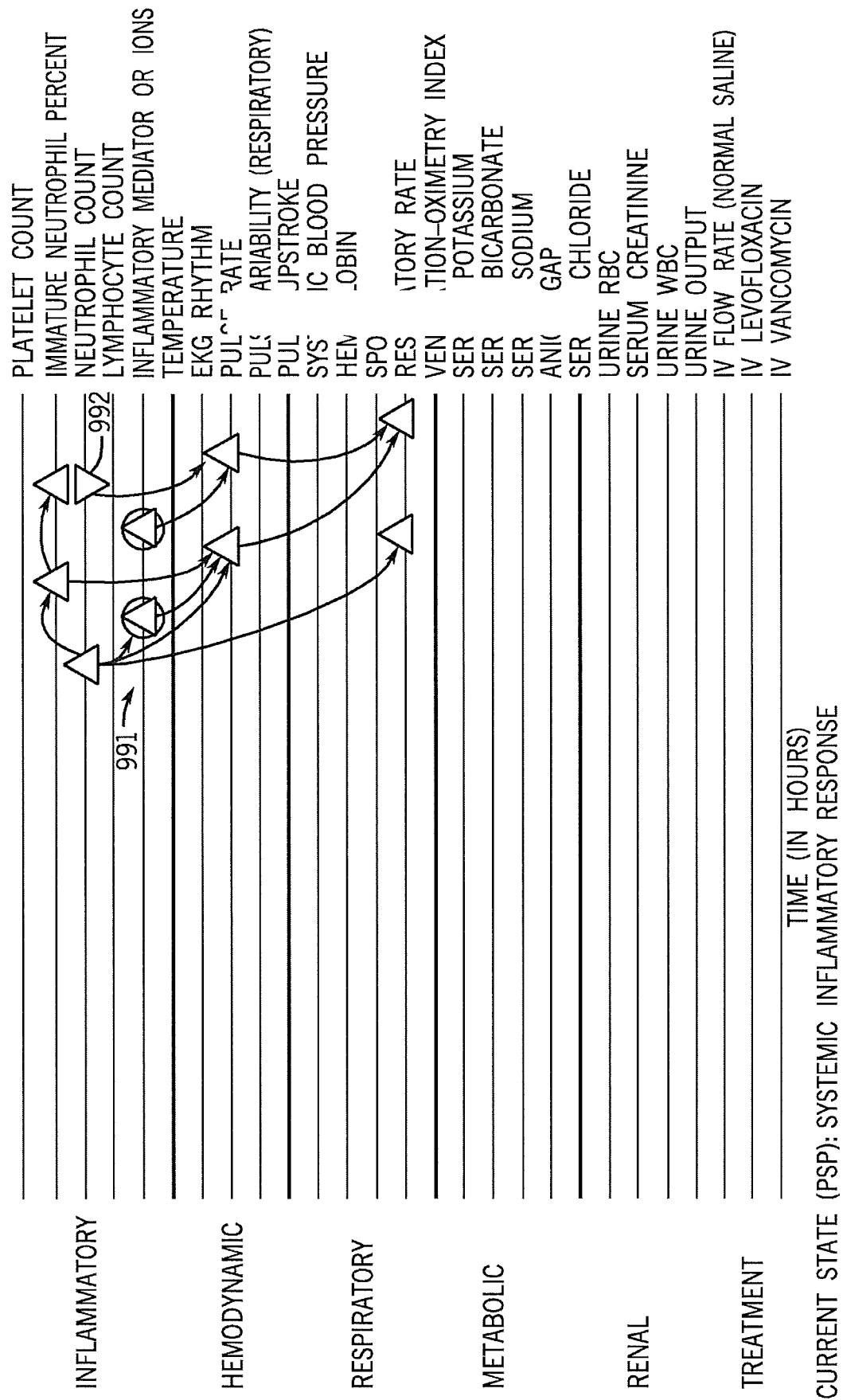
FIG. 24D is an image frame that shows an image of a failure cascade severe septic shock as presented in real time to demonstrate the early image of inflammatory, hemodynamic, and respiratory augmentation, with early immune failure.

FIG. 24D is an image frame from real time imaging of the process in FIG. 15. This frame demonstrates early images of inflammatory, hemodynamic, and respiratory augmentation 991 combined with early immune failure 992.

Figure 24E:
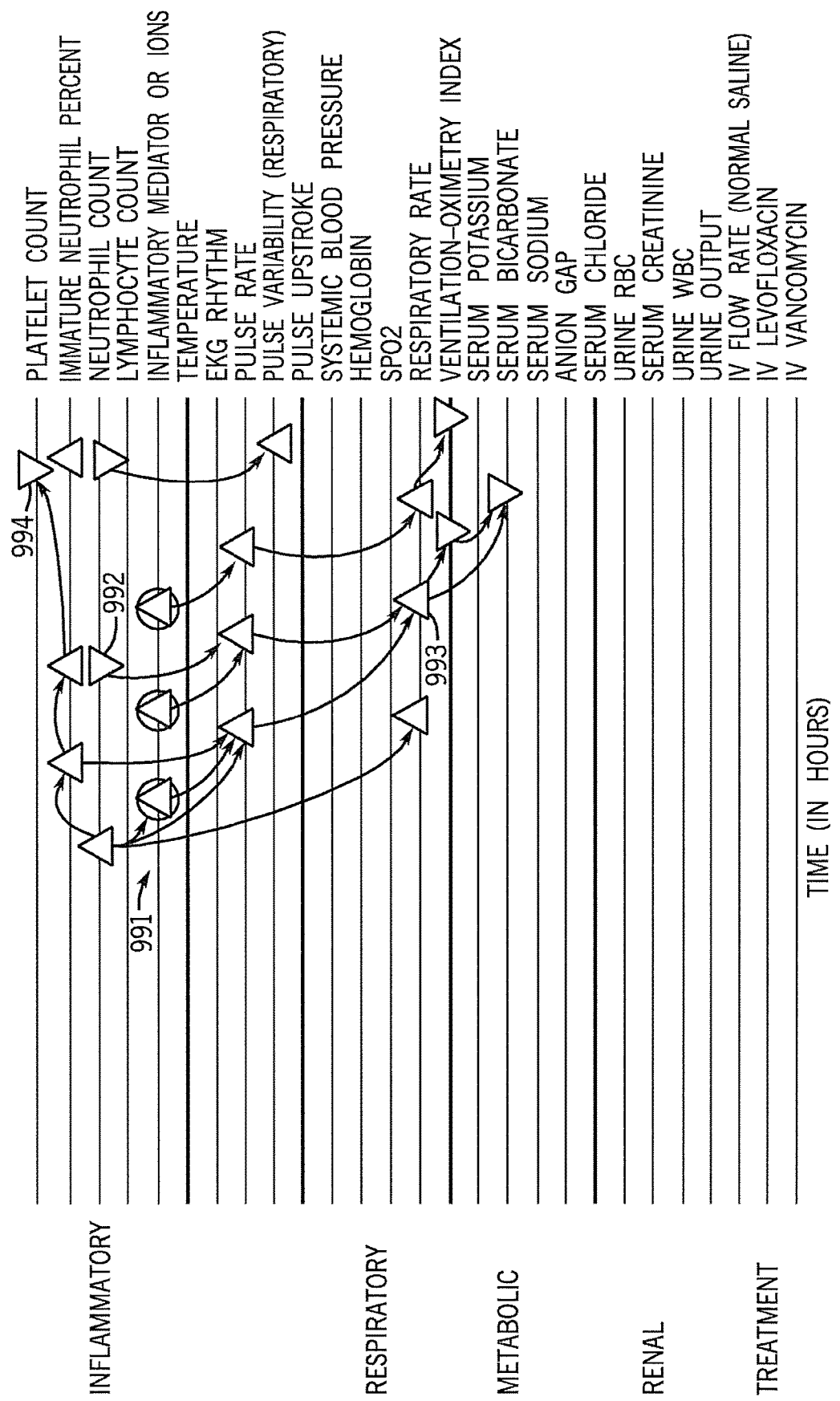
FIG. 24E is an image frame that shows an image of a failure cascade of severe septic shock as presented in real time to demonstrate the image of inflammatory, hemodynamic, and respiratory augmentation, with immune failure, but now with evidence of decline in respiratory gas exchange and fall in platelet count.

FIG. 24E is an image frame from real time imaging of the process in FIG. 24A This frame demonstrates demonstrate the images of inflammatory, hemodynamic, and respiratory augmentation 991, with immune failure 992, but now with images indicative of a decline in respiratory gas exchange 993 and fall in platelet count 994.

Figure 24F:
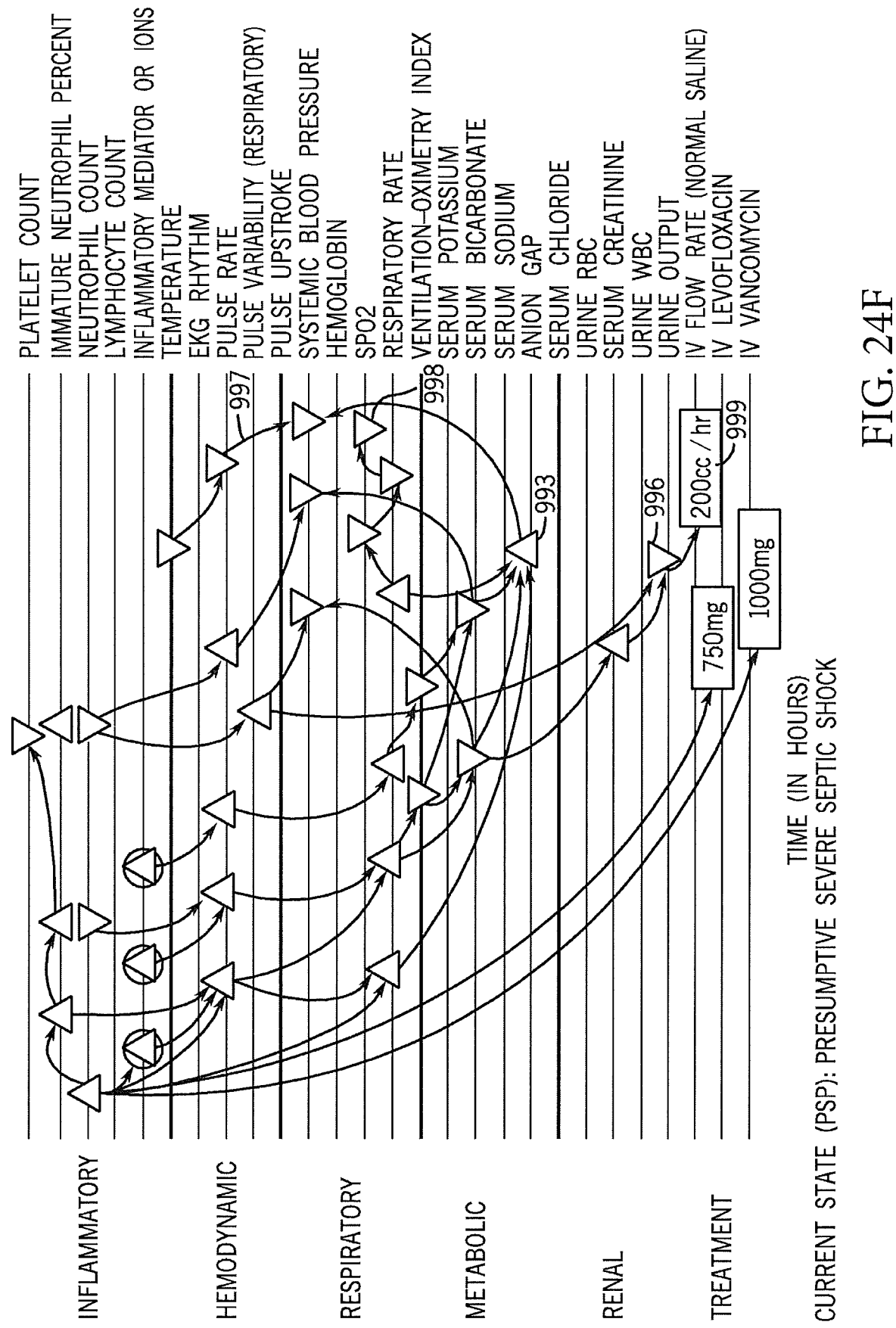
FIG. 24F is an image frame that shows an image of an advanced cascade of severe septic shock as presented in real time to demonstrate progression to metabolic failure, renal failure, hemodynamic failure, and respiratory failure.

FIG. 24F is an image frame of FIG. 24A to demonstrate that the image of now shows expansion of the image of the failure cascade from the frame in FIG. 24E to now include the images of metabolic failure 995, renal failure 996, hemodynamic failure 997 and respiratory failure 998. This is the point wherein rescue begins in many patients monitored by today's EMR and monitoring systems. The introduction of fluid resuscitation 999 at this late frame of the image means that the fluid will likely have little effect on progression of the image.

Figure 25:
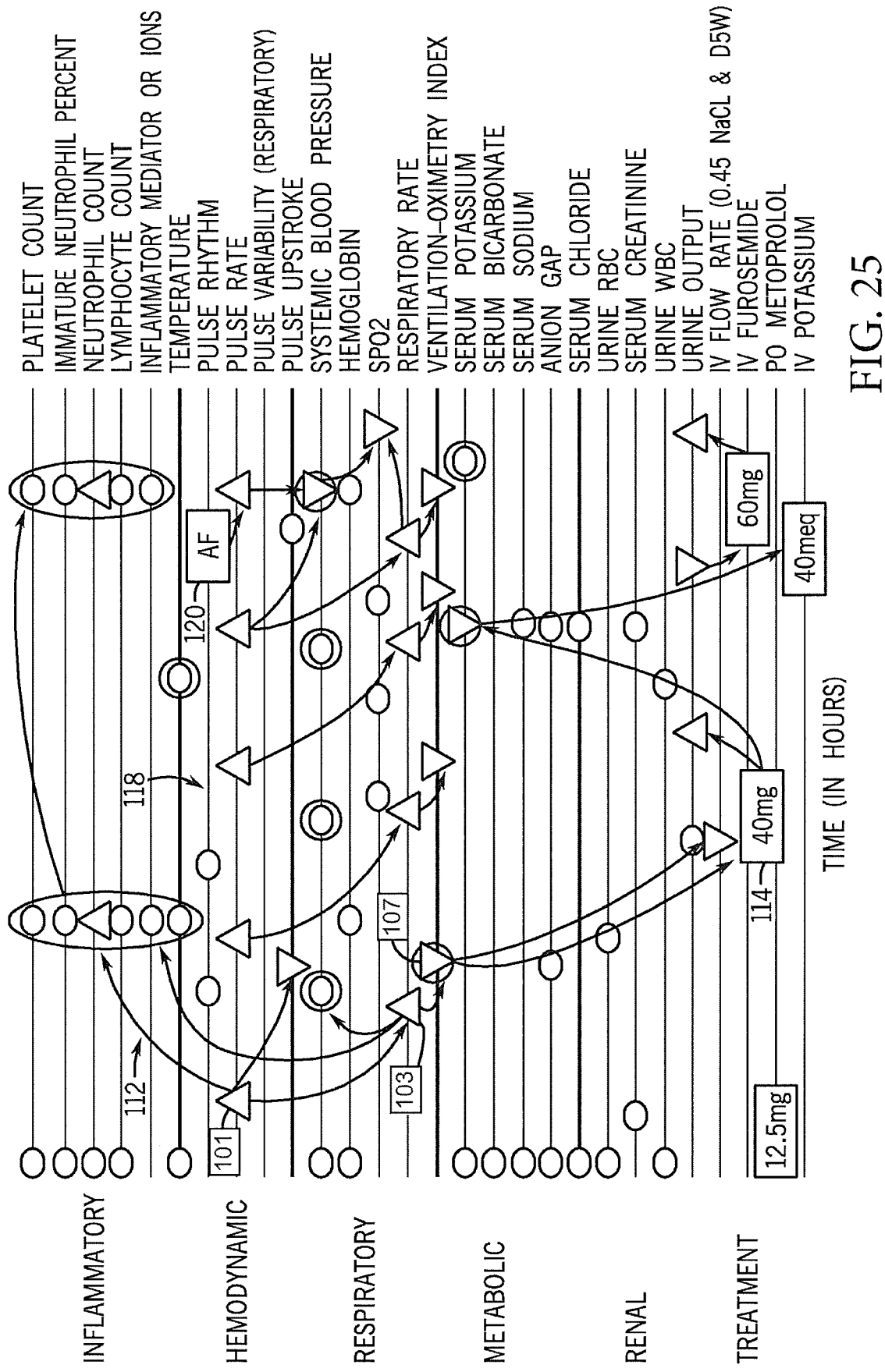
FIG. 25 is a general image including a plurality of timelines organized into groupings, which shows an image of congestive heart failure.

FIG. 25 shows a time lapsed image frame of the failure cascade of congestive heart failure. Note the first perturbation event detected by the processor is hemodynamic (a rise event in pulse rate 101), rather than inflammatory as in FIG. 24A. Then the next detected perturbation event is respiratory, a rise in respiratory rate 103 which combined with the rise in pulse 101 produces the first relational binary. Note also there is a fall in the ventilation indexed oximetry value 107 producing a second relational binary with the rise in respiratory rate 103. The rise in respiration rate 103 is the beta event of the first relational binary and the alpha event of the second relational binary. Together these two joined relational binaries form an image 110, which may be followed back to the initial onset of the image of the nascent congestive heart failure cascade 112. Treatments including furosemide 114 and metoprolol 116 are initiated fairly close to the onset of the image of the nascent cascade 112 but are not effective in preventing subsequent occurrence of an image of a progressive cascade 118. This image of a progressive cascade 118 is constrained by the both the components and length of the MPPC. The Patient safety processor upon detection of this image may search for the fundamental cause of the cascade progression, as by automatically ordering cardiac enzymes (not shown), and other tests if the safety committee of the hospital desires this type of testing proactivity in this setting. Note the cascade 118 includes the development of atrial fibrillation 120 and subsequent further deterioration.

Figure 26:
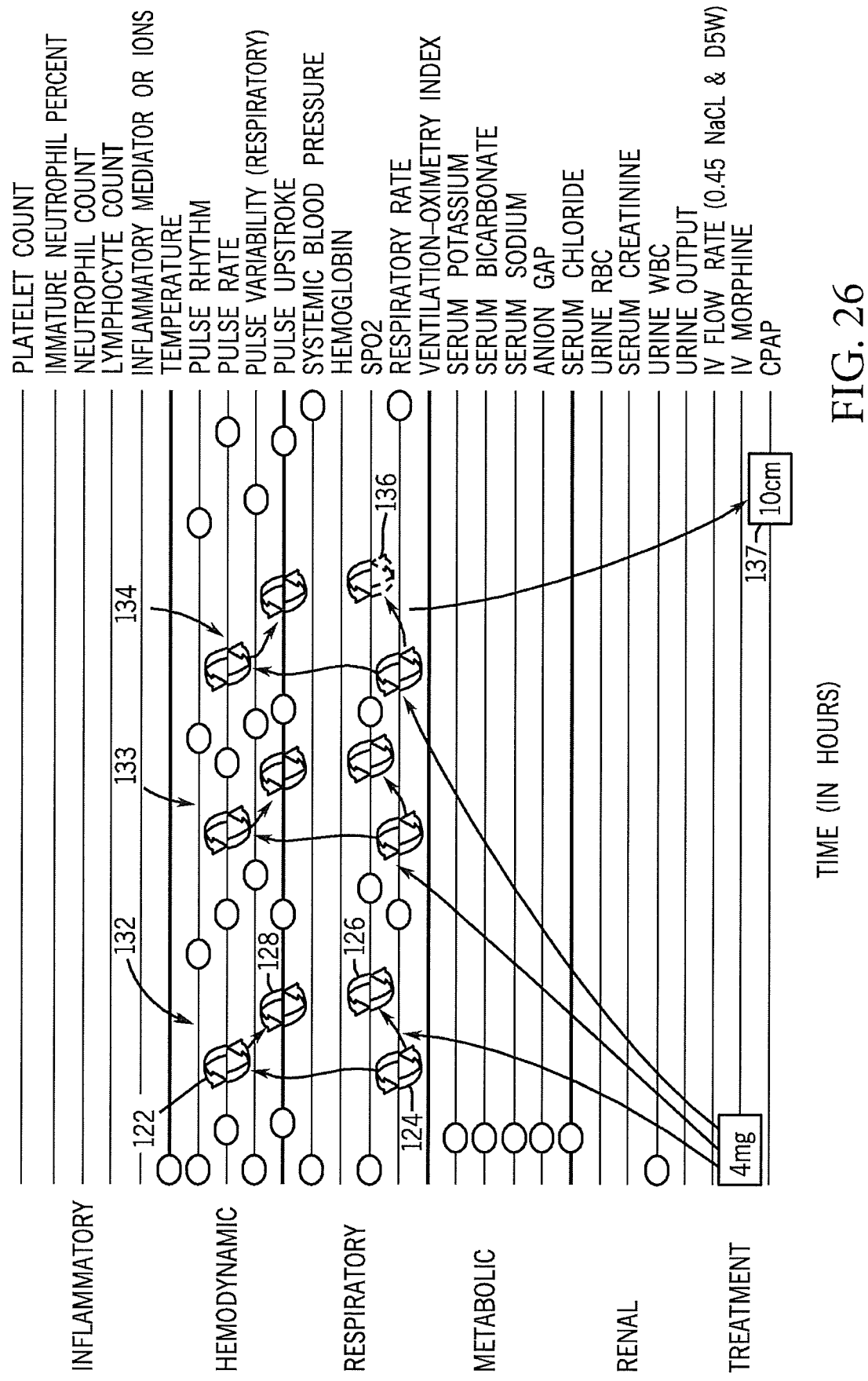
FIG. 26 is a general image including a plurality of timelines organized into groupings, which shows an image of sleep apnea.

FIG. 26 shows an image frame of sleep apnea. Note the first perturbation events occur in a group including a repeating occurrence of events within the pulse channel 122, respiratory channel 124, $SPO_2$ 126, and pulse upstroke channel 128. These occur after the initiation of a narcotic dose of 3 mg IV 130. The aggregated images showing cycling, a specific species of repeating occurrence, 132 then repeats to produce second such images 133 and third such images 134. The $SPO_2$ cycle 135 portion of the third images showing cycling 134 becomes more severe with recovery failure 136. CPAP treatment 137 is given timely and no further narcotic is given. Note, in this case, there is no image of an expanding cascade or progressively declining respiratory rate or declining $SPO_2$ to indicate life-threatening narcotic induced sustained hypoventilation. On later review as in morning report or with teaching rounds the entire MPPC, which contain this frame, may be reviewed by moving along a fast framed image to better visualize the subtleties of the progression. Furthermore the physician or nursing group may drill down to see that actual time series (as, for example, by right clicking on the SPO$_2$ repeating occurrence symbol 137). The decision as to whether or not the treatment in this case rendered timely care may be assessed. In an example, the physicians in the session may petition the patient safety committee to adjust the processor 394 to provide a recommendation for earlier automatic RT department notification, along with the nurse notification when images such as those defined in the early portion of this motion picture are present. In this way the Patient safety processor becomes an integral part of the continuous quality improvement actions of the hospital system with the goal being to move treatment and testing leftward into the earliest frame, which provides sufficient image support for the treatment or testing. The goal is to a continuing move toward earlier treatment of the source of the early perturbations before the cascade develops. According to one aspect, the processor 394 is integrated into the continuous quality improvement process and the processor 394 becomes an integral part of the hospitals quality improvement committee meetings and a major source of hospital wide as well as focused analysis and a mechanism to rapidly institutionalize quality improvement focused change.

Figure 27:
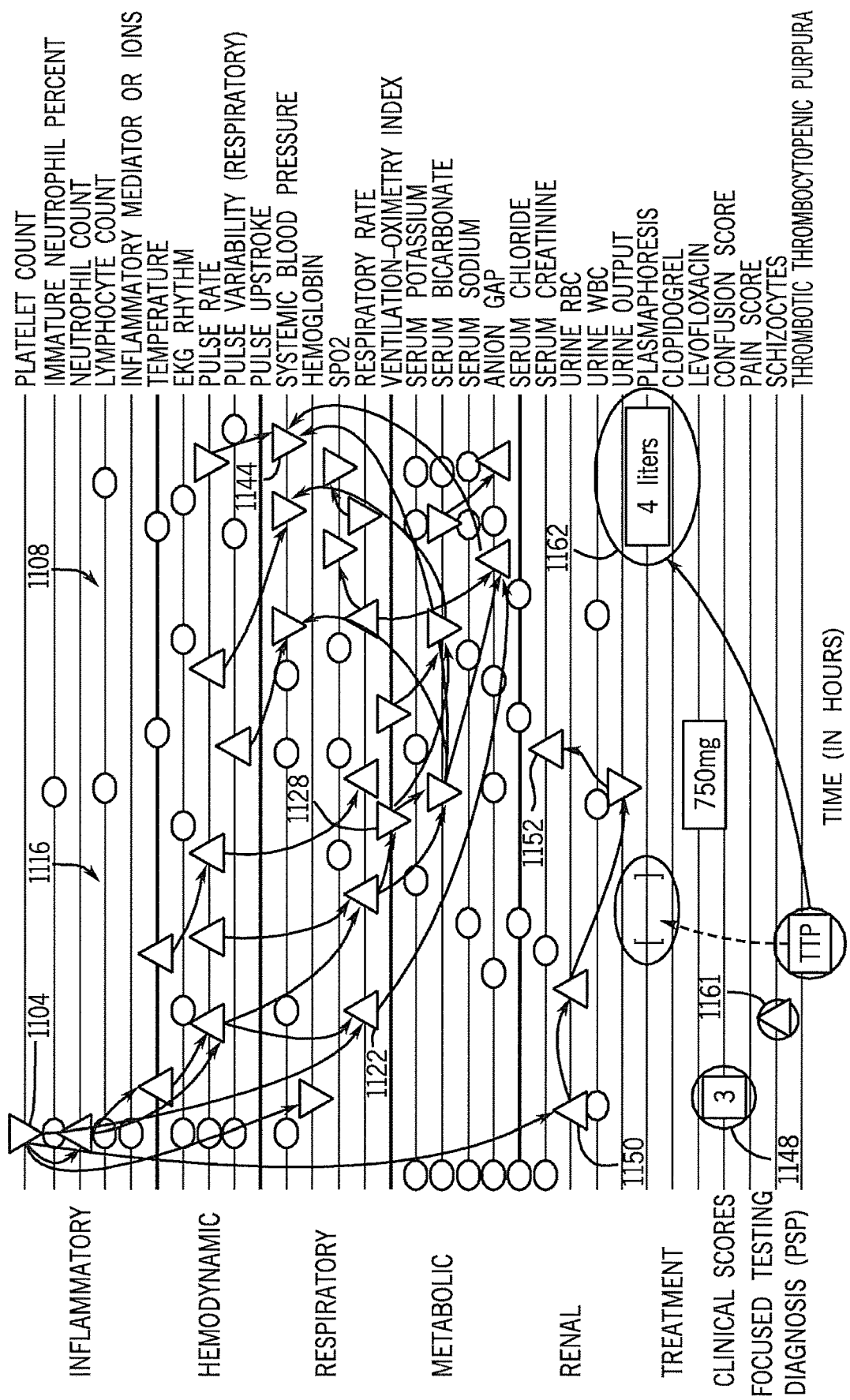
FIG. 27 is a general image including a plurality of timelines organized into groupings, which shows an image of thrombotic thrombocytopenic purpura.

FIG. 27 shows an image frame indicative of a high confidence of thrombotic thrombocytopenic purpura (TTP) a rare thrombotic and inflammatory condition that mimics the image of septic shock. TTP may be caused by the inhibition of ADAMTS enzyme by autoantibodies but this disease may also be rarely triggered by the very common drug clopidogrel. TTP often occurs within 2 weeks of drug initiation and may result in complications if not detected.

Unfortunately, TTP shares many of systemic response features of the very common disorder of sepsis (FIG. 15), which also causes thrombocytopenia. Since sepsis is a much more common condition, misdiagnosis of sepsis in the presence of TTP is a high possibility; furthermore, as with most pathophysiologic failures, both processes may coexist in a single patient along with other related conditions such as systemic lupus erythematosis and pancreatitis. Despite the fact that the moving images of failure in TTP and sepsis are similar, misdiagnosis of sepsis in the presence of TTP may be serious since TTP may not respond to antibiotic treatment.

Since TTP is associated with the accumulation of large multimers of Von Willebrand factor which damaging red blood cells and induce extensive micro vessel thrombosis producing confusion, renal failure and microangiopathic anemia which is associated with sentinel schizocytes which may be detected in the peripheral smear of blood (if the diagnosis is suspected and the test is ordered). Thrombocytopenia, renal failure, and hematuria may appear earlier in this process than with sepsis but these early findings are only an "image clue" and does not differentiate the two moving images. The decision to diagnosis a rare condition instead of a common one on the basis of a clue is a dangerous human tendency and a pitfall, which may result in patient complications. Alternatively the decision to diagnosis a common condition despite the clue because as the trite medical student saying goes "common condition occurs commonly" is equally dangerous. Indeed it is tragic that patient have to die because of such trite and oversimplified thinking. However it is the nature of many humans often approaches the analysis of overwhelming complexity with unknowingly capricious, summary judgment. This combined with the overlapping complexity of disease and healthcare is one of the most important reasons that comprehensive real-time physiologic and care rendering by the generation of digital MPPC and care is important.

The MPPC suggestive of TTP may be generated by the processor, with the processor indicating an image consistent with the possibility of sepsis and/or TTP and other less likely conditions such as an acute vasculidity. The processor may output non-specific characterizations of the image such as "image consistent with a life threatening acute or sub-acute thrombotic and inflammatory augmentation" and may present a differential diagnosis of the processes, which may generate such an image.

Also, as for example upon the detection of a threshold frame or frames, automatically order the peripheral smear, blood cultures, urine cultures, sputum cultures, Chest X-Ray, ANA, pancreatic enzymes, renal sediment, and ANCA study to enlarge and fill in the gaps of the image as rapidly as possible. It is the hospital experts who will ultimately decide the cost effective balance of ordering these tests as defined by the position the tests are ordered along the cascade. If desired the reports from the Chest X-Ray may include a section which will appear as a time series (as for example a step function). The radiologist in the interpretation (and in comparison with the last test and the last number selected by the last reading radiologist) may enter an indication of pulmonary infiltrate, pulmonary edema, and the like and may indicate a value between 1 and 5 which may result in a step change of the processor 394 from the last test. In this way the results of studies such as Chest X-Rays and other such interpreted tests become a source for dynamic time series rendering and incorporation into the imaging process. This will also provide an objective tool for comparing subjective quantification between radiologists and between various testing modalities in relation to the actual MPPC thereby identifying radiologists who are not generating reasonably reproducible or comparable subjective quantification in relation to themselves, others or the MPPC. In an example if a radiologist consistently calls the level of pulmonary edema a 1 or 2 in patients who have MPPCs consistent with of acute severe CHF and acute severe pulmonary edema or if the radiologists quantification consistently fails to follow or predict the clinical course then instruction can be provided or in the alternatively it can be recognized by the processor 394 that the input from that specific radiologist is not useful in further defining the images along the processor 394.

The presence of an image including images defining a failure cascade 1108 including inflammatory-hemodynamic respiratory-augmentation 1116 with an early fall in platelet count 1104, a fall in the Ventilation oximetry Index (VIO) 144, a fall or threshold value of hemoglobin 1144, an rise or threshold value of a confusion score 1148, and/or a rise or threshold value of red blood cells in the urine 1150, and/or a rise or threshold value of Creatinine 1152. Together the combination of images produces a MPPC suggestive of the possibility of TTP and/or sepsis and/or other less common processes. For example, if the patient had just received blood it would suggest a possible transfusion reaction.

It is not as important for the processor 394 to make the diagnosis as it is for the processor 394 to indicate to the healthcare worker the gravity of the image, a differential diagnosis as suggested by the image, and the general type and/or physiologic description of failure cascade present, and perhaps a notification that the detection by the processor 394 of this type of image requires prompt notification of the attending physician and transfer to ICU. If the image has insufficient binaries because results are not available to define enough beta components to define the presence of the image suggestive of TTP with a sufficient confidence level to take action, the unavailable tests are ordered upon the detection of the partial image in an attempt to complete the image. Note in FIG. 27, the detection of the images suggestive of the possible presence of a complete MPPC of TTP triggered the test for Schizocytes 1161 in an attempt to complete the TTP image. The detection of a threshold value step function, and/or rise in schizocytes combined with the rest of the image triggers the warning of the potential presence of TTP. In FIG. 27 reflects poor care because the action based on the processor 394's order for plasmaphoresis 1162 is physically carried out too late. This delay is automatically detected as is the outcome and the processor may be configured to provide an automatic report of variance to the quality improvement department of the hospital.

In this case, failure to rescue is not preempted because of human delay in physically following the orders of the processor 394. The delay in carrying out the order is determined by the processor 394 and the processor 394 may be programmed to up-indicate the warning upon increasing delay. To prevent this delay, the processor 394 may be programmed notify another station if action is not taken in response to detection of various evolving images such as the one in FIG. 27. These may be decided for example by the hospital quality improvement committees or by individual physicians or nurses if desired so that the processor 394 improves over time and may be adjusted to compensate for the diligence of the healthcare worker. The patient receives Levofloxacin early to cover the possibility of sepsis as the image was also consistent with sepsis and the healthcare workers decided to empirically treat for sepsis (albeit with somewhat limited antibiotic coverage). However, the cascade proceeds despite antibiotic therapy. Since a cascade is an image and the relationship of the cascade, its growth, and its features and its timing within an MPPC in relation to the dose, timing, and type of treatment also forms part of the MPPC, these relationships may be automatically assessed by the processor in real-time to determine if treatment is effective. The hospital safety committee or infectious disease committee may decide whether or not to reprogram the processor 394 to make antibiotic suggestions based on various ranges of images before the results of cultures are known.

FIG. 28 shows an overview image of perturbation onset and progression as derived from the time lapsed MPPC of FIG. 24A wherein the perturbations in each grouping are incorporated into an aggregate index along a single smoothed time series for each group. Note this is a typical progression of sepsis with initial involvement of the inflammatory group 160 then each other group is involved in progression. Note the late timing of the treatment 162 is particularly evident in this summary view derived from the more complex images.

Rather than or in combination with an index, if desired the processor may be programmed to provide an indication of the severity and number of the aggregate perturbations in each group. These may be for example designated by many enlarging or colored arrows, other icons, and/or timed instability scores, to name a few. Many such options may be included so that the user may define his or her preference to visualize the sequence and patterns of cascade progression across groups.

A range of expert and pattern recognition systems may be applied to analyze the images and the images generated by the image processor. These include the image Identification Processor. In one embodiment the image Identification Processor works with the image editor which allows the user to select the images for detection using for example a from a drag and drop interface. In an embodiment the drag and drop interface provides for the discretionary selection of, for example, the time-series type to be selected, then occurrences are selected on each time-series type in order and the ranges of relative positions and orders occurrences is selected. In this example, the image editor allows customization of the desired ranges for the components of the images (and therefore the ranges of the images themselves) to be selected as well as the response of the image Identification Processor to the detection of a given image and/or images. The image editor may allow for selecting the ranges of timing and order of the occurrences to generate a specific output such as a proposed diagnosis, warning, order for more testing or imitation or termination of treatment. The image Identification Processor may also be adaptive such that a physician inputs the diagnosis present, such as for example septic shock, with a given image. The physician may also capture a given image or set of images into the image editor to then select ranges about the occurrences within the image which also would have indicated the presence of septic shock so that the adaptive image processor may learn more quickly.

FIGS. 24, 25, 26, 27, and 29 represent a 2 dimensional "time lapsed" snapshot view four MPPC after they have proceeded to advance states. This view also provides an alternate user interface for the creation and editing of the image definition set. Researchers may use an image editor to create and manipulate image models such as those examples depicted in FIGS. 24, 25, 27, and 27.

Figure 29:
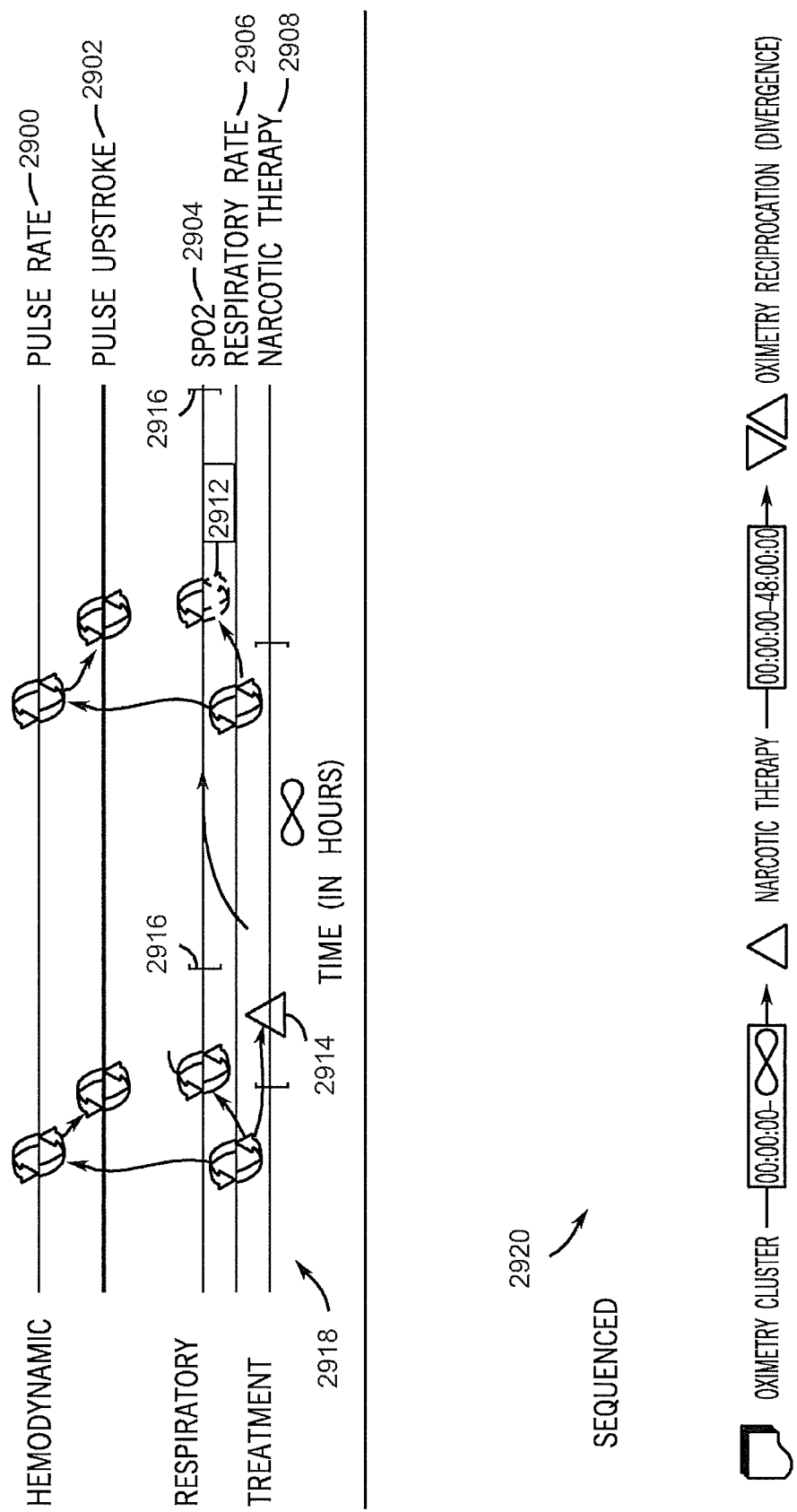
FIG. 29 is a split screen diagram of a drag and drop interface for constructing combined physiologic and treatment images for subsequent detection by the patient safety processor showing the construction of a motion picture indicative of narcotic associated recovery failure in the presence of sleep apnea.

In one embodiment researchers work from the top down to define images. Researchers begin by selecting a set of channels in which they want to "paint" the image. FIG. 29 depicts the image editor being used to "paint" the narcotic-induced ventilation instability image. Channels (2900, 2902, 2904, 2906, 2908) may be ordered in any number of ways, by sorting, categorizing or by simple drag-and-drop selection of location within the image editor. Channels may be duplicated (e.g. 2900, 2902, 2904, 2906, 2908) to expand the image so that the relationships may be defined in a non-overlapping way for complex definitions that define multiple relationships. The image editor maintains the relationships within and between defined elements within the channels regardless of their vertical location within the editor. Researchers then select a channel and the image editor presents a set of occurrences that are available which apply to the given channel. Researchers may select any of these elements and drop them on channel. Also, the researcher may create a new element at any point within a channel (for example using a right-click menu editor). Locations within the editor indicate relative locations in time between selected and/or created elements. If an occurrence which spans multiple channels is dropped on a location, the image editor determines the additional channels to be added. The location of the corresponding event is determined as the midpoint of the search window definition. The entire window is shown as a set of parenthesis 2916 indicating the range of the search window relative to the corresponding event, in this case a treatment event with an IV narcotic 2914. Search windows are shown only within the beta channel of the relational binary and the event itself is show within the midpoint of the search window. If an event is both a beta and an alpha event the search window displayed is around the event is specific to the event when it is participating as a beta event. Search windows may be suppressed within the editor and/or shown only within the relational binary currently selected due to the fact that a single event may be the beta of any number of binaries. Individual events may be dropped onto a channel or created on a channel. New event types may be defined within the image editor. Events may be connected with a drag-and-drop selection or with an alpha and beta click selection, for example to define new event binary types.

The image editor creates and modifies image definition sets. Furthermore, the image editor works in concert with both the convergence editor and the event editor to create and modify the binary and event definition sets. In one embodiment (shown in FIG. 29), the definition of image is accomplished with a split-screen view showing the image editor in the top pane 2918 while the image definition editor is in the lower pane 2920 showing an alternative type of image diagram. These two models are completely synchronized with changes in one immediately reflecting the change in the other.

In one embodiment researchers work from the bottom up to define failures from a set of time series. Researchers may begin with a set of actual time series from patients diagnosed with known failures, with a set of time series generated by the processor to simulate certain conditions or a set of time series simulating no perturbation at all within a patient. This set of time series may be designated as immutable (for example with the set of actual time series) or may be edited to provide a sample of the patterns being defined. Researchers may select portions of the time series, which the image editor then will analyze to provide candidate event definitions. Alternatively the researcher may select parameters to define an event and the time series displayed will indicate the results of that definition overlaid on top of the time series to provide visual guidance to the researcher. Once the researcher completes the definition of an event the image editor will compare that definition with other definitions within the same channel. If similar patterns are found the researcher is alerted and allowed to create a new event type or select one of the event types already selected. If the event is a relational event, the researcher may select a corresponding event from which relational parameters may be defined and experimented with or the researcher may simply define a function (e.g. >2× Relative Magnitude). Once an event has been fully defined then the researcher may choose to relate the event to another event within the image or to a search window within the image (e.g. to indicate a missing or null event). The researcher may indicate that a processor-ordered event as the beta of a relational binary. Groups of events and relational binaries or any other occurrence may then be selected to define an images. images already defined within the image definition set are highlighted such that they may be included into the image the researcher is working with or the researcher may simply select to alter its definition. Access into the occurrence property Subsystem is available and the expression editors included indicate immediate results with respect to the current image or other occurrences selected. This allows the image editor to work on all aspects of the image including scope definition, qualification rules to name a few.

In one embodiment, the image editor may be presented with a large collection of time series sets provided with the indication of the presence or absence of a particular known image. The image editor creates a set of candidate definition sets refining them to create the right specificity and sensitively to match the sample set. Once the best-fit definition sets are created, a second large collection of times series sets are provided with the indication of the presence or absence of a particular known image. The image editor first uses the candidate definition set, determining sensitivity and specificity, and then refines the definition set to be better suited if possible to both the first and the second collection of sample data. This process may be executed iteratively until a best-fit set of definition sets is created or the process is deemed not to be asymptotic and is abandoned.

In one embodiment the image may be "played" or executed by the image editor as an MPPC to provide further time-specific markers. A default execution of an image is "played" by placing all events as specified in their default (e.g. midpoint) location within their respective search windows as defined by the image definition. A sample result of this is displayed in FIG. 24B. Once the image is played vertical markers are placed within the timeline as in FIG. 24B to indicate progressive states within an evolving image. In this way, the image definition may be provided the specifications by which the image state may be identified and displayed within the Patient Safety Monitor. FIGS. 24C, 24D, 24E and 24F show the 4 views of an image evolving within the Patient Safety Monitor over time. The Patient safety processor identifies one or more of the diseases, disorders, or cascades which are most consistent with the present state of the image and displays it at the bottom of the monitor (along with differential diagnosis if desired).

In an alternate and/or complimentary embodiment, the image editor provides the ability to split the execution of an image into multiple intermediate and/or end states. Each different branch within the image definition may be defined as a state within an image or a different, albeit related, image. Trees of related images may be composed to provide alternative evolutions of failure within the image definition.

Figure 16:
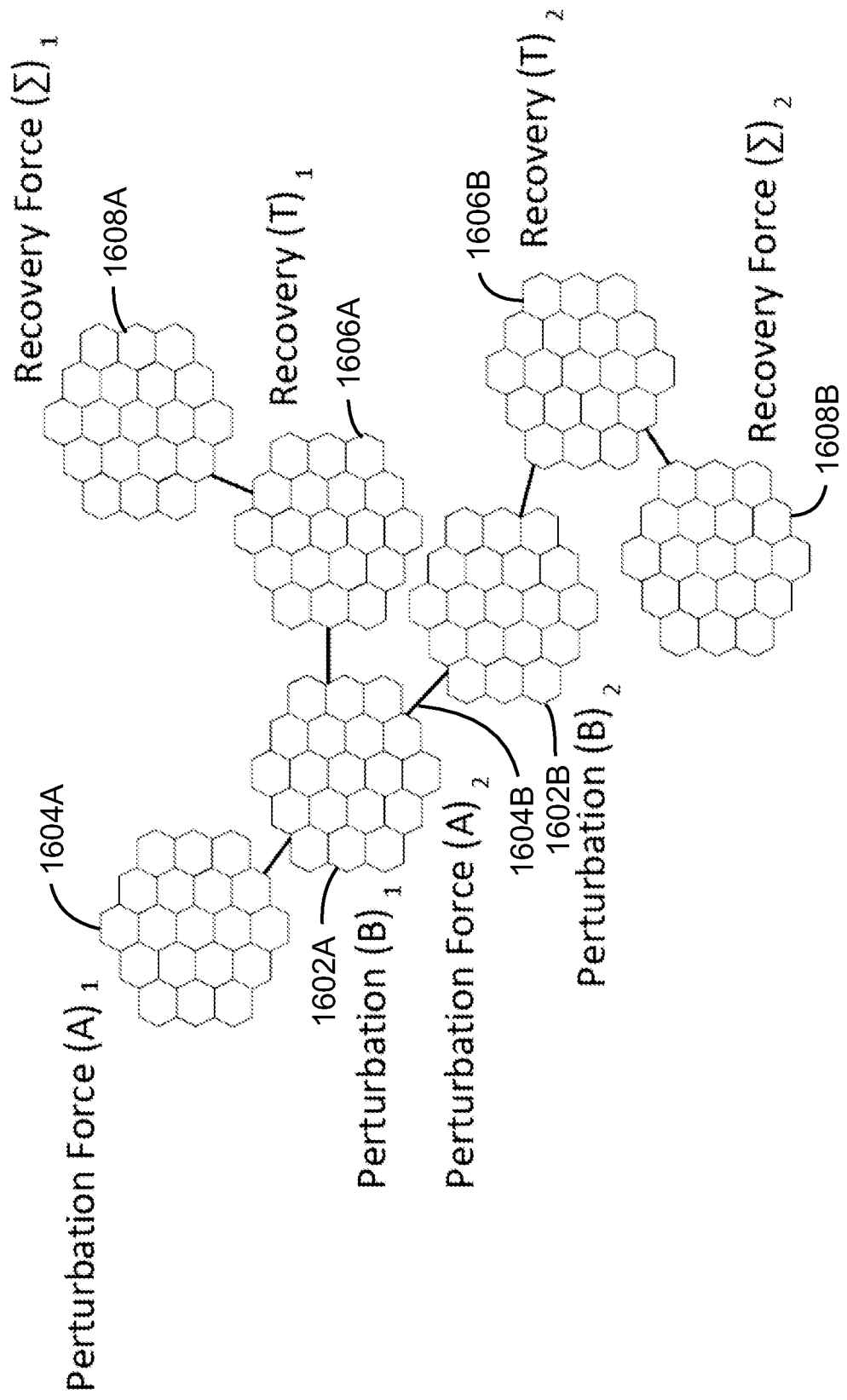
FIG. 16 depicts the two linked quaternaries wherein the perturbation of the first quaternary is the perturbation force of the second quaternary displayed as an image of perturbations, recoveries, perturbation forces and recoveries represented as clustered hexagons.

In one embodiment, as shown in FIG. 15, hexagons 1502A, 1502B are grouped such that the perturbation or recovery are placed in the center 1504A, 1504B of additional hexagons responsive to the features and related quanta of the perturbation or recovery at the center of the group. Any number of features can be visually aggregated in this way. In one embodiment, hexagons for the features are arranged spatially within the hexagon associated with the perturbation or recovery to which they are associated. Once hexagons are visually aggregated in this way, as shown in FIG. 15, these clusters of hexagons can be themselves aggregated according to relationships between perturbations, perturbation features, recoveries and/or recovery features. For example, as shown in FIG. 16, a pair of quaternaries (originally depicted in FIG. 6) can be displayed as an image of perturbations 1602A, 1602B, recoveries 1606A, 1606B, perturbation forces 1604A, 1604B, and recovery forces 1608A, 1608B using clustered hexagons as depicted in FIG. 15. FIG. 16 depicts a pair of related quaternaries showing that, in one embodiment, quaternaries provide a spatial link which can be extrapolated to a greater number of quaternaries including all identified.

Figure 17:
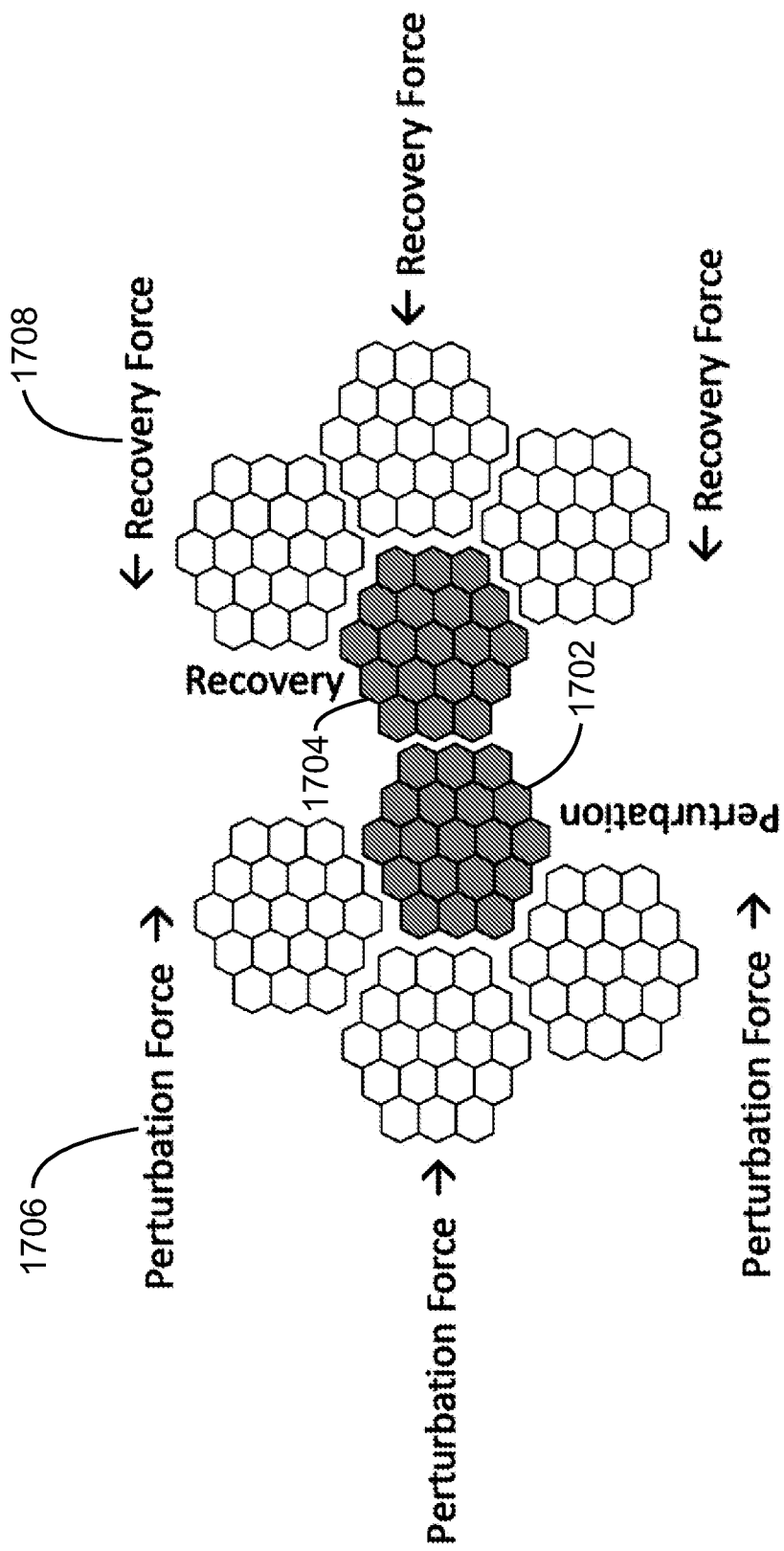
FIG. 17 depicts a perturbation/recovery pair visually decorated with the associated forces identified in which hexagon clusters for each perturbation, recovery and force are shown.

In one embodiment, as shown in FIG. 17, perturbation 1702/recovery 1704 pairs are visually decorated with the associated forces 1706 and 1708 identified. Hexagon clusters for each perturbation, recovery and force are fully expanded in the method depicted in and described by FIG. 15. In one embodiment these clusters are arranged spatially to display the direction of the forces identified.

Figure 18:
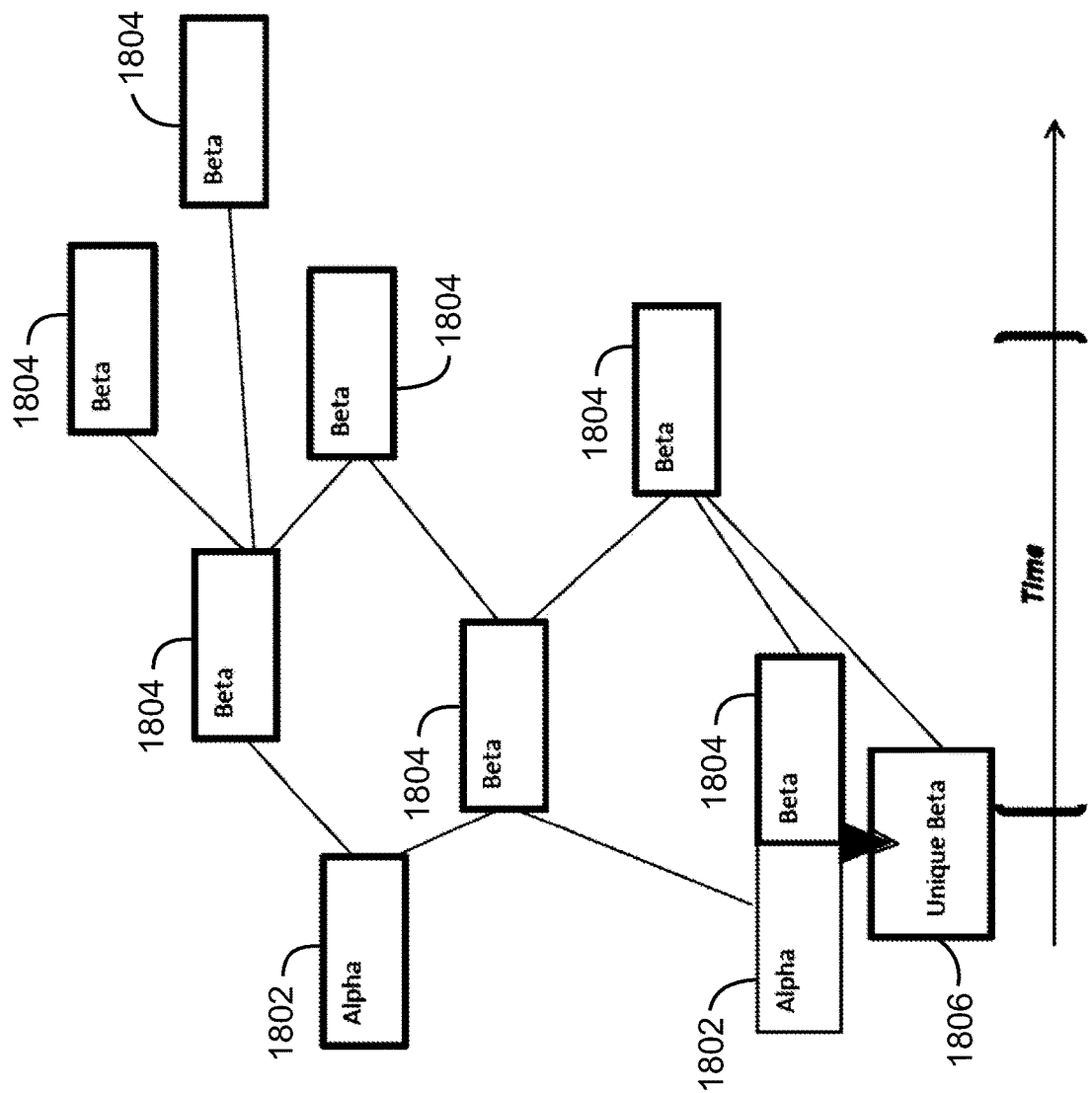
FIG. 18 depicts a schematic of a complex time dimensioned pathophysiologic cascade with relationally enabled links in which a unique binary object enables a connection to an otherwise non-connectable beta.
Figure 18:
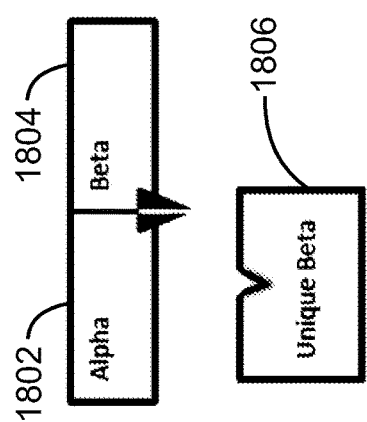

In one embodiment, a schematic of a complex time dimensioned pathophysiologic cascade with relationally enabled links is displayed as shown in FIG. 18. Using a combination of an alpha 1802 and beta 1804 the processor 200 may generate a unique binary object 1806, which enables relationally enabled connection to an otherwise non-connectable beta (which can also be another binary). Such combinations may also be defined to classify a rise or a fall to whether it represents a perturbation or recovery from a prior perturbation (which may have occurred before the data collection. For example, a fall in absolute neutrophils may be a perturbation (for example, when the neutrophils have been destroyed or sequestered in the battle against the microorganism) or a recovery (as an indication of a return of the absolute neutrophil density toward the normal range as the infection abates). If the processor 200 detects a rise in bands concomitant with the fall in absolute neutrophils it may generate a unique "decoherence binary" comprised of the rise in bands with the fall in absolute neutrophils. Upon the identification of this decoherence binary, the processor 200 classifies the fall in absolute neutrophils as a perturbation and not a recovery.

Figure 19:
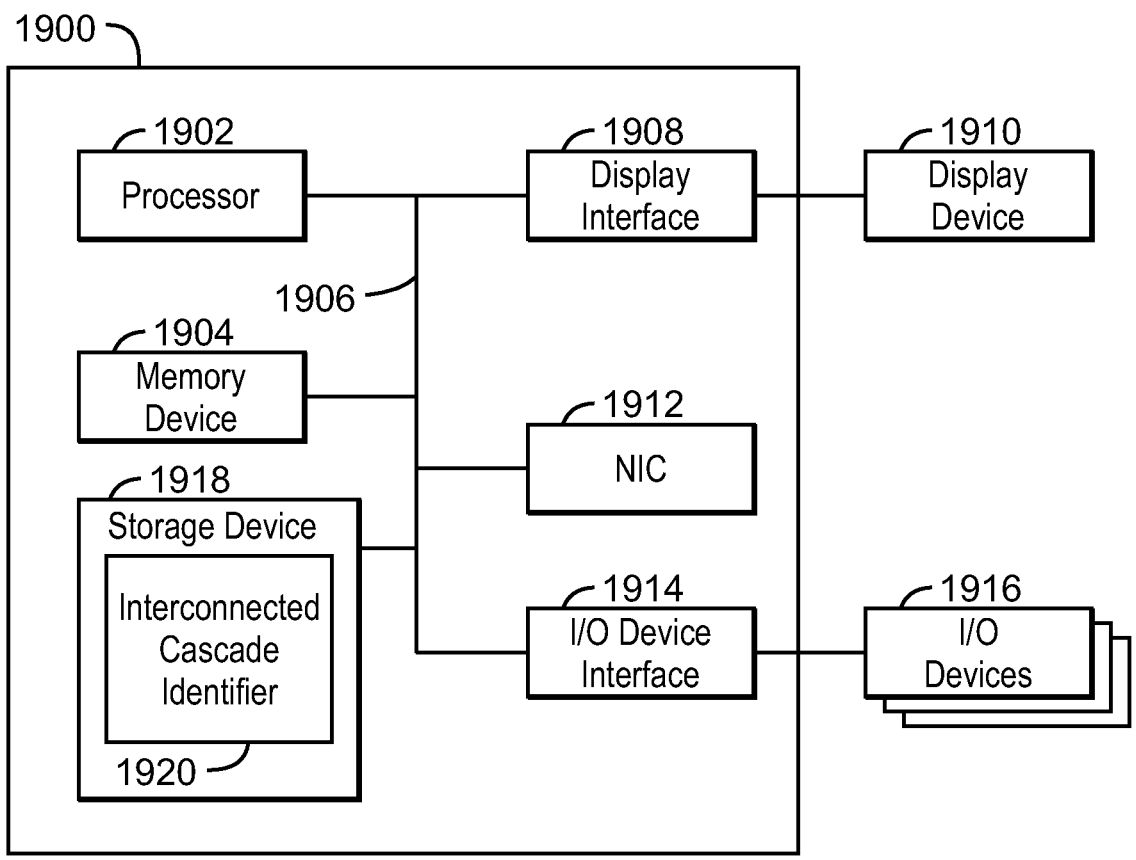
FIG. 19 is a block diagram of an example of a computing device that can identify interconnected cascades.

FIG. 19 is a block diagram of an example of a computing device that can identify interconnected cascades. The computing device 1900 may be, for example, a hospital monitor, mobile phone, laptop computer, desktop computer, or tablet computer, among others. The computing device 1900 may include a processor 1902 that is adapted to execute stored instructions, as well as a memory device 1904 that stores instructions that are executable by the processor 1902. The processor 1902 can be a single core processor, a multi-core processor, a computing cluster, or any number of other configurations. The memory device 1904 can include random access memory, read only memory, flash memory, or any other suitable memory systems. The instructions that are executed by the processor 1902 may be used to implement a method that can identify interconnected cascades.

The processor 1902 may also be linked through the system interconnect 1906 (e.g., PCI®, PCI-Express®, HyperTransport®, NuBus, etc.) to a display interface 1908 adapted to connect the computing device 1900 to a display device 1910. The display device 1910 may include a display screen that is a built-in component of the computing device 1900. The display device 1910 may also include a computer monitor, television, or projector, among others, that is externally connected to the computing device 1900. In addition, a network interface controller (also referred to herein as a NIC) 1912 may be adapted to connect the computing device 1900 through the system interconnect 1906 to a network (not depicted). The network (not depicted) may be a cellular network, a radio network, a wide area network (WAN), a local area network (LAN), or the Internet, among others.

The processor 1902 may be connected through a system interconnect 1906 to an input/output (I/O) device interface 1914 adapted to connect the computing device 1900 to one or more I/O devices 1916. The I/O devices 1916 may include, for example, a keyboard and a pointing device, wherein the pointing device may include a touchpad or a touchscreen, among others. The I/O devices 1916 may be built-in components of the computing device 1900, or may be devices that are externally connected to the computing device 1900.

In some embodiments, the processor 1902 may also be linked through the system interconnect 1906 to a storage device 1918 that can include a hard drive, an optical drive, a USB flash drive, an array of drives, or any combinations thereof. In some embodiments, the storage device 1918 can include an interconnected cascade identifier 1920. The interconnected cascade identifier 1920 can process medical data derived from a patient or a medical records repository and compose interconnected cascades of causation of physiological occurrences by linking or grouping at least four elements, wherein the elements comprise a perturbation; at least one perturbation force which is capable of inducing and may have induced the perturbation; a recovery; and at least one recovery force which is capable of inducing and may have induced the recovery of said perturbation.

It is to be understood that the block diagram of FIG. 19 is not intended to indicate that the computing device 1900 is to include all of the components shown in FIG. 19. Rather, the computing device 1900 can include fewer or additional components not illustrated in FIG. 19 (e.g., additional memory components, embedded controllers, additional modules, additional network interfaces, etc.). Furthermore, any of the functionalities of the interconnected cascade identifier 1920 may be partially, or entirely, implemented in hardware and/or in the processor 1902. For example, the functionality may be implemented with an application specific integrated circuit, logic implemented in an embedded controller, or in logic implemented in the processor 1902, among others.

Figure 20:
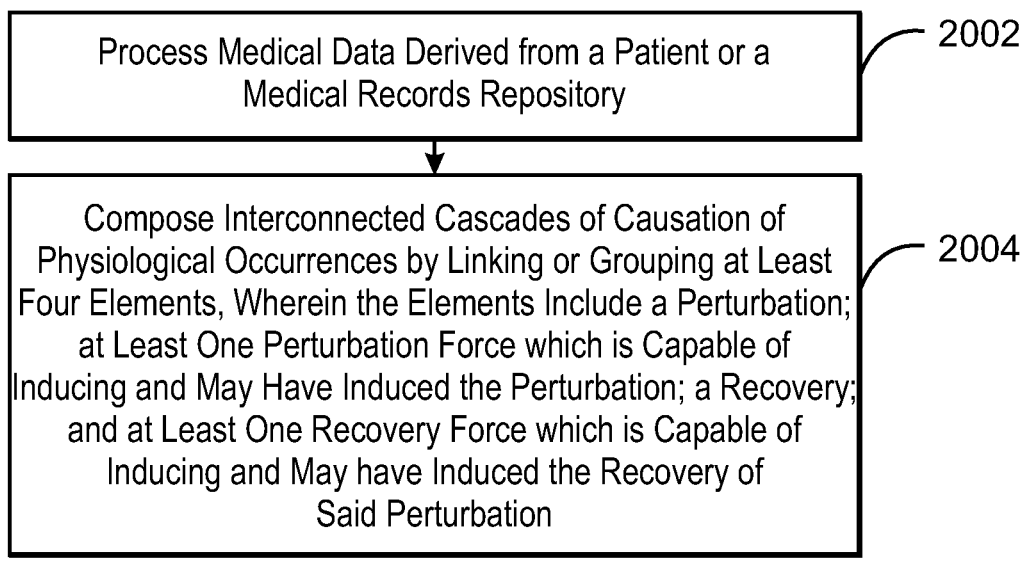
FIG. 20 is a process flow diagram of an example method for identifying interconnected cascades.

FIG. 20 is a process flow diagram of an example method for identifying interconnected cascades. The method 2000 can be implemented with a computing device, such as the computing device 1900 of FIG. 19.

At block 2002, the interconnected cascade identifier 1920 can process medical data derived from a patient or a medical records repository. At block 2004, the interconnected cascade identifier 1920 can compose interconnected cascades of causation of physiological occurrences by linking or grouping at least four elements, wherein the elements include a perturbation, at least one perturbation force which is capable of inducing and may have induced the perturbation, a recovery, and at least one recovery force which is capable of inducing and may have induced the recovery of said perturbation.

The process flow diagram of FIG. 20 is not intended to indicate that the operations of the method 2000 are to be executed in any particular order, or that all of the operations of the method 2000 are to be included in every case. Additionally, the method 2000 can include any suitable number of additional operations.

One of ordinary skill in the art will appreciate the technical effect described herein which enables identifying interconnected cascades. Some embodiments described herein have the effect of composing interconnected cascades of causation of physiological occurrences by linking or grouping at least four elements.

Figure 21:
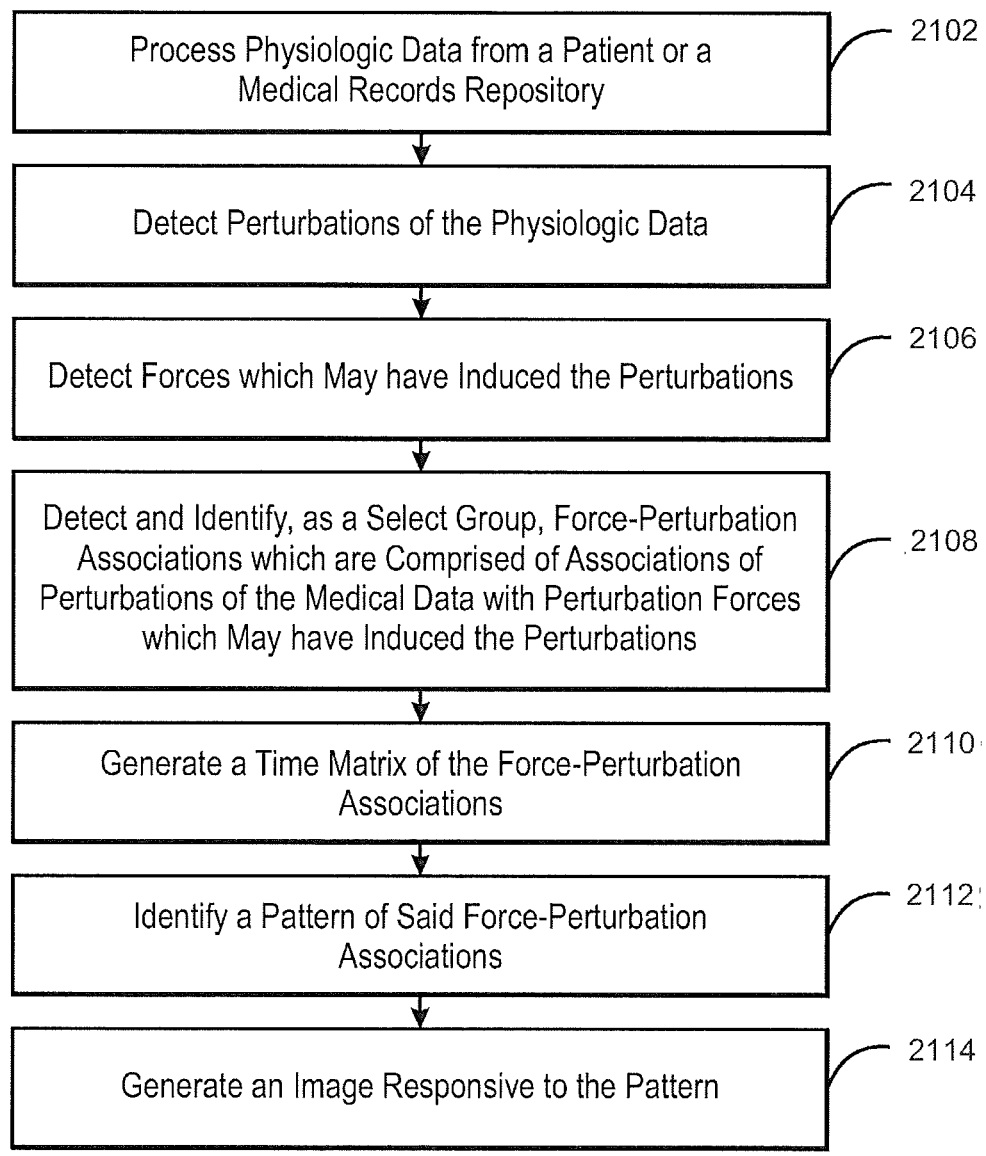
FIG. 21 is a process flow diagram of an example method for generating an image of physiologic data responsive to causation of an adverse condition.

FIG. 21 is a process flow diagram of an example method for generating an image of physiologic data responsive to causation of an adverse condition. The method 2100 can be implemented with a computing device, such as the computing device 1900 of FIG. 19.

At block 2102, an image generation module can process physiologic data from a patient or a medical records repository. At block 2104, the image generation module can detect perturbations of the physiologic data. At block 2106, the image generation module can detect forces which may have induced the perturbations. At block 2108, the image generation module can detect and identify, as a select group, force-perturbation associations which are comprised of associations of perturbations of the medical data with perturbation forces which may have induced the perturbations. At block 2110, the image generation module can generate a time matrix of the force-perturbation associations. At block 2112, the image generation module can identify a pattern of said force-perturbation associations. At block 2114, the image generation module can generate an image responsive to the pattern.

The process flow diagram of FIG. 21 is not intended to indicate that the operations of the method 2100 are to be executed in any particular order, or that all of the operations of the method 2100 are to be included in every case. Additionally, the method 2100 can include any suitable number of additional operations.

One of ordinary skill in the art will appreciate the technical effect described herein which enables the analyzing of complex datasets of medical records. Some embodiments described herein have the effect of detecting forces which may have induced perturbations, generating a time matrix based on force-perturbation associations and generating an image responsive to a pattern identified in the time matrix.

Conditional language used herein, such as, among others, "can," "may," "might," "could," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated may be made without departing from the spirit of the disclosure. As will be recognized, certain embodiments described herein may be embodied within a form that does not provide all of the features and benefits set forth herein, as some features may be used or practiced separately from others. The scope of some embodiments is indicated by the appended claims rather than by the foregoing description. All changes which come within the meaning and range of equivalency of the claims are to be embraced within their scope.

The term laboratory measurements, values, and densities may comprise calculated values or may comprise the actual measurements and values indicative of particle densities, particle characteristics, or other physical components or characteristics in, or of, the sample under test such as the blood. The analog or digital outputs of automated measurements derived from automated systems (such as automated hematology or chemistry instrumentation) may be received and converted to time series when multiple sequential samples are available. Such measurements may be derived from florescence, impedance volume, for example with direct current, radiofrequency conductivity with impedance aperture, laser light scattering, photon spectral absorption, antibody probes, PCR amplification, chemical reactions, or many other methods as are well known in the art. In many situations such measurements actually comprise the densities or characteristics of the biologic particles but have not yet been formally converted into the formal density or characteristic values which healthcare workers are accustomed to seeing, for example in an automated complete blood count. In one embodiment these signal may be used directly by the processor 200 to generate, perturbations, forces, and recoveries and features of perturbations, forces, and recoveries before converting them into the formal density or characteristic values which healthcare workers are accustomed to seeing With this approach, time series or timed groupings of these measurements or values may be generated. Perturbations, features of perturbations, forces, features of forces, and recoveries and features of recoveries may be identified in these signals and/or converted into objects. These may be used to derive image components, images, sequenced of images and/or mapped and presented to an image recognition system. These may be combined with the calculated or estimated density values to create a more comprehensive map. Such measurements render rawer outputs which may be plotted directly and although some represent density equivalents others contain features or relational patterns over time which may have been lost in the quantification processes associated with conversion of these analog or digital signals into to the formal density or characteristic values which healthcare workers are accustomed to seeing.

EXAMPLE EMBODIMENTS

In some embodiments, a patient monitoring system comprises at least one processor programmed to process medical data derived from a patient or a medical records repository and to compose interconnected cascades of causation of physiological occurrences by linking or grouping at least four elements. The elements can include a perturbation, at least one perturbation force which is capable of inducing and may have induced the perturbation, a recovery, and at least one recovery force which is capable of inducing and may have induced the recovery of said perturbation. In some embodiments, the four elements are linked or grouped by the at least one processor to generate a quaternary. In some examples, the quaternary is characterized as solved or unsolved. In one embodiment, the quaternary is characterized as solved when the processor detects all four elements, determines the at least one perturbation force is compatible with the perturbation, and determines the at least one recovery force is compatible with the recovery.

In some embodiments, a perturbation in the quaternary comprises a potential perturbation force in another quaternary. In one example, the perturbation in the quaternary comprises a potential recovery force in another quaternary. Furthermore, any element in the quaternary can include a potential element in a different quaternary. In addition, interconnected cascades of quaternaries can be identified by the processor as one or more candidate causation models for a patient condition. In some examples, at least one candidate apical force is determined by the processor as a first or an early perturbation force within a cascade. Additionally, at least one processor can identify a diagnosis based on the identification of the apical force.

In some embodiments, at least one causation model is displayed to a healthcare worker and at least one processor compares at least two causation models. In one example, at least one processor determines at least one preferred causation model. In some embodiments, at least one processor identifies, displays, and marks unsolved quaternaries so that a user can readily recognize the quaternaries as unsolved. In some examples, at least one processor is programmed to at least one of: order or recommend testing, or order or recommend the timing or frequency of testing, when at least one unsolved quaternary is identified.

In some embodiments, a number of unsolved quaternaries are tracked by the processor as a time series. In one example, at least one processor is to initiate an alert based on a number of unsolved quaternaries. In addition, solved and unsolved quaternaries can be identified by the at least one processor in a color weather map visualization. In some embodiments, at least one processor detects a defined or selected solution to the quaternary. Furthermore, a number of unsolved quaternaries can be tracked by at least one processor as a time series.

In some embodiments, a patient monitoring system comprises at least one processor programmed to process medical data and generate a time matrix comprising the medical data. The processor can also be programmed to detect a perturbation grouping comprising perturbations and perturbation forces which induced said perturbations along the time matrix, wherein the perturbation grouping has an onset. In addition, the processor can be programmed to generate an image of, or responsive to, the perturbation grouping and detect a recovery grouping comprising recoveries and recovery forces which induced said recoveries along the time matrix, the recovery grouping having an onset, wherein the onset of the recovery grouping occurs after the onset of the perturbation grouping. Furthermore, the processor can be programmed to output a motion image responsive to the time matrix which displays the onset of the perturbation grouping followed by the onset of the recovery grouping.

In some embodiments, a system for rendering images of abnormal medical data comprises a processor programmed to convert the medical data into a time series matrix of objects comprised of linked objects forming quaternaries, said quaternaries being comprised of perturbations, forces which induced the perturbations, recoveries, and the forces which induced the recoveries. The processor can also be programmed to store the time series matrix of objects in a data repository and generate images of, or responsive to, the matrix. In some examples, the processor is programmed to add additional quaternaries to the stored time series matrix over time.

In some embodiments, a patient monitoring system for generating an image of physiologic data responsive to causation of an adverse condition comprises at least one processor programmed to process the physiologic data from a patient or a medical records repository. The at least one processor can also be programmed to detect perturbations of the physiologic data, and detect forces which may have induced the perturbations. In some examples, the at least one processor can also detect and identify, as a select group, force-perturbation associations which are comprised of associations of perturbations of the medical data with perturbation forces which may have induced the perturbations. Furthermore, the at least one processor may also generate a time matrix of the force-perturbation associations, identify a pattern of said force-perturbation associations, and generate an image responsive to the pattern.

In some examples, the force-perturbation associations are force binaries and a force binary is comprised of at least one perturbation of physiologic data and at least one perturbation force which may have induced the perturbation. Additionally, a pattern can change over time and the image can be a motion image responsive to the changes of the pattern. Furthermore, a pattern can include a multi-dimensional distortion of the time matrix of physiologic data, the distortion comprising grouped, bonded, linked, related, encapsulated, or connected perturbations and at least one perturbation inducing force. In some examples, a processor generates a real-time or near real-time global time matrix of the physiologic data and the distortion is real time or near real-time distortion of the global time matrix generated from the medical data.

In some embodiments, at least one processor is programmed to generate a multi-dimensional motion image responsive to said pattern, and to display in real-time or near real-time, motion images indicative of at least one of disease, drug reaction, age related decline in function, or clinical failure, the display comprising an organized image comprising dynamic color displays responsive to grouped, bonded, linked, related, encapsulated, or connected force binaries.

In some embodiments, a patient monitoring system for generating a motion image responsive to a clinical condition and for identification of the cause of the clinical condition comprises at least one processor programmed to process medical data from a patient or medical records repository. The at least one processor can also be programmed to detect perturbations in the medical data, detect forces which induced said perturbations in the medical data, convert the perturbations into perturbation objects, and convert the forces into force objects. Additionally, the at least one processor can also be programmed to link the force objects with the perturbation objects, generate a specific grouping of the linked force objects and perturbation objects, and generate a motion image responsive to the grouping. In some examples, the medical data comprises biologic particle densities.

In some embodiments, at least one processor can be programmed to identify and link exogenous forces which induced a first group of perturbations of biologic particle densities with said first group of induced perturbations. The at least one processor can also be programmed to identify and link endogenous forces which induced a second group of perturbations of biologic particle densities with said second group of induced perturbations. In some examples, the at least one processor generates a unified time matrix of biologic particle densities and the grouping comprises a distortion of the unified time matrix.

In some embodiments, a patient monitoring system for generating an image indicative of the cause of a medical condition comprises at least one processor programmed to generate a time matrix comprising biologic particle densities, identify a perturbation cascade comprising perturbations of the biologic particle densities, and identify a force cascade comprising forces which induced the perturbation cascade. In some examples, the at least one processor is programmed to link the perturbation cascade with the force cascade. Additionally, the at least one processor can identify at least one triggering event, wherein the at least one triggering event induced said force cascade and said perturbation cascade. The triggering event can include at least one treatment or a surgical procedure.

In some embodiments, a patient monitoring system for generating an image responsive to causation of at least one adverse condition comprises at least one processor programmed to generate a force binary comprised of at least, a first object comprising a force, said force comprising at least one biologic particle density or at least one biologic particle density perturbation, and a second object comprised of at least one biologic particle density perturbation induced by the force. The at least one processor can also be programmed to generate a plurality of force binaries, link the force binaries to each other to generate a force cascade comprised of linked force binaries, and identify or generate an image responsive to the force cascade. In some examples, a processor is programmed to generate a time matrix of biologic particle densities and the force cascade comprises a distortion of said time matrix, the at least one processor generating an image responsive to the distortion. Additionally, a processor can be programmed to identify the clinical condition which induced the force cascade. Furthermore, at least one processor can be programmed to order tests responsive to identification of the force cascade. In addition, at least one processor can be programmed to order treatments responsive to identification of the force cascade.

In some embodiments, a patient monitoring system for generating a medical condition and an image, and determining the cause of the medical condition can include at least one processor programmed to process medical data comprised of biologic particle densities. The at least one processor can also be programmed to generate a time matrix comprised of the biologic particle densities, detect a grouping of perturbations of the biologic particle densities, and detect forces which may have induced or caused the grouping. In addition, the at least one processor can be programmed to link the forces and the grouping to generate at least one image primer comprised of an incomplete image of a patient condition and generate an image responsive to the at least one image primer. Furthermore, the at least one processor can be programmed to take action based on the detection of the at least one image primer. In some examples, at least one processor programmed to identify the at least one image primer as comprising a partial image of the medical condition, order tests based on detection of the at least one image primer to generate a more complete image, and identify said more complete image as an image of the medical condition.

In some embodiments, the action comprises generating one or more questions to be asked of a patient to focus the history in response to the at least one image primer. In other embodiments, the action comprises generating one or more tests to be performed on a patient to complete the image.

In some examples, a patient monitoring system for generating a motion image of a medical condition and at least one cause of the medical condition comprises at least one processor programmed to process biologic particle densities from a patient or medical records repository. The at least one processor can also be programmed to generate a time matrix of the biologic particle densities, and identify and associate an image set of binaries comprising perturbations of the biologic particle densities with other perturbations of biologic particle densities that are potentially part of a same pathophysiologic cascade. Furthermore, the at least one processor can be programmed to identify and associate a force set of binaries comprising perturbations of biologic particle densities with forces that may have induced the perturbations of the biologic particle densities, which are part of the same pathophysiologic cascade as the image set. In addition, the at least one processor can be programmed to generate an image responsive to at least one of the image set and the force set.

In some embodiments, a patient monitoring system for generating an image responsive to perturbations of medical data and perturbation forces which caused the perturbations comprises at least one processor programmed to process the medical data from a patient or medical records repository. The at least one processor can also be programmed to generate a time matrix of the medical data, detect the perturbations the medical data, and generate a time matrix of the perturbations. In addition, the at least one processor can be programmed to detect forces which may have induced the perturbations and generate, along the time matrix of the perturbations, associations comprising a cascade of perturbations of the medical data with a matching cascade of perturbation forces which may have induced the perturbations. Furthermore, the at least one processor can be programmed to identify a pattern of said associations and generate an image responsive to the pattern.

What is claimed is:
1. A system comprising:
an electronic medical record search engine for automatic early detection of adverse drug reactions, the search engine having a processor, a display and
a memory storing instructions that, when executed by the processor, cause the system to:
receive a first hospital database containing electronic medical records from a patient population comprising hundreds of thousands of patients who were at one time in the hospital, the electronic medical records including millions of time-linked laboratory test values and treatment data of the patients; and
define a set of subsets of the patient population;
generate a set of submatrices comprised of time series of matrices of laboratory values of treatment data for each of the subsets of the patient populations;
detect rise and fall events along each submatrix, wherein a rise event comprises a rise in laboratory values over time and a fall event comprises a fall in laboratory values over time;
statistically process the rise and fall events of each of the subsets of the patient population to determine a range of unperturbed laboratory variation in each subset, wherein the unperturbed laboratory variation comprises rise and fall events which occur without, at least, the presence of a treatment which may have induced the rise or fall event;
for each population subset, define a set of perturbations corresponding to a set of treatments, each of the perturbations being one of a rise of the values of that test or a fall of the values of that test which is outside said determined range for a given subset of patients;
receive in real time a second hospital database of patients presently within a hospital, the second database containing electronic medical records from the patients presently within the hospital, the electronic medical records including time series of laboratory test values for the patients;
for each time series of laboratory test values, detect, if present, at least one perturbation of each time series which is outside said determined range; and
for each time series of laboratory test values, detect if present, at least one recovery of each time series, each of the recoveries being one of a rise of the values of that test or a fall of the values of that test following a perturbation and in the opposite direction of the perturbation;
generate a time-series matrix of perturbations and recoveries for each patient of the population subset,
store, the generated time series matrix of perturbations and recoveries in a storage data base,
search the storage database for quaternaries in at least a portion of the storage database, wherein each quaternary comprises an ordinal grouping of the at least four search elements, the at least four search elements including:
a perturbation;
at least one perturbation force comprising a first treatment which is capable of inducing and may have induced the perturbation, the perturbation force occurring prior to the perturbation;
a recovery comprising a rise or a fall of the laboratory values following the perturbation and in the opposite direction of the perturbation; and
at least one recovery force comprising a second treatment which is capable of inducing and may have induced the recovery of said perturbation, the second treatment occurring before the recover, and in response to identifying at least the perturbation of a quaternary, generate at least one of a visual alarm on the display or an order for an additional laboratory test to confirm the presence of the perturbation, and generate an output of each of the detected search elements comprising the quaternary in a single view on the display in the order of occurrence and in time relation to the medical record of the patient exhibiting the elements at the time of the occurrence of the quaternary.

2. The system of claim 1, wherein the memory stores instructions that, when executed by the processor, cause the processor to link or group the at least four search elements after detection to generate the quaternary.

3. The system of claim 1, wherein the at least one perturbation force is a procedure.

4. The system of claim 1, wherein the at least one perturbation force is at least one of surgery, central line placement, or initiation of intravenous nutrition.

5. The system of claim 1, wherein the perturbation is induced by *Clostridium difficile* and the at least one perturbation force is at least one first antibiotic.

6. The system of claim 1, wherein the perturbation is induced by *Clostridium difficile* and the at least one recovery force is discontinuation of the at least one first antibiotic.

7. The system of claim 1, wherein the perturbation is induced by *Clostridium difficile* and the at least one perturbation force is a cephalosporin and the at least one recovery force is discontinuation of the cephalosporin.

8. The system of claim 1, wherein the perturbation is induced by *Clostridium difficile* and the at least one recovery force is at least one first antibiotic.

9. The system of claim 1, wherein the at least one recovery force is at least one antibiotic.

10. The system of claim 1 further comprising a graphical user interface for receiving input of temporal relationships of the search elements.

11. The system of claim 1, wherein the processor is programmed to convert the laboratory values in the database into vectors comprising at least the slope of the rise events and fall events of the laboratory values prior to searching.

12. The system of claim 1, wherein the system is configured to search for quaternaries in real-time in response to receiving updated laboratory values and treatment data.

13. A system comprising:

an electronic medical record search engine for automatic early detection of adverse drug reactions, the search engine having a processor, a display and a memory storing instructions that, when executed by the processor, cause the system to:

receive a first hospital database containing electronic medical records from a patient population comprising hundreds of thousands of patients in the hospital, the electronic medical records including millions of time-linked laboratory test values and treatment data for the plurality of patients;

define a set of subsets of the patient population;

generate a set of submatrices comprised of time series of matrices of laboratory values of treatment data for each of the subsets of the patient populations;

detect rise and fall events along each submatrix, wherein a rise event comprises a rise in laboratory values over time and a fall event comprises a fall in laboratory values over time;

statistically process the rise and fall events of each of the subsets of the patient population to determine a range of unperturbed laboratory variation in each subset, wherein the unperturbed laboratory variation comprises rise and fall events which occur without, at least, the presence of a treatment which may have induced the rise or fall event;

for each population subset, define a set of perturbations corresponding to a set of treatments, each of the perturbations being one of a rise of the values of that test or a fall of the values of that test which is outside said determined range for a given subset of patients;

receive in real time a second hospital database of patients presently within a hospital, the second database containing electronic medical records from the patients presently within the hospital, the electronic medical records including time series of laboratory test values for the patients;

for each time series of laboratory test values, detect, if present, at least one perturbation of each time series which is outside said determined range; and for each time series of laboratory test values, detect if present, at least one recovery of each time series, each of the recoveries being one of a rise of the values of that test or a fall of the values of that test following a perturbation and in the opposite direction of the perturbation;

generate a time-series matrix of perturbations and recoveries for each patient of the population subset, store, the generated time series matrix of perturbations and recoveries in a storage data base, search the storage database for quaternaries in at least a portion of the storage database, wherein each quaternary comprises an ordinal grouping of at least four search elements, the at least four search elements including:

a perturbation values, the perturbation having an onset and an end;

at least one perturbation force comprising a first treatment which is capable of inducing and may have induced the perturbation, the perturbation force occurring prior to the perturbation;

a first time interval between the perturbation force and the onset of the perturbation;

a recovery, the recovery having an onset;

a second time interval between the end of the perturbation and the onset of the recovery;

at least one recovery force comprising a second treatment which is capable of inducing and may have induced the recovery of said perturbation, the recovery force occurring before the recovery; and a third time interval between the recovery force and the onset of the recovery; and in response to identifying at least the perturbation of a quaternary, generate at least one of a visual alarm on the display or an order for an additional laboratory test to confirm the presence of the perturbation, and generate an output of each of the detected search elements comprising the quaternary in a single view on the display in the order of occurrence in time relation to a display of the medical record of the patient exhibiting the elements at the time of the occurrence of the quaternary.

14. The system of claim 12, wherein the processor is programmed to detect an incomplete or absent recovery and to output an indication of an incomplete or absent recovery.

* * * * *